(12) United States Patent
Tsuji et al.

(10) Patent No.: US 11,649,311 B2
(45) Date of Patent: *May 16, 2023

(54) TEMPERATURE-SENSITIVE FLUORESCENT PROBE FOR INTRODUCTION INTO CELL

(71) Applicants: KIRIN HOLDINGS KABUSHIKI KAISHA, Tokyo-to (JP); THE UNIVERSITY OF TOKYO, Tokyo-to (JP)

(72) Inventors: Toshikazu Tsuji, Nakano-ku (JP); Kumiko Ikado, Nakano-ku (JP); Seiichi Uchiyama, Bunkyo-ku (JP); Kyoko Kawamoto, Bunkyo-ku (JP)

(73) Assignees: KIRIN HOLDINGS KABUSHIKI KAISHA, Tokyo (JP); THE UNIVERSITY OF TOKYO, Tokyo (JP)

( * ) Notice: Subject to any disclaimer, the term of this patent is extended or adjusted under 35 U.S.C. 154(b) by 390 days.

This patent is subject to a terminal disclaimer.

(21) Appl. No.: 16/219,035

(22) Filed: Dec. 13, 2018

(65) Prior Publication Data

US 2019/0113505 A1    Apr. 18, 2019

Related U.S. Application Data

(60) Division of application No. 14/282,530, filed on May 20, 2014, now Pat. No. 10,191,035, which is a (Continued)

(30) Foreign Application Priority Data

Dec. 21, 2011   (JP) ................................. 2011-280202

(51) Int. Cl.
    *C08F 220/60*   (2006.01)
    *C08F 220/56*   (2006.01)
    (Continued)

(52) U.S. Cl.
    CPC .......... *C08F 220/60* (2013.01); *C08F 220/56* (2013.01); *C08F 228/06* (2013.01);
    (Continued)

(58) Field of Classification Search
    CPC ..... G01N 33/52; C08F 220/56; C08F 220/60; C08F 228/06
    See application file for complete search history.

(56) References Cited

U.S. PATENT DOCUMENTS

| 5,853,694 A | 12/1998 | Engberts et al. |
| 2004/0091448 A1* | 5/2004 | Kross .................... A61K 31/14 424/70.24 |
| 2006/0257858 A1 | 11/2006 | Chiou et al. |

FOREIGN PATENT DOCUMENTS

| JP | 09-285290 A | 11/1997 |
| JP | 2007-252304 A | 10/2007 |

(Continued)

OTHER PUBLICATIONS

Uchiyama, Seiichi etal "Modulation of the Sensitive Temperature Range of Fluorescent Molecular Thermometers Based on Thermoresponsive Polymers" 2004 Analytical Chemistry 76 p. 1793-1798 (Year: 2004).*

(Continued)

*Primary Examiner* — Ling Siu Choi
*Assistant Examiner* — David L Miller
(74) *Attorney, Agent, or Firm* — Sughrue Mion, PLLC

(57) ABSTRACT

There is provided a method for introducing a temperature-sensitive probe comprising a copolymer, which comprises a thermoresponsive unit and a fluorescent unit, into a cell, and the method using the copolymer further comprising a cationic unit as the temperature-sensitive probe, and the method comprising the step of mixing the copolymer with the cell in a solvent. The copolymer can be preferably used (Continued)

as a fluorescence temperature sensor which measures intracellular temperature since the copolymer has a cationic group and thus enters into a cell without using a special method.

1 Claim, 43 Drawing Sheets

Related U.S. Application Data continuation-in-part of application No. PCT/JP2012/083328, filed on Dec. 21, 2012.

(51) Int. Cl.
    *C08F 228/06*    (2006.01)
    *G01N 33/52*    (2006.01)
    *C08F 220/38*    (2006.01)
    *C08F 28/06*    (2006.01)

(52) U.S. Cl.
    CPC .............. *G01N 33/52* (2013.01); *C08F 28/06* (2013.01); *C08F 220/38* (2013.01); *C08F 220/382* (2020.02); *C08F 220/606* (2020.02)

(56) References Cited

FOREIGN PATENT DOCUMENTS

| JP | 2008-537882 A | 10/2008 | | |
|---|---|---|---|---|
| JP | 2009-536030 A | 10/2009 | | |
| WO | 2008/029770 A1 | 3/2008 | | |
| WO | WO-2008029770 A1 | * | 3/2008 | ............ C08F 220/56 |

OTHER PUBLICATIONS

Pelah, Avishay et al. "Protein manipulation by stimuli-responsive polymers encapsulated in erythrocyte ghosts" 2009 Soft Mater 5 (5) p. 1006-1010 (Year: 2009).*

Kobayashi, Hiroki et al. "Dual Temperature and PH Responsive Fluorescence Molecular Probe for Cellular Imaging Utilizing a PNIPAAm-Fluorescein Copolymer" Aug. 2009 Analytical Sciences vol. 25 Issue 8 pp. 1043-1047 (Year: 2009).*

Imazato, Satoshi etal, "Bactericidal activity and cytotoxicity of an antibacterial monomer MDPB" 1999 Biomaterials 20 899-903 (Year: 1999).*

Sherba, Joseph et al. "The effects of electroporation buffer composition on cell viability and electro-transfection efficiency" Nature 2020 10 3053 p. 1-9 (Year: 2020).*

Ehrenberg, B. et al. 1988. Membrane potential can be determined in individual cells from the Nernstian distribution of cationic dyes. Biophysical Journal 53: 785-794. specif. pp. 785, 786, 787, 792.

Eng. translation—Uchiyama, S. et al. International Patent Application Publication No. WO 2008/029770. Fluorescent molecular thermometer. specif. pp. 2, 3, 4, 5, 6, 16, 22, 23, 24.

Gota, C. et al. 2009. Hydrophilic fluorescent nanogel thermometer for intracellular thermometry. Journal of the American Chemical Society (JACS) Communications 131: 2766-2767. specif. p. 2766, 2767.

Kuhry, J-G. et al. 1983. TMA-DPH: a suitable fluorescence polarization probe for specific plasma membrane fluidity studies in intact living cells. Cell Biophysics 5: 129-140. specif, pp. 129, 130, 131, 133.

Wang, D. et al. 2009. BODIPY-conjugated thermoresponsive copolymer as a fluorescent thermometer based on polymer microviscosity. Langmuir 25(22): 13176-13182. specif. pp. 13176, 13179.

* cited by examiner

Differential interference image  Fluorescent image (520 nm-560 nm)

TEMPERATURE-SENSITIVE FLUORESCENT PROBE FOR INTRODUCTION INTO CELL

REFERENCE TO RELATED APPLICATION

This is a divisional of U.S. patent application Ser. No. 14/282,530, filed May 20, 2014 which is a continuation-in-part application of PCT Application No. PCT/JP2012/083328, filed Dec. 21, 2012, and claiming the benefit of priority from Japanese Patent Application No. 2011-280202, filed Dec. 21, 2011, the entire contents of all of which are incorporated herein by reference.

TECHNICAL FIELD

The present invention relates to a novel fluorescent polymer and a simple measurement method of an intracellular temperature using the polymer.

BACKGROUND ART

Many chemical reactions occurring during the process in which cells uptake nutrients and energy is taken out by metabolism greatly depend on temperature. In other words, it can be said that various functions and reactions of cells are controlled by intracellular or extracellular temperature. For example, researches using physical properties of temperature are frequently found in medical research, and abnormal thermogenesis in cancer cells, etc. has been reported (Non Patent Document 1: Scand. J. Haematol. 1986; 36: 353-357). It is possible to use thermogenesis to distinguish between cancer cells with high metabolic activity and normal cells without such activity. By using this, development of therapies and drug discovery targeting thermogenesis has been studied.

Not only in medical research, temperature control is also important in food industry such as fermentation processes in which microorganisms are used to control cellular metabolic activity. For example, in brewing of liquors, the existence of correlation between heat production from yeast and production of ethanol has been studied (Non Patent Document 2: Biotech. Bioeng. 1989; 34: 86-101).

On the other hand, despite the fact that temperature is an important biological indicator and that many of important intracellular reactions occur intracellularly, there are few attempts to measure intracellular temperature. One reason for this was that temperature measurement methods for micro-regions at the cellular level have not been established. However, recent researches have begun to study the use of a molecule material with variable physical properties depending on change in temperature as a temperature sensor (Non Patent Document 3: Photochem. Photobiol. 1995; 62: 416-425; Non Patent Document 4: J. Phys. D: Appl. Phys. 2004; 37: 2938-2943; Non Patent Document 5: Anal. Chem. 2006; 78: 5094-5101; Non Patent Document 6: Appl. Phys. Lett. 2005; 87: 201102; Non Patent Document 7: Biophys. J. 1998; 74: 82-89), and in particular, a high-performance molecular temperature sensor with a minimum functional unit of one molecule was developed and its application to cells has begun to be studied.

There has already been reported, as an example of a molecular temperature sensor, a fluorescent temperature sensor based on the principle that a 2,1,3-benzoxadiazolyl group as an environmentally responsive fluorophore is incorporated into polyacrylamide as a thermoresponsive polymer (Non Patent Document 8: Anal. Chem. 2003; 75: 5926-5935). This polymeric fluorescent temperature sensor has a property that the fluorescence intensity increases with a rise in temperature in an aqueous solution by a phase transition of polyacrylamide induced by heat, thus making it possible to observe a change of temperature in the system by measuring the fluorescence intensity.

There has also been reported the use of a microgel of polyacrylamide containing a fluorophore incorporated thereinto, which is obtained by adding a cross-linking agent during production of a polymer, as a fluorescent temperature sensor (Non Patent Document 9: J. Mater. Chem. 2005; 15: 2796-2800; Non Patent Document 10: J. Am. Chem. Soc. 2009; 131: 2766-2767). Furthermore, it has been reported that incorporation of an ionic functional group into a polymer expands the measuring temperature responsive range by inhibiting the aggregation of polymer (Patent Document 1: PCT/JP 2008/029770).

It has already been reported that the temperature range in which a fluorescent polymeric sensor responds in an aqueous solution can be selected by changing the structure of acrylamide as the main chain used as a thermoresponsive units (Non Patent Document 11: Anal. Chem. 2004; 76: 1793-1798), and it was also possible that a plurality of acrylamide compounds are used for a thermoresponsive unit for the temperature responsive range of interest.

REFERENCE LIST

Non Patent Document

[Non Patent Document 1]
Scand. J. Haematol. 1986; 36: 353-357
[Non Patent Document 2]
Biotech. Bioeng. 1989; 34: 86-101
[Non Patent Document 3]
Photochem. Photobiol. 1995; 62: 416-425
[Non Patent Document 4]
J. Phys. D: Appl. Phys. 2004; 37: 2938-2943
[Non Patent Document 5]
Anal. Chem. 2006; 78: 5094-5101
[Non Patent Document 6]
Appl. Phys. Lett. 2005; 87, 201102
[Non Patent Document 7]
Biophys. J. 1998; 74: 82-89
[Non Patent Document 8]
Anal. Chem. 2003; 75: 5926-5935
[Non Patent Document 9]
J. Mater. Chem. 2005; 15: 2796-2800
[Non Patent Document 10]
J. Am. Chem. Soc. 2009; 131: 2766-2767
[Non Patent Document 11]
Anal. Chem. 2004; 76: 1793-1798

Patent Document

[Patent Document 1]
WO 2008/029770 A

SUMMARY OF THE INVENTION

Technical Problem

A fluorescent polymeric temperature sensor which uses a linear or cross-linked polyacrylamide containing a fluorophore incorporated thereinto, had an advantage which can measure intracellular temperature, but had a problem that need a microinjection technique to introduce polymers into a cell.

Furthermore, for microorganism cells and plant cells, there was an enormous problem in using these polymers because microinjection method cannot be used to introduce a substance into these cells.

Furthermore, there was a problem that when the temperature in a limited micro-space as represented by an intracellular space is measured, it is unknown whether the fluorescence intensity from a temperature-responsive polymer is caused by the temperature surrounding the polymer or by the concentration of the polymer in the micro-space.

Also, there was the following problem, although it was known that the temperature responsive range can be changed in a solution by changing an acrylamide compound, it is unknown that the temperature responsive range can be selected by changing an acrylamide compound because a polymeric sensor may interact intracellularly with various molecules such as proteins, nucleic acids, and lipids, even more, it is totally unexpected how the polymeric sensor responds within cell when a plurality of acrylamide compounds are used in one sensor, and it is unknown whether a sensor with a temperature responsive range of interest for intracellular measurement can be actually and freely fabricated.

For already reported polymers with regard to a fluorescent polymeric temperature sensor which uses a linear or cross-linked polyacrylamide containing a fluorophore incorporated thereinto, high-precision measurement required fluorescence lifetime measurement that is not affected by the concentration of a polymer. However, fluorescence lifetime measurement was not versatile because it requires special devices and is not widely available especially in biological research institutions. Fluorescence lifetime measurement is time-consuming, and thus has a low temporal resolution and is not suitable to capture a rapid intracellular phenomenon.

Furthermore, other than fluorescence lifetime, measurement of ratio of fluorescence intensity is known as a method independent of the concentration of a fluorescent sensor. However, high-sensitivity measurement is difficult because two fluorescent units with usually different structures have to be used and temperature responsive sensitivity often indicates low value when there is a great overlap emission wavelengths between two fluorescent units.

For the pursuit of more versatile measurement, it is desirable that two fluorescent dyes are simultaneously excited by one excitation wavelength. For example, there is a ratiometric measurement method, like a two-wavelength excitation one-wavelength emission detection type, such as Fura-2 used in Ca ion measurement, but instruments such as microscope or spectrofluorometer with simultaneous multi-wavelength excitation or plate reader are expensive and limited for use.

Solution

The present inventors have intensively studied so as to achieve the above objects, and found that a polymer with cationic unit can be used as a highly practical intracellular fluorescent temperature sensor which is applicable to many type of cells, such as microorganisms like yeast cells, animal cells, and plant cells, and does not require high level technology like for microinjection. Furthermore, the present inventors have found that intracellular temperature or temperature in a micro-space can be measured more versatilely and accurately by calculating temperature from a ratio of fluorescence intensities in a plurality of wavelengths obtained using the introduced polymer. Furthermore, the present inventors have confirmed that intracellular temperature or temperature in a micro-space can be measured well also using a fluorescence lifetime as an index. Moreover, the present inventors have found that a temperature-responsive region within cell can be controlled in detail by using a copolymer comprising plural types of thermoresponsive units in one molecule as a temperature-sensitive probe. The present invention is based on these findings.

According to a first aspect of the present invention, there is provided a method for introducing a temperature-sensitive probe comprising a copolymer, which comprises a thermoresponsive unit and a fluorescent unit, into a cell, the method using the copolymer further comprising a cationic unit as a temperature-sensitive probe, and the method comprising the step of mixing the copolymer with cells in a solvent.

Furthermore, according to the present invention, there is provided a method for measuring an intracellular temperature, the method comprising the steps of: (a) introducing a temperature-sensitive probe into a cell in accordance with the method according to the first aspect of the present invention, and (b) measuring a fluorescence intensity or fluorescence lifetime under excitation light irradiation.

According to a second aspect of the present invention, there is provided a method for measuring an intracellular temperature, the method comprising the steps of: (a) introducing a temperature-sensitive probe comprising a copolymer, which comprises a thermoresponsive unit and a fluorescent unit, into a cell, and (b) measuring a fluorescence intensity or fluorescence lifetime under excitation light irradiation, wherein the copolymer comprises two or more types of thermoresponsive units.

According to a third aspect of the present invention, there is provided a method for measuring a temperature using a temperature-sensitive probe comprising a copolymer, which comprises a thermoresponsive unit and a fluorescent unit, the method comprising the steps of: (a) dissolving the temperature-sensitive probe, (b) measuring a fluorescence intensity under excitation light irradiation, and (c) calculating a ratio of fluorescence intensities in two wavelength regions.

According to a fourth aspect of the present invention, there is provided a kit for the measurement of a temperature using the methods according to the first to third aspects of the present invention, the kit comprising the temperature-sensitive probe used in the methods.

Furthermore, the present inventors have intensively studied so as to achieve the above objects, and found that intracellular temperature measurement can be precisely and simply accomplished by adding a new fluorescent unit which can be excited at an identical wavelength as that for a 2,1,3-benzoxadiazolyl group conventionally used in an acrylamide-type fluorescent temperature sensor and shows a emission wavelength different from that for a 2,1,3-benzoxadiazolyl group, and by calculating a ratio of fluorescence intensities derived from two fluorescent dyes. Furthermore, the present inventors have revealed that intracellular temperature distribution can be visualized and determined using this copolymer, and also that these measurements are simple methods that can be adequately performed with a usual fluorescence microscope. The present invention is based on these findings.

According to the fifth aspect of the present invention, there is provided a temperature-sensitive probe comprising a copolymer, which comprises a thermoresponsive unit, a cationic unit, and a fluorescent unit, the temperature-sensitive probe comprising a first fluorescent unit and a second fluorescent unit, each having a mutually different maximum fluorescence wavelength, wherein the thermoresponsive unit is one, or two or more types of repeating units(s) derived from one, or two or more types of monomer(s) represented by the following formula (a):

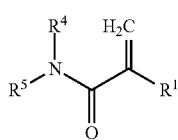

(a)

wherein $R^1$ is selected from hydrogen atom and $C_{1-3}$ alkyl;

$R^4$ and $R^5$ are independently selected from hydrogen atom and $C_{1-20}$ alkyl, in which the alkyl may be optionally substituted by one or more substituent(s) selected from hydroxy, $C_{1-6}$ alkoxy, and aryl, or $R^4$ and $R^5$ may be combined with the nitrogen atom to which they are attached to form a 4- to 8-membered nitrogen-containing hetero ring, in which the hetero ring may be optionally substituted by one or more substituent(s) selected from $C_{1-6}$ alkyl, $C_{1-6}$ alkoxy, nitro, halogen atom, $C_{1-10}$ alkylcarbonylamino, and arylcarbonylamino; and the cationic unit is one, or two or more types of repeating units(s) derived from one, or two or more types of monomer(s) represented by the following formula (b):

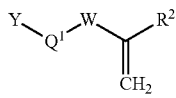

(b)

wherein $R^2$ is selected from hydrogen atom and $C_{1-3}$ alkyl;

W is aromatic ring or —X—C(=O)— (in which $X^1$ is directly bonded to $Q^1$);

$X^1$ is O, S, or N—$R^{11}$;

$R^{11}$ is hydrogen atom, $C_{1-6}$ alkyl, or -$Q^1$-Y, in which the alkyl may be optionally substituted by one or more substituent(s) selected from hydroxy, halogen atom, $C_{1-6}$ alkoxy, $C_{1-6}$ alkylthio, $C_{1-6}$ alkylsulfinyl, and $C_{1-6}$ alkylsulfonyl;

$Q^1$ is independently selected from $C_{1-20}$ alkylene, $C_{3-20}$ alkenylene, or $C_{3-20}$ alkynylene, in which the alkylene may be independently inserted into O, S, —O—P(=O)(—OH)—O—, or phenylene at one or more position(s);

Y is independently an ionic functional group capable of having one or more positive charges, and is selected from —$N^+R^{21}R^{22}R^{23}X_e^-$, —C(=$NR^{41}$)—$NR^{42}R^{43}$, and a group represented by the following formula:

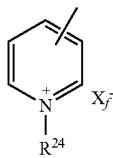

$X_e^-$ and $X_f^-$ are counter anions;

$R^{21}$, $R^{22}$, and $R^{23}$ are independently selected from $C_{1-10}$ alkyl and $C_{7-14}$ aralkyl, or $R^{21}$ and $R^{22}$ may be combined with the nitrogen atom to which they are attached to form a 5- to 7-membered nitrogen-containing hetero ring;

$R^{24}$ is $C_{1-10}$ alkyl, or $C_{7-14}$ aralkyl; and $R^{41}$, $R^{42}$, and $R^{43}$ are independently selected from hydrogen atom and $C_{1-10}$ alkyl, or $R^{41}$ and $R^{42}$ may be combined with the nitrogen and carbon atoms to which they are attached to form a 5- to 7-membered hetero ring containing two nitrogen atoms, or $R^{42}$ and $R^{43}$ may be combined with the nitrogen atom to which they are attached to form a 5- to 7-membered nitrogen-containing hetero ring.

Furthermore, according to a sixth aspect of the present invention, there is provided a method for measuring an intracellular temperature, the method comprising the steps of: (a) mixing the temperature-sensitive probe according to the fifth aspect of the present invention with cells in a solvent, thereby introducing the temperature-sensitive probe into a cell, (b) measuring the fluorescence intensities derived from the first fluorescent unit and the second fluorescent unit under excitation light irradiation, and (c) calculating a ratio of two fluorescence intensities measured.

Effects of Invention

A copolymer used in the present invention can be suitably used as a fluorescent temperature sensor which measures intracellular temperature because the copolymer has a cationic group and thus enters into a cell without using a special method. The present invention is applicable to various cells, such as microorganisms like yeast cells, animal cells, and plant cells. By calculating a ratio of fluorescence intensities of the copolymer in certain two regions, or by using a fluorescence lifetime as a measurement parameter, measurement values become specific to temperature; as a result, a more accurate temperature measurement method independent of the concentration of the copolymer can be provided. Moreover, according to the present invention, a temperature responsive range suitable for measurement can be freely set by combining a plurality of thermoresponsive units.

Furthermore, according to the temperature-sensitive probe according to the fifth aspect of the present invention, it is possible to measure intracellular temperature at a high precision, simply, and in a short time. Furthermore, according to the temperature-sensitive probe according to the fifth aspect of the present invention, intracellular temperature distribution can be visualized and determined. Also, these temperature measurements require no special devices and can be adequately performed with a usual fluorescence microscope. The temperature-sensitive probe according to the fifth aspect of the present invention can be used as a fluorescent temperature sensor which measures intracellular temperature since the probe enters into a cell without using a special method due to a cationic group in the copolymer. Therefore, the present invention is applicable to various cells, such as microorganisms like yeast cells, animal cells, and plant cells. According to the temperature-sensitive probe according to the fifth aspect of the present invention, more accurate temperature measurement independent of the concentration of the copolymer or excitation laser intensity, etc. is possible.

DETAILED DESCRIPTION OF THE INVENTION

Figure 1:
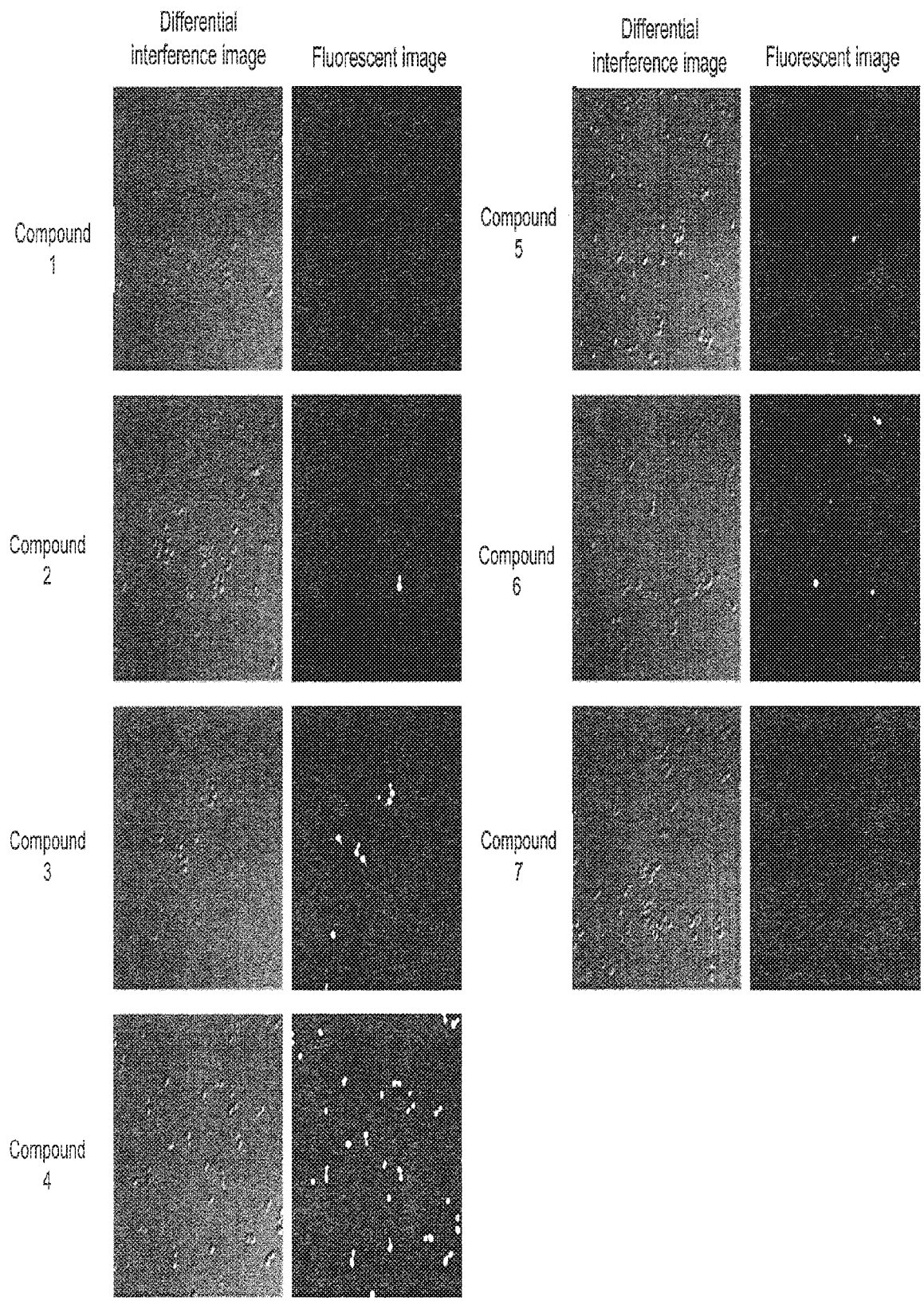
FIG. 1 is an example of photographs when compounds 1 to 7 were mixed with yeast *Saccharomyces cerevisiae* SYT001 and observed by a confocal laser scanning microscope (excitation wavelength of 473 nm, fluorescence wavelength of 500-600 nm).

A. First to Fourth Aspects of the Present Invention

A copolymer used as a temperature-sensitive probe in the first aspect of the present invention comprises a cationic unit as well as a thermoresponsive unit and a fluorescent unit, thereby making it possible to intracellularly introduce the copolymer by mixing the copolymer with a cell in a solvent. Although the copolymer can be intracellularly introduced by a method such as microinjection, the copolymer is intracellularly introduced simply by being mixed with a cell, without such high level technology. Another advantage of the copolymer is that the copolymer can be simply introduced into various cells, such as microorganisms and plant cells, for which microinjection cannot be applied.

The cationic unit to be incorporated into a copolymer used in the present invention is not particularly limited as long as it may be a repeating structure derived from a monomer containing an ionic functional group having one or more positive charges. Such monomer, which is preferably used, is a monomer represented by the following formula (b):

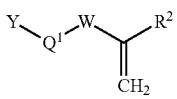

wherein $R^2$ is selected from hydrogen atom and $C_{1-3}$ alkyl;

W is aromatic ring or —$X^1$—C(=O)— (in which $X^1$ is directly bonded to $Q^1$);

$X^1$ is O, S, or N—$R^{11}$;

$R^{11}$ is hydrogen atom, $C_{1-6}$ alkyl, or -$Q^1$-Y, in which the alkyl may be optionally substituted by one or more substituent(s) selected from hydroxy, halogen atom, $C_{1-6}$ alkoxy, $C_{1-6}$ alkylthio, $C_{1-6}$ alkylsulfinyl, and $C_{1-6}$ alkylsulfonyl;

$Q^1$ is independently selected from $C_{1-20}$ alkylene, $C_{3-20}$ alkenylene, or $C_{3-20}$ alkynylene, in which O, S, —O—P(=O)(—OH)—O—, or phenylene may be independently inserted into the alkylene at one or more position(s);

Y is independently an ionic functional group capable of having one or more positive charges, and is selected from —$N^+R^{21}R^{22}R^{23}X_e^-$, —C(=$NR^{41}$)—$NR^{42}R^{43}$, and a group represented by the following formula:

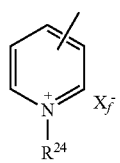

$X_e^-$ and $X_f^-$ are counter anions;

$R^{21}$, $R^{22}$, and $R^{23}$ are independently selected from $C_{1-10}$ alkyl and $C_{7-14}$ aralkyl, or $R^{21}$ and $R^{22}$ may be combined with the nitrogen atom to which they are attached to form a 5- to 7-membered nitrogen-containing hetero ring;

$R^{24}$ is $C_{1-10}$ alkyl or $C_{7-14}$ aralkyl; and $R^{41}$, $R^{42}$, and $R^{43}$ are independently selected from hydrogen atom and $C_{1-10}$ alkyl, or $R^{41}$ and $R^{42}$ may be combined with the nitrogen and carbon atoms to which they are attached to form a 5- to 7-membered hetero ring containing two nitrogen atoms, or $R^{42}$ and $R^{43}$ may be combined with the nitrogen atom to which they are attached to form a 5- to 7-membered nitrogen-containing hetero ring.

The thermoresponsive unit comprised in the copolymer used in the present invention is not particularly limited as long as it is a repeating structure in which the shape varies depending on the temperature, and is preferably a repeating structure derived from a monomer comprising acrylamide as a basic skeleton. Examples of such acrylamide monomer as a basic skeleton include a monomer represented by the following formula (a):

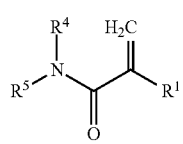

wherein $R^1$ is selected from hydrogen atom and $C_{1-3}$ alkyl;

$R^4$ and $R^5$ are independently selected from hydrogen atom and $C_{1-20}$ alkyl, in which the alkyl may be optionally substituted by one or more substituent(s) selected from hydroxy, $C_{1-6}$ alkoxy, and aryl, or $R^4$ and $R^5$ may be combined with the nitrogen atom to which they are attached to form a 4- to 8-membered nitrogen-containing hetero ring, in which the hetero ring may be optionally substituted by one or more substituent(s) selected from $C_{1-6}$ alkyl, $C_{1-6}$ alkoxy, nitro, halogen atom, $C_{1-10}$ alkylcarbonylamino, and arylcarbonylamino.

The fluorescent unit comprised in the copolymer used in the present invention is not particularly limited as long as it is a repeating structure in which the fluorescence intensity varies depending on change in shape of the thermoresponsive unit. Examples of such repeating structure include those derived from a monomer represented by the following formula (c):

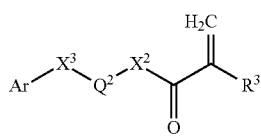

wherein $R^3$ is selected from hydrogen atom and $C_{1-3}$ alkyl;

$X^2$ is O, S, or N—$R^{12}$;

$X^3$ is direct bond, O, S, SO, $SO_2$, N(—$R^{13}$), CON(—$R^{16}$), N(—$R^{16}$)CO, N(—$R^{17}$)CON(—$R^{18}$), $SO_2$N(—$R^{19}$), or N(—$R^{19}$)$SO_2$;

$Q^2$ is selected from $C_{1-20}$ alkylene, $C_{3-20}$ alkenylene, or $C_{3-20}$ alkynylene, in which O, S, or phenylene may be independently inserted into the alkylene at one or more position(s);

Ar is selected from a 6- to 18-membered aromatic carbocyclic group or a 5- to 18-membered aromatic heterocyclic group, in which the aromatic carbocyclic group and aromatic heterocyclic group may contain a fused ring, one or more ring(s) contained therein being aromatic ring(s), —$CH_2$— existing in the aromatic carbocyclic group and the aromatic heterocyclic group as a ring atom may be optionally replaced with —C(O)—, and also the aromatic carbocyclic group and aromatic heterocyclic group may be optionally substituted by one or more substituent(s) selected from halogen atom, $C_{1-6}$ alkyl, $C_{1-6}$ alkoxy, $C_{1-6}$ alkylthio, $C_{1-6}$ alkylsulfinyl, $C_{1-6}$ alkylsulfonyl, nitro, cyano, $C_{1-6}$ alkylcarbonyl, $C_{1-6}$ alkoxycarbonyl, carboxy, formyl, —$NR^6R^7$, and —$SO_2NR^{14}R^{15}$ (in which alkyl contained in the $C_{1-6}$ alkyl, $C_{1-6}$ alkoxy, $C_{1-6}$ alkylthio, $C_{1-6}$ alkylsulfinyl, $C_{1-6}$ alkylsulfonyl, $C_{1-6}$ alkylcarbonyl, and $C_{1-6}$ alkoxycarbonyl may be optionally substituted by one or more substituent(s) selected from halogen atom, $C_{1-6}$ alkoxy, hydroxy, amino, $C_{1-6}$ alkylamino, di($C_{1-6}$ alkyl)amino, aryl, and carboxy);

$R^6$ and $R^7$ are independently selected from hydrogen atom, $C_{1-10}$ alkyl, aryl, $C_{1-10}$ alkylcarbonyl, arylcarbonyl, $C_{1-10}$ alkylsulfonyl, arylsulfonyl, carbamoyl, N—($C_{1-10}$ alkyl)carbamoyl, and N,N-di($C_{1-10}$ alkyl)carbamoyl, in which alkyl contained in the $C_{1-10}$ alkyl, $C_{1-10}$ alkylcarbonyl, $C_{1-10}$ alkylsulfonyl, N—($C_{1-10}$ alkyl)carbamoyl, and N,N-di($C_{1-10}$ alkyl)carbamoyl may be optionally substituted by one or more substituent(s) selected from halogen atom, $C_{1-6}$ alkoxy, hydroxy, amino, $C_{1-6}$ alkylamino, di($C_{1-6}$ alkyl)amino, aryl, and carboxy, and also aryl contained in the aryl, arylcarbonyl, and arylsulfonyl may be optionally substituted by one or more substituent(s) selected from halogen atom, $C_{1-6}$ alkyl, $C_{1-6}$ alkoxy, and carboxy; or $R^6$ and $R^7$ may be combined with the nitrogen atom to which they are attached to form a 4- to 8-membered nitrogen-containing hetero ring, in which the hetero ring may be optionally substituted by one or more substituent(s) selected from $C_{1-6}$ alkyl, $C_{1-6}$ alkoxy, nitro, halogen atom, $C_{1-10}$ alkylcarbonylamino, and arylcarbonylamino;

$R^{12}$ is hydrogen atom, $C_{1-6}$ alkyl, or $-Q^2-X^3-Ar$, in which the alkyl may be optionally substituted by one or more substituent(s) selected from hydroxy, halogen atom, $C_{1-6}$ alkoxy, $C_{1-6}$ alkylthio, $C_{1-6}$ alkylsulfinyl, and $C_{1-6}$ alkylsulfonyl;

$R^{13}$ is hydrogen atom or $C_{1-6}$ alkyl, in which the alkyl may be optionally substituted by one or more substituent(s) selected from hydroxy, halogen atom, $C_{1-6}$ alkoxy, $C_{1-6}$ alkylthio, $C_{1-6}$ alkylsulfinyl, and $C_{1-6}$ alkylsulfonyl;

$R^{14}$ and $R^{15}$ are independently selected from hydrogen atom, and $C_{1-6}$ alkyl; or $R^{14}$ and $R^{15}$ may be combined with the nitrogen atom to which they are attached to form a 4- to 8-membered nitrogen-containing hetero ring; and $R^{16}$, $R^{17}$, $R^{18}$, and $R^{19}$ are independently selected from hydrogen atom and $C_{1-6}$ alkyl, in which the alkyl may be optionally substituted by one or more substituent(s) selected from hydroxy, halogen atom, $C_{1-6}$ alkoxy, $C_{1-6}$ alkylthio, $C_{1-6}$ alkylsulfinyl, and $C_{1-6}$ alkylsulfonyl.

According to preferred embodiment of the present invention, the copolymer used in the present invention is a copolymer comprising repeating structures, each being derived from a monomer represented by formula (a), a monomer represented by formula (b), and a monomer represented by formula (c).

According to still more embodiment of the present invention, the copolymer used in the present invention is a copolymer comprising repeating units represented by formulas (I), (II), and (III):

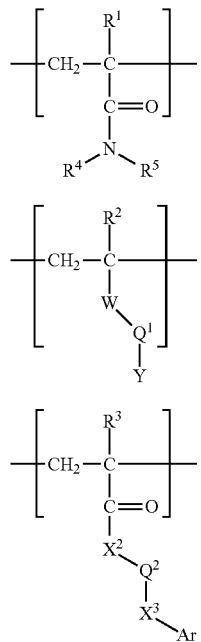

wherein $R^1$, $R^2$, $R^3$, $R^4$, $R^5$, Y, W, $X^2$, $X^3$, $Q^1$, $Q^2$, and Ar are as already defined above.

According to still more embodiment of the present invention, the copolymer used in the present invention is a copolymer represented by formula (IV):

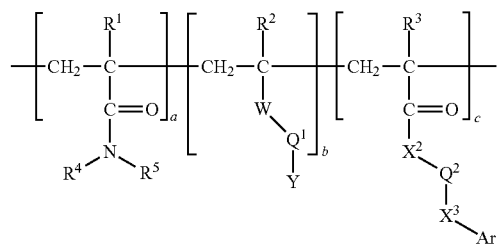

wherein $R^1$, $R^2$, $R^3$, $R^4$, $R^5$, Y, W, $X^2$, $X^3$, $Q^1$, $Q^2$, and Ar are as already defined above, and a, b, and c are numerals representing a ratio of each repeating unit in formula of more than 0. In this copolymer, the sum of a and b is 100, b is preferably 2 to 10, and c is preferably 0.05 to 2. This copolymer constitutes an aspect of the present invention as a substance itself.

According to preferred embodiment of the present invention, the copolymer comprises two or more types of thermoresponsive units. The type of thermoresponsive unit makes various temperature responsive range depending on the type of structure. In this embodiment, it is possible to set desired temperature responsive range by combining two or more types of thermoresponsive units in one copolymer. According to more preferred embodiment of the present invention, the copolymer comprises two or more types of thermoresponsive units represented by the formula (a). In an embodiment, two types of thermoresponsive units are used. In the measurement at usual culture temperature of animal cells, for example, about 35° C., a combination of N-n-propylacrylamide (NNPAM) and N-isopropylacrylamide (NIPAM) is preferably used. When there is a need to measure the temperature region at 25° C. or lower for the purpose of monitoring fermentation of microorganisms such as yeast cells, a combination of N-tert-butylacrylamide (NTBAM) and NNPAM is preferably used.

In formula (IV), "a" represents the sum total of all thermoresponsive units, and represents the sum of ratios of the number of repeating units of all thermoresponsive units when two or more types of thermoresponsive units are used.

According to preferred embodiment of the present invention, in the above-mentioned copolymer, Ar is an aromatic carbocyclic group or an aromatic heterocyclic group selected from groups represented by the following formulas:

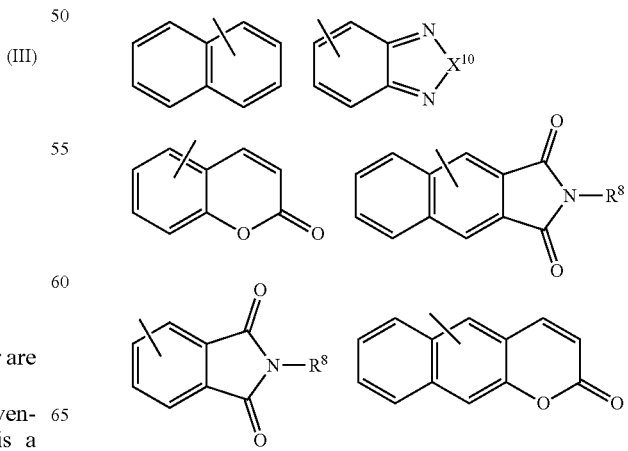

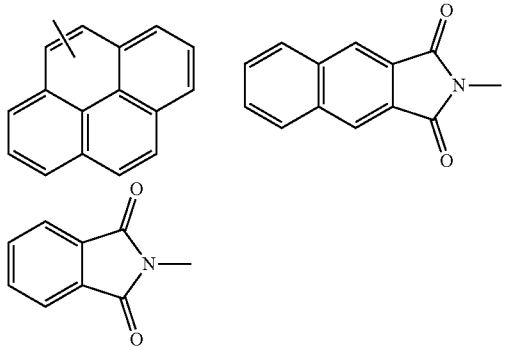

and these groups may be optionally substituted by one or more substituent(s) selected from halogen atom, $C_{1-6}$ alkyl, $C_{1-6}$ alkoxy, $C_{1-6}$ alkylthio, $C_{1-6}$ alkylsulfinyl, $C_{1-6}$ alkylsulfonyl, nitro, cyano, $C_{1-6}$ alkylcarbonyl, $C_{1-6}$ alkoxycarbonyl, carboxy, formyl, $-NR^6R^7$, and $-SO_2NR^{14}R^{15}$ on the ring (in which alkyl contained in the $C_{1-6}$ alkyl, $C_{1-6}$ alkoxy, $C_{1-6}$ alkylthio, $C_{1-6}$ alkylsulfinyl, $C_{1-6}$ alkylsulfonyl, $C_{1-6}$ alkylcarbonyl, and $C_{1-6}$ alkoxycarbonyl may be optionally substituted by one or more substituent(s) selected from halogen atom, $C_{1-6}$ alkoxy, hydroxy, amino, $C_{1-6}$ alkylamino, di($C_{1-6}$ alkyl)amino, aryl, and carboxy);

$X^{10}$ is selected from O, S or Se;

$R^8$ is selected from hydrogen atom, $C_{1-10}$ alkyl, and aryl, and the alkyl may be optionally substituted by one or more substituent(s) selected from halogen atom, $C_{1-6}$ alkoxy, hydroxy, amino, $C_{1-6}$ alkylamino, di($C_{1-6}$ alkyl)amino, aryl, and carboxy, and the aryl may be optionally substituted by one or more substituent(s) selected from halogen atom, $C_{1-6}$ alkyl, $C_{1-6}$ alkoxy, and carboxy.

According to still more embodiment of the present invention, Ar is an aromatic carbocyclic group or an aromatic heterocyclic group selected from groups represented by the following formulas:

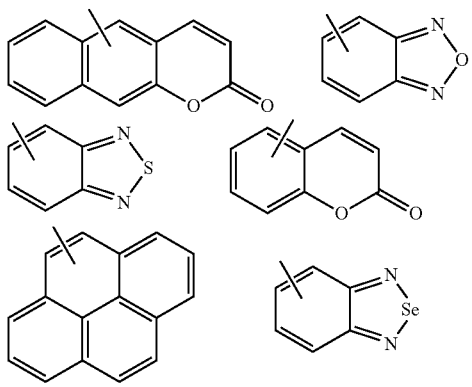

and these groups may be optionally substituted by one or more substituent(s) selected from halogen atom, $C_{1-6}$ alkyl, $C_{1-6}$ alkoxy, $C_{1-6}$ alkylthio, $C_{1-6}$ alkylsulfinyl, $C_{1-6}$ alkylsulfonyl, nitro, $C_{1-6}$ alkylcarbonylamino, arylcarbonylamino, cyano, formyl, $C_{1-6}$ alkylcarbonyl, $C_{1-6}$ alkoxycarbonyl, carboxy, and $-SO_2NR^{14}R^{15}$ on the ring.

As used herein, "$C_{1-3}$ alkyl" means a linear, branched, or cyclic alkyl group having 1 to 3 carbon atoms, and includes methyl, ethyl, n-propyl, i-propyl, and cyclopropyl.

As used herein, "$C_{1-6}$ alkyl" means a linear, branched, cyclic, or partially cyclic alkyl group having 1 to 6 carbon atoms, and includes, for example, methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, and 2-ethylbutyl, cyclopropyl, cyclobutyl, cyclopentyl, cyclohexyl, and cyclopropylmethyl, and also includes, for example, $C_{1-4}$ alkyl and $C_{1-3}$ alkyl.

As used herein, "$C_{1-10}$ alkyl" means a linear, branched, cyclic, or partially cyclic alkyl group having 1 to 10 carbon atoms, and includes, for example, already defined $C_{1-6}$ alkyl and $C_{1-3}$ alkyl.

As used herein, "$C_{1-20}$ alkyl" means a linear, branched, cyclic, or partially cyclic alkyl group having 1 to 20 carbon atoms, and includes, for example, already defined $C_{1-10}$ alkyl, $C_{1-6}$ alkyl, and $C_{1-3}$ alkyl.

As used herein, "$C_{1-6}$ alkoxy" means an alkyloxy group having an already defined alkyl group having 1 to 6 carbon atoms as an alkyl moiety, and includes, for example, methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy, cyclopentyloxy, cyclohexyloxy, cyclopropylmethyloxy, or the like, and also includes, for example, $C_{1-4}$ alkoxy and $C_{1-3}$ alkoxy.

As used herein, "aryl" means a 6- to 10-membered aromatic carbocyclic group, and includes, for example, phenyl, 1-naphthyl, 2-naphthyl, or the like.

As used herein, "$C_{7-14}$ aralkyl" means an aryl alkyl group having 7 to 14 carbon atoms, which has an aryl group, and includes, for example, benzyl, 1-phenethyl, 2-phenethyl, 1-naphthylmethyl, 2-naphthylmethyl, or the like.

As used herein, a halogen atom includes, for example, a fluorine atom, a chlorine atom, a bromine atom, and an iodine atom.

As used herein, "$C_{1-20}$ alkylene" means a linear, branched, cyclic, or partially cyclic alkylene group having 1 to 20 carbon atoms, and includes, for example, methylene, ethylene, propylene, butylene, and $C_{1-10}$ alkylene and $C_{1-6}$ alkylene.

As used herein, "$C_{3-20}$ alkenylene" means a linear, branched, cyclic, or partially cyclic alkenylene group having 3 to 20 carbon atoms and includes, for example, propenylene, butenylene, and the like, and $C_{3-10}$ alkenylene and $C_{3-6}$ alkenylene.

As used herein, "$C_{3-20}$ alkynylene" means a linear, branched, cyclic, or partially cyclic alkynylene group having 3 to 20 carbon atoms, and includes, for example, propynylene, butynylene, and the like, and $C_{3-10}$ alkynylene and $C_{3-6}$ alkynylene.

As used herein, "$C_{1-6}$ alkylthio" means an alkylthio group which has an already defined alkyl group having 1 to 6 carbon atoms as an alkyl moiety, and includes, for example, methylthio, ethylthio, n-propylthio, i-propylthio, n-butylthio, s-butylthio, i-butylthio, t-butylthio, or the like.

As used herein, "$C_{1-6}$ alkylsulfinyl" means an alkylsulfinyl group having an already defined alkyl group having 1 to 6 carbon atoms as an alkyl moiety, and includes, for example, methylsulfinyl, ethylsulfinyl, n-propylsulfinyl, i-propylsulfinyl, n-butylsulfinyl, s-butylsulfinyl, i-butylsulfinyl, t-butylsulfinyl, or the like.

As used herein, "$C_{1-6}$ alkylsulfonyl" means an alkylsulfonyl group which has an already defined alkyl group having 1 to 6 carbon atoms as an alkyl moiety, and includes, for example, methylsulfonyl, ethylsulfonyl, n-propylsulfonyl, i-propylsulfonyl, n-butylsulfonyl, s-butylsulfonyl, i-butylsulfonyl, t-butylsulfonyl, or the like.

As used herein, "6- to 18-membered aromatic carbocyclic group" includes, for example, phenyl, naphthyl, anthracenyl, pyrenyl, indanyl, tetralinyl, or the like.

As used herein, "5- to 18-membered aromatic heterocyclic group" is an aromatic hetero ring having one or more hetero atoms selected from oxygen, nitrogen, and sulfur, and includes, for example, pyrrolyl, pyrazolyl, imidazolyl, pyridyl, indolyl, quinolyl, quinoxalinyl, quinazolinyl, benzofuranyl, benzothienyl, benzopyranyl, benzochromenyl, or the like.

As used herein, "$C_{2-6}$ alkenylsulfonyl" means an alkenylsulfonyl group having an already defined $C_{2-6}$ alkenyl group as an alkenyl moiety, and includes, for example, vinylsulfonyl, allylsulfonyl, or the like.

As used herein, "$C_{2-6}$ alkenylcarbonyl" means an alkenylcarbonyl group having an already defined $C_{2-6}$ alkenyl group as an alkenyl moiety, and includes, for example, acryloyl, methacryloyl, or the like.

As used herein, "$C_{2-6}$ alkynylcarbonyl" means an alkynylcarbonyl group having an already defined $C_{2-6}$ alkynyl group as an alkynyl moiety, and includes, for example, ethynylcarbonyl, or the like.

As used herein, "$C_{1-6}$ alkylcarbonyl" represents a group —CO($C_{1-6}$ alkyl), in which the $C_{1-6}$ alkyl is as already defined above.

As used herein, "$C_{1-6}$ alkoxycarbonyl" represents a group —CO($C_{1-6}$ alkoxy), in which the $C_{1-6}$ alkoxy is as already defined above.

As used herein, "$C_{1-6}$ alkylcarbonylamino" represents a group —NHCO($C_{1-6}$ alkyl), in which the $C_{1-6}$ alkyl is as already defined above.

As used herein, "$C_{1-6}$ arylcarbonylamino" represents a group —NHCO(aryl), in which the aryl is as already defined above.

As used herein, "5- to 7-membered nitrogen-containing hetero ring" includes, for example, saturated hetero rings such as a pyrrole ring, a pyrrolidine ring, a piperidine ring, a homopiperidine ring, a piperazine ring, a homopiperazine ring, a morpholine ring, and a thiomorpholine ring.

As used herein, "4- to 8-membered nitrogen-containing hetero ring" includes, for example, a pyrrole ring, an azetidine ring, a pyrrolidine ring, a piperidine ring, a homopiperidine ring, a piperazine ring, a homopiperazine ring, a morpholine ring, a thiomorpholine ring, or the like, and a 5- to 7-membered nitrogen-containing hetero ring.

As used herein, "5- to 7-membered hetero ring containing two nitrogen atoms" includes, for example, imidazolidine, tetrahydropyrimidine, or the like.

As used herein, when O is inserted into an alkylene at one or more position(s), an alkylene chain contains an ether bond in the main chain, and a person with an ordinary skill in the art should understand that the insertion is performed so as not to form a structure of —O—O— and —O—CH$_2$—O— for the purpose of obtaining a stable structure. The above fact also applies in insertion of S into alkylene.

As used herein, "counter anion" is not particularly limited as long as it is an anion which is usually used as a counter anion of an organic compound in the technical field of organic chemistry, and includes, for example, halide anions (chloride ion, bromide ion, fluoride ion, iodide ion), conjugated base of an organic acid (for example, acetic acid ion, trifluoroacetic acid ion), nitric acid ion, sulfuric acid ion, carbonic acid ion, and the like. The counter anion which is preferred in the present invention includes, for example, chloride ion, nitric acid ion, or the like.

When the counter anion is divalent or higher-valent, formation of the corresponding number of an ionic functional group and an ionic bond is as easily understood by a person with an ordinary skill in the art.

In the present invention, $R^1$, $R^2$, and $R^3$ are preferably selected from hydrogen atom and methyl.

There is no particular limitation on —NR$^4$R$^5$ in formula (a), and formulas (I) and (IV) and, for example, R$^4$ may be hydrogen atom, and R$^5$ may be $C_{2-10}$ alkyl. When R$^4$ and R$^5$ are combined with the nitrogen atom to which they are attached to form a 4- to 8-membered nitrogen-containing hetero ring, for example, a pyrrolidine ring, a piperidine ring, a homopiperidine ring, a piperazine ring, a homopiperazine ring, a morpholine ring, a thiomorpholine ring, or the like may also be formed.

In formula (b), and formulas (II) and (IV), W may be either aromatic ring or —X$^1$—C(=O)— (in which X$^1$ is directly bonded to Q$^1$). The aromatic ring represented by W is preferably a $C_{6-18}$ aromatic ring, and more preferably a benzene ring. W is preferably —X$^1$—C(=O)— (in which X$^1$ is directly bonded to Q$^1$). X$^1$ is preferably O, NH, or N($C_{1-6}$ alkyl).

In formula (b), and formulas (II) and (IV), -Q$^1$- is preferably $C_{2-10}$ alkylene.

In formula (c), and formula (III) and (IV), —X$^2$-Q$^2$- is preferably as follows: X$^2$ is O, NH, or N($C_{1-6}$ alkyl), and Q$^2$ is $C_{2-10}$ alkylene.

In formula (c), and formulas (III) and (IV), —Ar is preferably a group selected from the following formulas (V) to (XII):

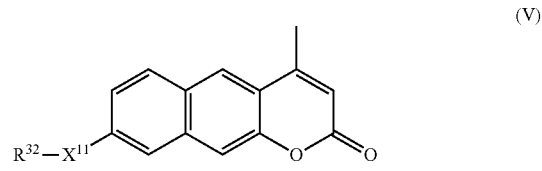

(V)

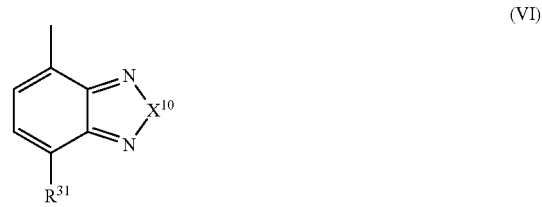

(VI)

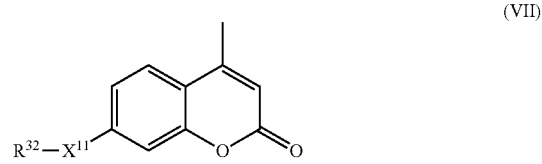

(VII)

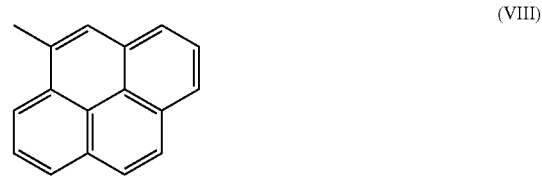

(VIII)

-continued

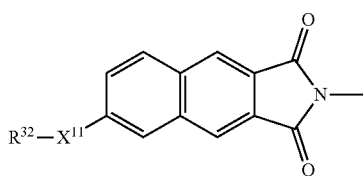
(IX)

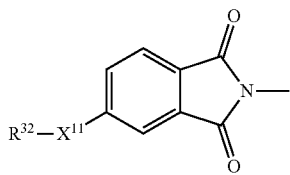
(X)

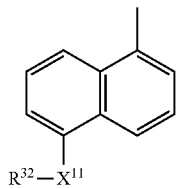
(XI)

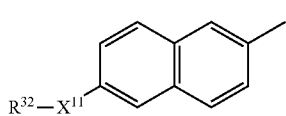
(XII)

wherein $R^{31}$ is selected from hydrogen atom, halogen atom, nitro, cyano, and —$SO_2NR^{14}R^{15}$; $R^{32}$ is $C_{1-6}$ alkyl; $X^{11}$ is N—$R^{33}$, O, or S; $R^{33}$ is hydrogen atom or $C_{1-6}$ alkyl; and $X^{10}$, $R^{14}$ and $R^{15}$ are as already defined above.

For formula (V), preferred $X^3$ includes, for example, direct bond, CON(—$R^{16}$), N(—$R^{16}$)CO, $SO_2$N(—$R^{19}$), or N(—$R^{19}$)$SO_2$.

For formula (VI), preferred $X^3$ includes, for example, N—$R^{13}$ (in which preferred $R^{13}$ includes $C_{1-3}$ alkyl such as methyl), or S.

For formula (VII), preferred $X^3$ includes, for example, direct bond, CON(—$R^{16}$), N(—$R^{16}$)CO, $SO_2$N(—$R^{19}$), or N(—$R^{19}$)$SO_2$.

For formula (VIII), preferred $X^3$ includes, for example, direct bond, CON(—$R^{16}$), N(—$R^{16}$)CO, $SO_2$N(—$R^{19}$), or N(—$R^{19}$)$SO_2$.

For formula (IX), preferred $X^3$ includes, for example, direct bond.

For formula (X), preferred $X^3$ includes, for example, direct bond.

For formula (XI), preferred $X^3$ includes, for example, CO, $SO_2$, $SO_2$N(—$R^{19}$) or CON(—$R^{16}$) (in which a sulfur atom and a carbon atom are respectively bonded to Ar in the $SO_2$N(—$R^{19}$) and CON(—$R^{16}$)).

For formula (XII), preferred $X^3$ includes, for example, CO, $SO_2$, $SO_2$N(—$R^{19}$), or CON(—$R^{16}$) (in which a sulfur atom and a carbon atom are respectively bonded to Ar in the $SO_2$N(—$R^{19}$) and CON(—$R^{16}$)).

In the present invention, a group —$X^3$—Ar functions as an environmental responsive fluorophore and, for example, it is possible to obtain a temperature sensor in which the fluorescence intensity decreases with a rise in temperature when a fluorophore of formula (V) or (VII) is used, while it is possible to obtain a temperature sensor in which the fluorescence intensity also increases with a rise in temperature when a fluorophore of (VI) or fluorophores of (VIII) to (XII) is/are used.

The amount of the monomer of formula (b) used is, for example, 1 to 15 mol % based on the total amount of formulas (a) and (b).

The copolymer according to the present invention can be synthesized based on common knowledge in the technical field of polymer synthesis and, for example, it can be obtained as a random copolymer by radical polymerization. Examples of usable radical initiator in that case include, but are not limited to, persulfates such as ammonium persulfate, sodium persulfate, and potassium persulfate; and azo compounds such as 2,2'-azobis(2-methylpropionamidine) dihydrochloride, 2,2'-azobis[2-(2-imidazolin-2-yl)propane] dihydrochloride, and 4,4'-azobis(4-cyanovaleric acid).

The amount of the reaction initiator used may be 0.01 mol % or more based on the amount of the monomer used, and an appropriate amount can be selected as long as the concentration enables proceeding of radical synthesis. For example, it is possible to use 0.1 mol % or more, and preferably 1 mol % or more, of the reaction initiator.

Examples of the reaction solvent used for polymerization include, but are not limited to, acetonitrile, dioxane, dimethylformamide, methanol, and the like. The radical polymerization is not particularly limited and can be performed, for example, at the reaction temperature of 0 to 100° C., preferably 50 to 70° C., for 1 to 48 hours, and preferably 2 to 16 hours as the reaction time.

In order to measure the temperature without being influenced by the pH and salt concentration in a solution containing the copolymer of the present invention, a cationic functional group contained in the copolymer preferably maintain ionicity within a wide range of the pH. The pH in a cell is 2 to 9 only for the purpose of measuring an intracellular temperature, and is about 4 to 8 in a usual state for common animal, plant, and microbial cells. The functional group preferably controls cationicity at this pH. From such a point of view, Y is preferably —$N^+R^{21}R^{22}R^{23}X_e^-$.

In another aspect of the present invention, there is provided a copolymer comprising repeating structures, each being derived from a monomer represented by formula (a), a monomer represented by formula (b), and a monomer represented by formula (c). The amount of the monomer represented by formula (b) used to obtain the copolymer is, for example, 1 to 15 mol %, preferably 2 to 7.5 mol %, and more preferably 2.5 to 5 mol %, based on the total amount of monomers represented by the formulas (a) and (b). The amount of the monomer represented by formula (c) used is, for example, 0.01 to 20 mol %, specifically 0.01 to 10 mol %, preferably 0.05 to 2 mol %, and more preferably 0.5 to 1.5 mol %, based on the total amount of monomers represented by the formulas (a) and (b).

In formula (IV), a, b, and c are numerals representing a ratio of each repeating unit in formula of more than 0 and is not particularly limited. For example, a+b=100, and c is a proportion based on the total amount of a+b (namely, 100), and c is 0.01 to 20, specifically 0.01 to 10, preferably 0.05 to 2, and more preferably 0.5 to 1.5. When a+b=100, for example, b is 1 or more, preferably 2 or more, more preferably 2.5 or more, and still more preferably 3 or more and is, for example, 15 or less, preferably 10 or less, more preferably 7.5 or less, still more preferably 6 or less, and yet more preferably 5 or less. When a+b=100, for example, b is 1 to 15, preferably 2 to 10, more preferably 2 to 7.5, still more preferably 2.5 to 6, yet more preferably 3 to 6, and further preferably 3 to 5. As mentioned above, a is the sum total of thermoresponsive units and, for example, when two types of thermoresponsive units are used, a ratio of the thermoresponsive unit becomes p:a−p using certain numeral p. For example, when a copolymer is produced so that b becomes 2.5 (a+b=100), and also two types of thermoresponsive units (for example, N-n-propylacrylamide and N-isopropylacrylamide) are used in combination, a is 97.5, and a ratio of N-n-propylacrylamide to N-isopropylacrylamide is represented by p:97.5–p. The weight average molecular weight of the polymer of the present invention is not particularly limited, and is 5,000 to 1,000,000, and preferably 10,000 to 200,000.

Change in the fluorescence intensity due to the thermoresponsivity of a copolymer used in the present invention can be measured by a usual fluorescence intensity measurement method. There is no particular limitation on excitation wavelength in measurement and fluorescence wavelength to be measured, and, for example, the maximum excitation wavelength when the excitation spectrum of a measurement sample is measured or a wavelength near the maximum wavelength can be used. There is also no particular limitation on fluorescence wavelength to be measured, and, for example, the maximum fluorescence wavelength when the fluorescence spectrum of a measurement sample is measured at a temperature at which the fluorescence intensity increases or a wavelength near the maximum wavelength can be used.

Fluorescence lifetime may be used as an index of change in the thermoresponsivity of a copolymer used in the present invention. The change can be measured by a usual fluorescence lifetime measurement method. There is no particular limitation on excitation wavelength in measurement, and, for example, the maximum excitation wavelength when the excitation spectrum of a measurement sample is measured or a wavelength near the maximum wavelength can be used. Fluorescence lifetime values can be obtained from the fluorescence decay curve obtained from an experiment by using a usual analysis method, such as one-component approximation and two-component approximation, according to the state of a measurement sample.

Changes in the fluorescence lifetime due to the thermoresponsivity of a copolymer used in the present invention can be measured by a usual fluorescence lifetime measurement method, e.g., a single photon counting method, a phase modulation method, a pulse sampling method, and an excitation probe method. Of these, a single photon counting method is a method which measures a fluorescence lifetime using the correlation between the emission intensity distribution on the temporal axis and the emission probability of one photon, after a fluorophore is excited by very short (pulse) light of about 1 ns, the time of generation of light detected is measured, and then the fluorescence lifetime is determined by approximating a histogram obtained by repeated excitations as a fluorescence decay curve by the sum of an exponential function. Fluorescence lifetime measurement by a single photon counting method can be performed with a commercially available time correlation single photon counting method fluorescence lifetime measurement device and its accompanying measurement/analysis program.

A "cell" in the present invention consists of usually categorized prokaryotic cells and eukaryotic cells, and does not particularly depend on its biological species. For example, prokaryotic cells are divided into eubacteria and archaebacteria, and eubacteria are especially divided into Gram-positive bacteria such as Actinobacteria and Gram-negative bacteria such as Proteobacteria, the applicable range of a copolymer is not limited by the thickness of a peptidoglycan layer, etc. Eukaryotic cells mainly include cells belonging to eukaryotes (protists, fungus, plants, and animals). For example, yeast, which is usually used in molecular biology research, etc. and also used in industry, belongs to fungus.

When a copolymer of the present invention is introduced into a cell, it is desirable to replace its solution with a solution with a low ionic strength (solvent). Such solvent includes, for example, water (preferably pure water), an aqueous sorbitol solution, and a glucose solution.

The concentration of a copolymer when the copolymer is introduced into a cell in accordance with the present invention, for example, can be prepared so that the final concentration of the copolymer is 0.001 to 1% (w/v), preferably 0.01 to 0.1% (w/v), and be mixed with a fungus body. This applies not only to a microbial body, etc. but also to adherent cells, etc.

In order to accurately measure the temperature in a limited micro-space represented by an intracellular space, it is desirable to measure the fluorescence intensities of two certain independent fluorescence wavelengths to calculate a ratio of them, and convert the ratio of fluorescence intensity into temperature. With this method, it is possible to exclude the possibility that the fluorescence intensity emitted from a copolymer is due to the concentration of the copolymer in the micro-space, and to make a one-to-one correspondence between temperature and the ratio of fluorescence intensity obtained from an experiment. As a result, it is possible not only to compare temperatures of the same cell but also to compare intracellular temperatures of other cells under the same condition. For example, by measuring differences in individual cell temperature in a yeast population, the physiological state of each yeast cell can be grasped.

There is no particular limitation on a calculation method for ratio of fluorescence intensity, and the ratio can be calculated from the fluorescence intensities of two regions comprising different wavelengths. For example, one region is set at 550 nm to 570 nm and the integrated value of its fluorescence intensity is defined as S1; the other region is set at 570 nm to 590 nm and the integrated value of its fluorescence intensity is defined as S2; and S1/S2 may be defined as a ratio of fluorescence intensity. Furthermore, the regions of S1 and S2 may be same width or different width. For example, S1 comprises a wavelength region with a width of 20 nm, while S2 may be a single wavelength with a width of 1 nm. There is no particular limitation on the selection criteria of wavelength; considering the strength of fluorescence intensity obtained, it is desirable to select two wavelength regions (i.e., wavelength regions for S1 and S2) from a range of 200 nm, preferably 150 nm, and more preferably 100 nm, around a wavelength which shows the maximum fluorescence intensity when the emission spectrum of a monomer giving a fluorescent unit comprised in a temperature-sensitive probe (e.g., fluorescent monomer shown in the formula (c)) in water at room temperature (about 25° C.) is measured. When two wavelength regions mentioned above are selected, it is desirable to avoid a baseline wavelength region when the fluorescence spectrum of a monomer giving a fluorescent unit comprised in a temperature-sensitive probe (e.g., fluorescent monomer shown in the formula (c)) in water at room temperature (about 25° C.) is measured, in other words, a wavelength region in which the fluorescence intensity is within the range of noise of a measurement device.

When the temperature is calculated from the ratio of fluorescence intensity obtained from an experiment, a calibration curve set by your own can be used. Specifically, there is no limitation on the condition under which a calibration curve to be used is measured, and, for example, a curve in which change in the fluorescence intensity due to the thermoresponsitivity of a copolymer in a potassium chloride solution imitating an intracellular space is plotted, a curve in which change in the fluorescence intensity due to the thermoresponsitivity by subjecting a cell population into which a copolymer is introduced to a spectrofluorometer are plotted, or a curve in which mean change in the fluorescence intensity due to the thermoresponsitivity in a plurality of cells by subjecting a cell population into which a copolymer is introduced to a fluorescence microscope are plotted, etc. can be used. More specifically, when change in the fluorescence intensity is plotted by performing a thermoresponsivity test with a cell population into which a copolymer is introduced, there is a method for measuring the fluorescence intensity under the condition in which the metabolic activity of a cell is not actively performed, for example, a cell is suspended in water or in a buffer containing a compound which cannot be assimilated, the cell is held at a specific temperature for a certain period, and the external temperature and the intracellular temperature seem to be in an equilibrium. When these fluorescence intensities are measured, the fluorescence intensity may be measured, but by preparing a calibration curve using a ratio of fluorescence intensity between two arbitrary wavelength regions as mentioned above, a more precise calibration curve can be prepared.

The above mentioned temperature measurement method using a ratio of fluorescence intensity can be widely applied to temperature measurement using a copolymer comprising a thermoresponsive unit and a fluorescent unit. This temperature measurement method can be widely applied not only to intracellular temperature measurement but also to temperature measurement in a micro-space.

In order to accurately measure the temperature in a limited micro-space represented by an intracellular space, a fluorescence lifetime can also be used as an index. Fluorescence lifetime measurement is not affected by a wavelength or the concentration of fluorescent substances, and thus exerts advantageous effects similar to those of the measurement using a ratio of fluorescence intensity with two wavelengths. The temperature measurement method with fluorescence lifetime can be widely applied to temperature measurement using a copolymer comprising a thermoresponsive unit and a fluorescent unit. This temperature measurement method can be widely applied not only to intracellular temperature measurement but also to temperature measurement in a micro-space.

Furthermore, the above mentioned embodiment using two or more types of thermoresponsive units can be widely applied not only when a copolymer used in the present invention is used as a temperature-sensitive probe but also to temperature measurement using a copolymer comprising a thermoresponsive unit and a fluorescent unit.

In order to perform the methods described above, all necessary reagent, etc. can be used as a kit. Therefore, according to the fourth aspect of the present invention, there is provided a kit for the measurement a temperature using the above mentioned methods, the kit comprising a temperature-sensitive probe used in these methods. This reagent kit for the measurement of a temperature can be suitably used for the measurement of a temperature in a micro-space, especially intracellular temperature measurement. The reagent kit can be used in research fields such as medicine, biology, and bioengineering, and medical fields such as diagnosis and treatment.

According to one embodiment of the present invention, the kit comprises a temperature-sensitive probe comprising a copolymer, which comprises a thermoresponsive unit, a fluorescent unit, and a cationic unit.

According to other embodiments of the present invention, the kit comprises a temperature-sensitive probe comprising a copolymer, which comprises a thermoresponsive unit and a fluorescent unit, and the copolymer comprises two or more types of thermoresponsive units.

Methods and a kit for the measurement of a temperature of the present invention can be applied to various fields of research and development. For example, in the bioengineering field, it is expected that culture conditions can be considered efficiently in fermentative production of useful substances using microorganisms by adding intracellular temperature, which had been difficult to be accurately measured, to analysis parameters.

Methods and a kit for the measurement of a temperature of the present invention can be applied to various medical uses. For example, using a temperature-sensitive probe according to the present invention for some tissues of patients enables discrimination between cancer cells with more heat production and normal cells without such production. Furthermore, as an application, this probe can be used for development of more efficient thermotherapy, etc. Alternatively, after a temperature-sensitive probe according to the present invention is introduced into a brown adipocyte with more heat production, change in temperature due to addition of various materials to the cell are measured, enabling the screening of materials which activate a brown adipocyte.

Methods and a kit for the measurement of a temperature of the present invention can also be applied to elucidation of various physiological phenomena. For example, by investigating how a TRP channel, a receptor which senses in vitro temperature and causes biological reactions, is associated with intracellular temperature, the TRP channel may be activated by an approach different from conventional one. By investigating the relationship between intracellular temperature distribution and intracellular or extracellular biological reactions, the effects of local temperature distribution on biological reactions can be evaluated, and cells can be controlled by local heating with an infrared laser, etc.

A temperature measurement method and a cell introduction method of a temperature-sensitive probe according to the present invention can be performed either in vitro or in vivo. In one embodiment, these methods are performed in vitro.

B. Fifth and Sixth Aspects of the Present Invention

A copolymer used as a temperature-sensitive probe according to the fifth aspect of the present invention comprises the first fluorescent unit and the second fluorescent unit, each having a different maximum fluorescence wavelength. In the temperature measurement using this temperature-sensitive probe, by calculating a ratio between the fluorescence intensity derived from the first fluorescent unit and the fluorescence intensity derived from the second fluorescent unit, and by matching the ratio to actual temperature, temperature can be measured at a high precision, simply, and in a short time. A copolymer used as a temperature-sensitive probe of the present invention comprises a cationic unit as well as a thermoresponsive unit and a fluorescent unit; thereby enabling intracellularly introducing the copolymer by mixing the copolymer with a cell in a solvent.

It is desirable that the first fluorescent unit and the second fluorescent unit generate fluorescence with a mutually different maximum fluorescence wavelength by excitation light irradiation with the same wavelength. Difference between the maximum fluorescence wavelength of the first fluorescent unit and the maximum fluorescence wavelength of the second fluorescent unit may be adequately distinguished by a measurement device in simultaneous measurement of the fluorescence intensities of two wavelengths, are not particularly limited, and is preferably 50 nm or more.

According to preferred embodiment of the present invention, either of the first fluorescent unit or the second fluorescent unit is a unit in which the fluorescence intensity increased with a rise in temperature, and the other is a unit in which the fluorescence intensity does not change or decrease, desirably decreases, with a rise in temperature.

According to particularly preferred embodiment of the present invention, the first fluorescent unit is a repeating structure derived from a monomer represented by the following formula (c):

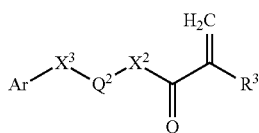

(c)

wherein $R^3$ is selected from hydrogen atom and $C_{1-3}$ alkyl;

$X^2$ is O, S, or N—$R^{12}$;

$X^3$ is direct bond, O, S, SO, $SO_2$, N(—$R^{13}$), CON(—$R^{16}$), N(—$R^{16}$)CO, N(—$R^{17}$)CON(—$R^{18}$), $SO_2$N(—$R^{19}$), or N(—$R^{19}$)$SO_2$;

$Q^2$ is selected from $C_{1-20}$ alkylene, $C_{3-20}$ alkenylene, or $C_{3-20}$ alkynylene, in which O, S, or phenylene may be independently inserted into the alkylene at one or more position(s);

Ar is selected from a 6- to 18-membered aromatic carbocyclic group or a 5- to 18-membered aromatic heterocyclic group, in which the aromatic carbocyclic group and aromatic heterocyclic group may contain a fused ring, one or more ring(s) contained therein being aromatic ring(s), —$CH_2$— existing in the aromatic carbocyclic group and the aromatic heterocyclic group as a ring atom may be optionally replaced with —C(O)—, and also the aromatic carbocyclic group and aromatic heterocyclic group may be optionally substituted by one or more substituent(s) selected from halogen atom, $C_{1-6}$ alkyl, $C_{1-6}$ alkoxy, $C_{1-6}$ alkylthio, $C_{1-6}$ alkylsulfinyl, $C_{1-6}$ alkylsulfonyl, nitro, cyano, $C_{1-6}$ alkylcarbonyl, $C_{1-6}$ alkoxycarbonyl, carboxy, formyl, —$NR^6R^7$, and —$SO_2NR^{14}R^{15}$ (in which alkyl contained in the $C_{1-6}$ alkyl, $C_{1-6}$ alkoxy, $C_{1-6}$ alkylthio, $C_{1-6}$ alkylsulfinyl, $C_{1-6}$ alkylsulfonyl, $C_{1-6}$ alkylcarbonyl, and $C_{1-6}$ alkoxycarbonyl may be optionally substituted by one or more substituent(s) selected from halogen atom, $C_{1-6}$ alkoxy, hydroxy, amino, $C_{1-6}$ alkylamino, di($C_{1-6}$ alkyl)amino, aryl, and carboxy);

$R^6$ and $R^7$ are independently selected from hydrogen atom, $C_{1-10}$ alkyl, aryl, $C_{1-10}$ alkylcarbonyl, arylcarbonyl, $C_{1-10}$ alkylsulfonyl, arylsulfonyl, carbamoyl, N—($C_{1-10}$ alkyl)carbamoyl, and N,N-di($C_{1-10}$ alkyl)carbamoyl, in which alkyl contained in the $C_{1-10}$ alkyl, $C_{1-10}$ alkylcarbonyl, $C_{1-10}$ alkylsulfonyl, N—($C_{1-10}$ alkyl)carbamoyl, and N,N-di($C_{1-10}$ alkyl)carbamoyl may be optionally substituted by one or more substituent(s) selected from halogen atom, $C_{1-6}$ alkoxy, hydroxy, amino, $C_{1-6}$ alkylamino, di($C_{1-6}$ alkyl)amino, aryl, and carboxy, and also aryl contained in the aryl, arylcarbonyl, and arylsulfonyl may be optionally substituted by one or more substituent(s) selected from halogen atom, $C_{1-6}$ alkyl, $C_{1-6}$ alkoxy, and carboxy; or $R^6$ and $R^7$ may be combined with the nitrogen atom to which they are attached to form a 4- to 8-membered nitrogen-containing hetero ring, in which the hetero ring may be optionally substituted by one or more substituent(s) selected from $C_{1-6}$ alkyl, $C_{1-6}$ alkoxy, nitro, halogen atom, $C_{1-10}$ alkylcarbonylamino, and arylcarbonylamino;

$R^{12}$ is hydrogen atom, $C_{1-6}$ alkyl, or -$Q^2$-$X^3$—Ar, in which the alkyl may be optionally substituted by one or more substituent(s) selected from hydroxy, halogen atom, $C_{1-6}$ alkoxy, $C_{1-6}$ alkylthio, $C_{1-6}$ alkylsulfinyl, and $C_{1-6}$ alkylsulfonyl;

$R^{13}$ is hydrogen atom or $C_{1-6}$ alkyl, in which the alkyl may be optionally substituted by one or more substituent(s) selected from hydroxy, halogen atom, $C_{1-6}$ alkoxy, $C_{1-6}$ alkylthio, $C_{1-6}$ alkylsulfinyl, and $C_{1-6}$ alkylsulfonyl;

$R^{14}$ and $R^{15}$ are independently selected from hydrogen atom and $C_{1-6}$ alkyl; or $R^{14}$ and $R^{15}$ may be combined with the nitrogen atom to which they are attached to form a 4- to 8-membered nitrogen-containing hetero ring;

$R^{16}$, $R^{17}$, $R^{18}$, and $R^{19}$ are independently selected from hydrogen atom and $C_{1-6}$ alkyl, in which the alkyl may be optionally substituted by one or more substituent(s) selected from hydroxy, halogen atom, $C_{1-6}$ alkoxy, $C_{1-6}$ alkylthio, $C_{1-6}$ alkylsulfinyl, and $C_{1-6}$ alkylsulfonyl; and second fluorescent unit is a repeating structure derived from a monomer represented by the following formula (d):

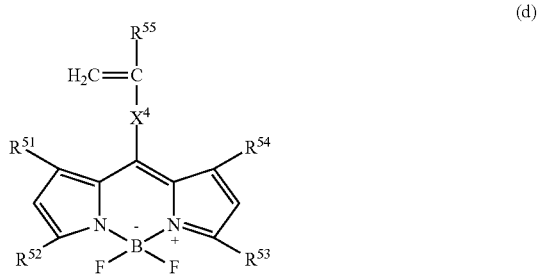

(d)

wherein $R^{55}$ is selected from hydrogen atom and $C_{1-3}$ alkyl;

$R^{51}$, $R^{52}$, $R^{53}$, and $R^{54}$ are independently selected from hydrogen atom and $C_{1-6}$ alkyl;

$X^4$ is direct bond, phenylene, -$Q^4$-O—C(=O)— (in which $Q^4$ is directly bonded to a boron dipyrromethene skeleton), or -$Q^4$-N(—$R^{61}$)—C(=O)— (in which $Q^4$ is directly bonded to a boron dipyrromethene skeleton);

$R^{61}$ is selected from hydrogen atom and $C_{1-6}$ alkyl;

$Q^4$ is selected from $C_{1-20}$ alkylene, phenylene, and naphthylene, in which the phenylene and naphthylene may be optionally substituted by one or more substituent(s) selected from halogen atom, $C_{1-6}$ alkoxy, hydroxy, amino, and carboxy.

The thermoresponsive unit comprised in the copolymer used in the fifth aspect of the present invention is a repeating structure in which the shape varies depending on change in temperature, and is one, or two or more types of repeating units(s) derived from one, or two or more types of monomer(s) represented by the following formula (a):

(a)

wherein $R^1$ is selected from hydrogen atom and $C_{1-3}$ alkyl;

$R^4$ and $R^5$ are independently selected from hydrogen atom and $C_{1-20}$ alkyl, in which the alkyl may be optionally substituted by one or more substituent(s) selected from hydroxy, $C_{1-6}$ alkoxy, and aryl, or $R^4$ and $R^5$ may be combined with the nitrogen atom to which they are attached to form a 4- to 8-membered nitrogen-containing hetero ring, in which the hetero ring may be optionally substituted by one or more substituent(s) selected from $C_{1-6}$ alkyl, $C_{1-6}$ alkoxy, nitro, halogen atom, $C_{1-10}$ alkylcarbonylamino, and arylcarbonylamino.

The cationic unit incorporated into the copolymer used in the fifth aspect of the present invention is a repeating structure derived from a monomer which contains an ionic functional group having one or more positive charges, and is one, or two or more types of repeating units(s) derived from one, or two or more types of monomer(s) represented by the following formula (b):

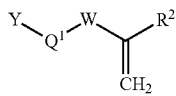

(b)

wherein $R^2$ is selected from hydrogen atom and $C_{1-3}$ alkyl;

W is aromatic ring or $-X^1-C(=O)-$ (in which $X^1$ is directly bonded to $Q^1$);

$X^1$ is O, S, or $N-R^{11}$;

$R^{11}$ is hydrogen atom, $C_{1-6}$ alkyl, or $-Q^1-Y$, in which the alkyl may be optionally substituted by one or more substituent(s) selected from hydroxy, halogen atom, $C_{1-6}$ alkoxy, $C_{1-6}$ alkylthio, $C_{1-6}$ alkylsulfinyl, and $C_{1-6}$ alkylsulfonyl;

$Q^1$ is independently selected from $C_{1-20}$ alkylene, $C_{3-20}$ alkenylene, or $C_{3-20}$ alkynylene, in which O, S, $-O-P(=O)(-OH)-O-$ or phenylene may be independently inserted into the alkylene at one or more position(s);

Y is independently an ionic functional group capable of having one or more positive charges, and is selected from $-N^+R^{21}R^{22}R^{23}X_e^-$, $-C(=NR^{41})-NR^{42}R^{43}$, and a group represented by the following formula:

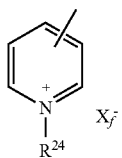

$X_e^-$ and $X_f^-$ are counter anions;

$R^{21}$, $R^{22}$, and $R^{23}$ are independently selected from $C_{1-10}$ alkyl and $C_{7-14}$ aralkyl, or $R^{21}$ and $R^{22}$ may be combined with the nitrogen atom to which they are attached to form a 5- to 7-membered nitrogen-containing hetero ring;

$R^{24}$ is $C_{1-10}$ alkyl or $C_{7-14}$ aralkyl; and $R^{41}$, $R^{42}$, and $R^{43}$ are independently selected from hydrogen atom and $C_{1-10}$ alkyl, or $R^{41}$ and $R^{42}$ may be combined with the nitrogen and carbon atoms to which they are attached to form a 5- to 7-membered hetero ring containing two nitrogen atoms, or $R^{42}$ and $R^{43}$ may be combined with the nitrogen atom to which they are attached to form a 5- to 7-membered nitrogen-containing hetero ring.

According to preferred embodiment of the present invention, the copolymer used in the fifth aspect of the present invention is a copolymer comprising repeating structures, each being derived from a monomer represented by formula (a), a monomer represented by formula (b), a monomer represented by formula (c), and a monomer represented by formula (d).

According to still more embodiment of the present invention, the copolymer used in the fifth aspect of the present invention is a copolymer comprising repeating units represented by formula (I), formula (II), formula (III), and formula (XIII):

(I)

(II)

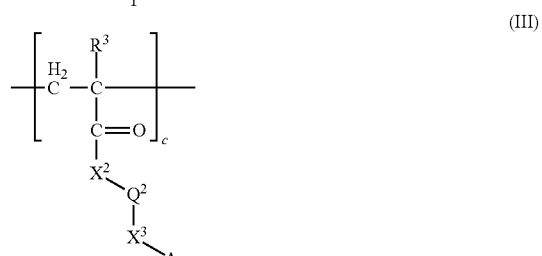

(III)

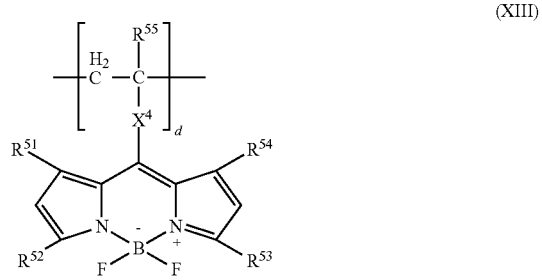

(XIII)

wherein $R^1$, $R^4$, and $R^5$ as well as $R^2$, Y, W, and $Q^1$ as well as $R^3$, $X^2$, $X^3$, $Q^2$, and Ar as well as $R^{55}$, $X^4$, $R^{51}$, $R^{52}$, $R^{53}$, and $R^{54}$ are as already defined above, and a, b, c, and d are numerals representing a ratio of each repeating unit in formula of more than 0. In this copolymer, the sum of a and b is 100, b is preferably 2 to 10, c is preferably 0.3 to 2, and d is preferably 0.03 to 1. This copolymer constitutes an aspect of the present invention as a substance itself.

According to preferred embodiment of the present invention, the copolymer comprises two or more types of thermoresponsive units. The type of thermoresponsive unit makes various temperature responsive range depending on the type of structure. In this embodiment, it is possible to set desired temperature responsive range by combining two or more types of thermoresponsive units in one copolymer. According to more preferred embodiment of the present invention, the copolymer comprises two or more types of thermoresponsive units represented by the formula (a). In an embodiment, two types of thermoresponsive units are used.

In the measurement at usual culture temperature of animal cells, for example, about 35° C., a combination of N-n-propylacrylamide (NNPAM) and N-isopropylacrylamide (NIPAM) is preferably used. When there is a need to measure the temperature region at 25° C. or lower for the purpose of monitoring fermentation of microorganisms such as yeast, a combination of N-tert-butylacrylamide (NT-BAM) and NNPAM is preferably used.

In formula (I), "a" represents the sum total of all thermoresponsive units, and represents the sum of ratios of the number of repeating units of all thermoresponsive units when two or more types of thermoresponsive units are used.

According to preferred embodiment of the present invention, in the above-mentioned copolymer, Ar is an aromatic carbocyclic group or an aromatic heterocyclic group selected from groups represented by the following formulas:

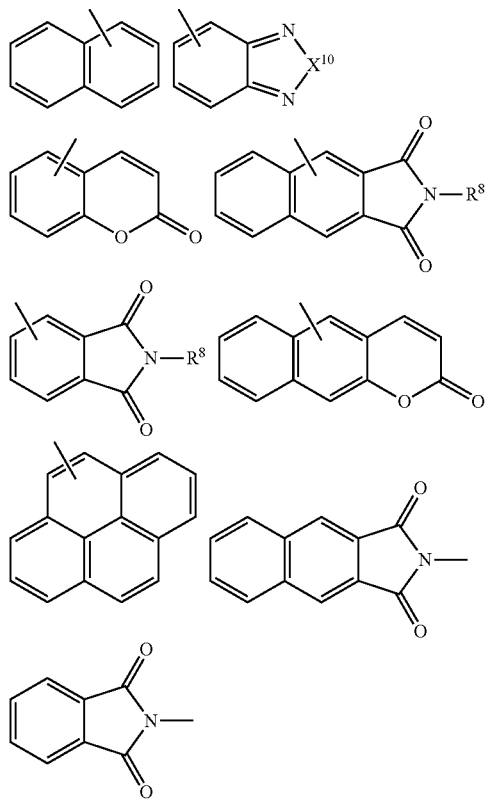

and these groups may be optionally substituted by one or more substituent(s) selected from halogen atom, $C_{1-6}$ alkyl, $C_{1-6}$ alkoxy, $C_{1-6}$ alkylthio, $C_{1-6}$ alkylsulfinyl, $C_{1-6}$ alkylsulfonyl, nitro, cyano, $C_{1-6}$ alkylcarbonyl, $C_{1-6}$ alkoxycarbonyl, carboxy, formyl, —$NR^6R^7$, and —$SO_2NR^{14}R^{15}$ on the ring (in which alkyl contained in the $C_{1-6}$ alkyl, $C_{1-6}$ alkoxy, $C_{1-6}$ alkylthio, $C_{1-6}$ alkylsulfinyl, $C_{1-6}$ alkylsulfonyl, $C_{1-6}$ alkylcarbonyl, and $C_{1-6}$ alkoxycarbonyl may be optionally substituted by one or more substituent(s) selected from halogen atom, $C_{1-6}$ alkoxy, hydroxy, amino, $C_{1-6}$ alkylamino, di($C_{1-6}$ alkyl)amino, aryl, and carboxy);

$X^{10}$ is selected from O, S, or Se;

$R^8$ is selected from hydrogen atom, $C_{1-10}$ alkyl, and aryl, the alkyl may be optionally substituted by one or more substituent(s) selected from halogen atom, $C_{1-6}$ alkoxy, hydroxy, amino, $C_{1-6}$ alkylamino, di($C_{1-6}$ alkyl)amino, aryl, and carboxy, and also the aryl may be optionally substituted by one or more substituent(s) selected from halogen atom, $C_{1-6}$ alkyl, $C_{1-6}$ alkoxy, and carboxy.

According to still more embodiment of the present invention, Ar is an aromatic carbocyclic group or aromatic heterocyclic group selected from groups represented by the following formulas:

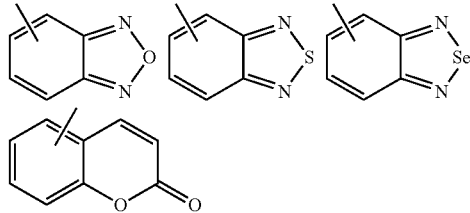

and these groups may be optionally substituted by one or more substituent(s) selected from halogen atom, $C_{1-6}$ alkyl, $C_{1-6}$ alkoxy, $C_{1-6}$ alkylthio, $C_{1-6}$ alkylsulfinyl, $C_{1-6}$ alkylsulfonyl, nitro, $C_{1-6}$ alkylcarbonylamino, arylcarbonylamino, cyano, formyl, $C_{1-6}$ alkylcarbonyl, $C_{1-6}$ alkoxycarbonyl, carboxy, and —$SO_2NR^{14}R^{15}$ on the ring.

Details of substituents in formulas in the fifth aspect of the present invention are as described with respect to the first to fourth aspects of the present invention.

As used herein, the copolymer is an assembly of polymer chains obtained by mixing monomers corresponding to the respective units, followed by polymerization reaction. The polymer represents a polymer chain in which monomer units are connected by bonding.

In formula (d) and formula (XIII), $R^{51}$, $R^{52}$, $R^{53}$, $R^{54}$, and $R^{55}$ are preferably selected from hydrogen atom and methyl.

In formula (d) and formula (XIII), preferred $X^4$ is, for example, direct bond, phenylene, -$Q^4$-O—C(=O)— (in which $Q^4$ is directly bonded to a boron dipyrromethene skeleton), or -$Q^4$-NH—C(=O)— (in which $Q^4$ is directly bonded to a boron dipyrromethene skeleton).

In formula (d) and formula (XIII), $Q^4$ is preferably phenylene.

According to particularly preferred embodiment of the present invention, $R^1$ is selected from hydrogen atom, methyl, and ethyl; $R^4$ is selected from n-propyl, isopropyl, and t-butyl, and $R^5$ is hydrogen atom; $R^2$ is selected from hydrogen atom, methyl and ethyl; W is aromatic ring or —$X^1$—C(=O)— (in which $X^1$ is directly bonded to $Q^1$); $X^1$ is O, S, or N—$R^{11}$; $R^{11}$ is hydrogen atom, $C_{1-6}$ alkyl, or -$Q^1$-Y; $Q^1$ is $C_{1-20}$ alkylene, in which O, S, —O—P(=O) (—OH)—O—, or phenylene may be independently inserted into the alkylene at one or more position(s); Y is independently an ionic functional group capable of having one or more positive charges, and is selected from —$N^+R^{21}R^{22}R^{23}X_e^-$, —C(=$NR^{41}$)—$NR^{42}R^{43}$, and a group represented by the following formula:

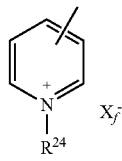

$X_e^-$ and $X_f^-$ are counter anions; $R^{21}$, $R^{22}$, and $R^{23}$ are independently $C_{1-10}$ alkyls, or $R^{21}$ and $R^{22}$ may be combined with the nitrogen atom to which they are attached to form a 5- to 7-membered nitrogen-containing hetero ring; $R^{24}$ is $C_{1-10}$ alkyl; $R^{41}$, $R^{42}$, and $R^{43}$ are independently selected from hydrogen atom and $C_{1-10}$ alkyl, or $R^{41}$ and $R^{42}$ may be combined with the nitrogen and carbon atoms to which they are attached to form a 5- to 7-membered hetero ring containing two nitrogen atoms, or $R^{42}$ and $R^{43}$ may be combined with the nitrogen atom to which they are attached to form a 5- to 7-membered nitrogen-containing hetero ring; $R^3$ is selected from hydrogen atom and $C_{1-3}$ alkyl; $X^2$ is O or N—$R^{12}$; $X^3$ is direct bond, O, N(—$R^{13}$), CON(—$R^{16}$), N(—$R^{16}$)CO, or N(—$R^{17}$)CON(—$R^{18}$); $Q^2$ is selected from $C_{1-20}$ alkylene, $C_{3-20}$ alkenylene, or $C_{3-20}$ alkynylene, in which O, S, or phenylene may be independently inserted into the alkylene at one or more position(s); Ar is an aromatic carbocyclic group or an aromatic heterocyclic group selected from groups represented by the following formulas:

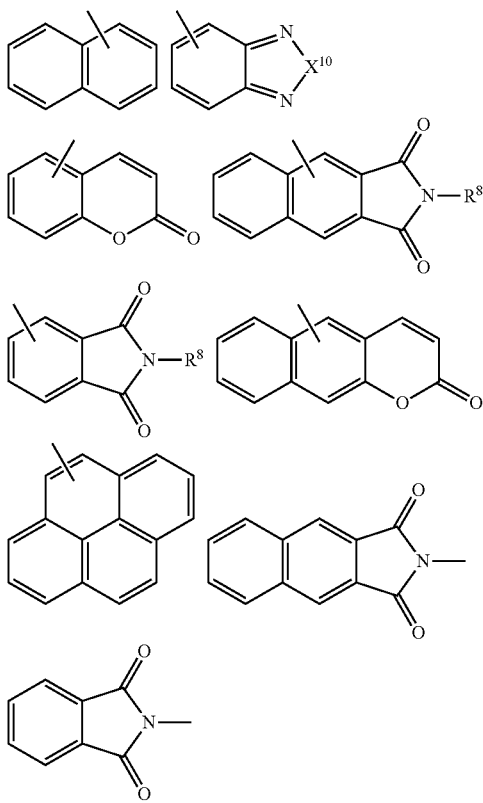

and these groups may be optionally substituted by one or more substituent(s) selected from halogen atom, $C_{1-6}$ alkoxy, nitro, cyano, —$NR^6R^7$, and —$SO_2NR^{14}R^{15}$ on the ring, and also may be optionally substituted by $C_{1-6}$ alkyl; $X^{10}$ is selected from O, S, or Se; $R^8$ is selected from hydrogen atom, $C_{1-10}$ alkyl, and aryl; $R^6$ and $R^7$ are independently selected from hydrogen atom, $C_{1-10}$ alkyl, aryl, $C_{1-10}$ alkylcarbonyl, arylcarbonyl, $C_{1-10}$ alkylsulfonyl, arylsulfonyl, and carbamoyl; or $R^6$ and $R^7$ may be combined with the nitrogen atom to which they are attached to form a 5- to 7-membered nitrogen-containing hetero ring, in which the hetero ring may be optionally substituted by one or more substituent(s) selected from $C_{1-6}$ alkyl, $C_{1-6}$ alkoxy, nitro, and halogen atom; $R^{12}$ is hydrogen atom, $C_{1-6}$ alkyl, or -$Q^2$-$X^3$—Ar, in which the alkyl may be optionally substituted by one or more substituent(s) selected from hydroxy and halogen atom; $R^{13}$ is hydrogen atom or $C_{1-6}$ alkyl, in which the alkyl may be optionally substituted by one or more substituent(s) selected from hydroxy and halogen atom; $R^{14}$ and $R^{15}$ are independently selected from hydrogen atom and $C_{1-6}$ alkyl; or $R^{14}$ and $R^{15}$ may be combined with the nitrogen atom to which they are attached to form a 5- to 7-membered nitrogen-containing hetero ring; $R^{16}$, $R^{17}$, and $R^{18}$ are independently selected from hydrogen atom and $C_{1-6}$ alkyl, in which the alkyl may be optionally substituted by one or more substituent(s) selected from hydroxy and halogen atom; $R^{51}$, $R^{52}$, $R^{53}$, $R^{54}$, and $R^{55}$ are independently selected from hydrogen atom and methyl group; $X^4$ is direct bond, phenylene, -$Q^4$-O—C(=O)— (in which $Q^4$ is directly bonded to a boron dipyrromethene skeleton), or -$Q^4$-NH—C(=O)— (in which $Q^4$ is directly bonded to a boron dipyrromethene skeleton) and $Q^4$ is phenylene.

In formula (I), formula (II), formula (III), and formula (XIII), a, b, c, and d are numerals representing a ratio of each repeating unit in formula of more than 0 and is not particularly limited. For example, when a+b=100, b is, for example, 1 or more, preferably 2 or more, more preferably 2.5 or more, and still more preferably 3 or more and, for example, 15 or less, and preferably 10 or less. When a+b=100, b is, for example, 1 to 15, preferably 2 to 10, and more preferably 3 to 10. "c" is a proportion based on the total amount of a+b (namely, 100), and c is 0.05 to 10, specifically 0.1 to 5, preferably 0.2 to 2, and more preferably 0.3 to 1.5. "d" is a proportion based on the total amount of a+b (namely, 100), and d is 0.01 to 5, specifically 0.02 to 2, preferably 0.02 to 1, and more preferably 0.03 to 1. c/d representing a ratio of c to d is not particularly limited, preferably 0.1 to 30, more preferably 1 to 20, and still more preferably 3 to 10. As mentioned above, a is the sum total of thermoresponsive units and, for example, when two types of thermoresponsive units are used, a ratio of the thermoresponsive unit becomes p:a–p using certain numeral p. For example, when a copolymer is produced so that b becomes 2.5 (a+b=100), and also two types of thermoresponsive units (for example, N-n-propylacrylamide and N-isopropylacrylamide) are used in combination, a is 97.5, N-n- and a ratio of propylacrylamide to N-isopropylacrylamide is represented by p:97.5–p. The weight average molecular weight of the copolymer of the present invention is not particularly limited, and is, for example, 1,000 to 100,000, and preferably 5,000 to 50,000.

Depending on the molecular weight of a polymer of the present invention and the amount of a monomer of the fluorescent unit used, two fluorescent units are not always introduced into one polymer. When this polymer is used as a temperature-sensitive probe, if the combination of a usual excitation intensity and detection sensitivity is used, the polymer is used at some higher concentration of >0.001% (w/v) in a solution and is used intracellularly under the condition that fluorescence derived from the fluorescent unit is adequately and intracellularly observed; thus, a copolymer at a relatively higher concentration, i.e., a concentration of >0.001% (w/v) which is similar to that when used in a solution, exists intracellularly. In other words, even if two fluorescent units are divided into two polymers, two separate polymers comprising two fluorescent units are placed in an almost same temperature environment unless the environment is a special environment in which there is only one polymer molecule in the observational field or the measurement field, thus, each fluorescent unit shows a fluorescence intensity similar to that when two fluorescent units are comprised in one polymer. Therefore, a copolymer of the present invention is not limited to the case where two fluorescent units are comprised in the same polymer molecule.

A copolymer according to the fifth aspect of the present invention very quickly responds to ambient temperature change, and the structural change is about several milliseconds. In other words, a temperature-sensitive fluorescent probe according to the fifth aspect of the present invention quickly responds to intracellular temperature change to change the fluorescence intensity; thus, when an intracellular temperature distribution is visualized with a microscope, etc., the intracellular temperature in each intracellular microspace can be determined from its ratio of fluorescence intensity.

The copolymer according to the present invention can be synthesized based on common knowledge in the technical field of polymer synthesis and, for example, it can be obtained as a random copolymer by radical polymerization. Examples of usable radical initiator in that case include, but are not limited to, persulfates such as ammonium persulfate, sodium persulfate, and potassium persulfate; and azo compounds such as 2,2'-azobis(2-methylpropionamidine) dihydrochloride, 2,2'-azobis[2-(2-imidazolin-2-yl)propane] dihydrochloride, and 4,4'-azobis(4-cyanovaleric acid).

The amount of the reaction initiator used may be 0.01 mol % or more based on the amount of the monomer used, and an appropriate amount can be selected as long as the concentration enables proceeding of radical synthesis. For example, it is possible to use 0.1 mol % or more, and preferably 1 mol % or more of the reaction initiator.

Examples of the reaction solvent used for polymerization include, but are not limited to, acetonitrile, dioxane, dimethylformamide, methanol, and the like. The radical polymerization is not particularly limited and can be performed, for example, at the reaction temperature of 0 to 100° C., preferably 50 to 70° C., for 1 to 48 hours, and preferably 2 to 16 hours as the reaction time.

In order to measure the temperature without being influenced by the pH and salt concentration in a solution containing the copolymer of the present invention, a cationic functional group contained in the copolymer preferably maintain ionicity within a wide range of the pH. The pH in a cell is 2 to 9 only for the purpose of measuring an intracellular temperature, and is about 4 to 8 in a usual state for common animal, plant, and microbial cells. The functional group preferably controls cationicity at the pH. From such a point of view, Y is preferably —$N^+R^{21}R^{22}R^{23}X_e^-$.

A "cell" in the present invention includes both of usually categorized prokaryotic cells and eukaryotic cells, and does not particularly depend on its biological species. For example, prokaryotic cells are divided into eubacteria and archaebacteria, and eubacteria are especially divided into Gram-positive bacteria such as Actinobacteria and Gram-negative bacteria such as Proteobacteria; the applicable range of a copolymer is not limited by the thickness of a peptidoglycan layer, etc. Eukaryotic cells mainly include cells belonging to eukaryotes (protists, fungus, plants, and animals). For example, yeast, which is usually used in molecular biology research, etc. and also used in industry, belongs to fungus. A temperature-sensitive probe of the present invention is suitably used in both non-adherent cells and adherent cells.

When a copolymer according to the fifth aspect of the present invention is introduced into a cell, it is desirable to replace its solution with a solution with a low ionic strength (solvent). Such solvent includes, for example, water (preferably, pure water), an aqueous sorbitol solution, and a glucose solution. Depending on the type of a cell, other solvents include a solution in which a 0.45 mM calcium chloride is added to these glucose solutions.

The concentration of a copolymer when the copolymer is introduced into a cell in accordance with the present invention, for example, can be prepared so that the final concentration of the copolymer is 0.001 to 1% (w/v), preferably 0.01 to 0.5% (w/v), and be mixed with a fungus body. This applies not only to a microbial body, etc. but also to adherent cells, etc.

Change in the fluorescence intensity due to the thermoresponsitivity of a copolymer used in the fifth aspect of the present invention can be measured by a usual fluorescence intensity measurement method. There is no particular limitation on excitation wavelength in measurement and fluorescence wavelength to be measured, and, for example, the maximum excitation wavelength when the excitation spectrum of a measurement sample is measured or a wavelength near the maximum wavelength can be used. There is also no particular limitation on fluorescence wavelength to be measured, and, for example, the maximum fluorescence wavelength when the fluorescence spectrum of a measurement sample is measured at a certain temperature or a wavelength near the maximum wavelength can be used.

In the present invention, it is desirable to measure the fluorescence intensities of two certain independent fluorescence wavelengths to calculate a ratio of them, and convert the ratio of fluorescence intensity into temperature. With this method, it is possible to exclude the possibility that the fluorescence intensity emitted from a copolymer is due to the concentration of the copolymer in the micro-space or excitation laser intensity, and to make a one-to-one correspondence between temperature and the ratio of fluorescence intensity obtained from an experiment. As a result, it is possible not only to compare temperatures of the same cell but also to compare intracellular temperatures of other cells under the same condition. For example, by measuring differences in individual cell temperature in a yeast population, the physiological state of each yeast cell can be grasped.

There is no particular limitation on a calculation method for ratio of fluorescence intensity, and the ratio can be calculated from the fluorescence intensities of two regions comprising different wavelengths. For example, one region is set at a wavelength region of about 20 nm comprising a wavelength showing the maximum intensity of the fluorescence generated from the first fluorescent unit and the integrated value of its fluorescence intensity is defined as S1; the other region is set at a wavelength region of about 20 nm comprising a wavelength showing the maximum intensity of the fluorescence generated from the second fluorescent unit and the integrated value of its fluorescence intensity is defined as S2; and S1/S2 may be defined as a ratio of fluorescence intensity. Furthermore, the regions of S1 and S2 may be same width or different width. For example, if the fluorescence intensity shows a value enough to ignore a noise, S1 comprises a wavelength region with a width of 20 nm, while S2 may be a single wavelength with a width of 1 nm. There is no particular limitation on the selection criteria of wavelength; considering the fluorescence intensity obtained, it is desirable to select a wavelength near the wavelength showing the maximum fluorescence intensity when the excitation spectrum of a monomer giving each fluorescent unit comprised in a temperature-sensitive probe (e.g., fluorescent monomer shown in formula (c) or formula (d)) in water or a polar solvent similar to water at room temperature (about 25° C.) is measured.

When the temperature is calculated from the ratio of fluorescence intensity obtained from an experiment, a calibration curve set by your own can be used. Specifically, there is no limitation on the condition under which a calibration curve to be used is measured, and, for example, a curve in which change in the fluorescence intensity due to the thermoresponsitivity of a copolymer in a potassium chloride solution imitating an intracellular space are plotted, a curve in which change in the fluorescence intensity due to the thermoresponsitivity by subjecting a cell population into which a copolymer is introduced to a spectrofluorometer are plotted, or a curve in which mean change in the fluorescence intensity due to the thermoresponsitivity in a plurality of cells by subjecting a cell population into which a copolymer is introduced to a fluorescence microscope are plotted, etc. can be used. More specifically, when change in the fluorescence intensity is plotted by performing a thermoresponsivity test with a cell population into which a copolymer is introduced, there is a method for measuring the fluorescence intensity under the condition in which the metabolic activity of a cell is not actively performed, for example, a cell is suspended in water or in a buffer containing a compound which cannot be assimilated, the cell is held at a specific temperature for a certain period, and the external temperature and the intracellular temperature seem to be in an equilibrium.

In order to perform the methods described above, all necessary reagent, etc. can be used as a kit. Therefore, according to other aspects of the present invention, there is provided a kit for the measurement a temperature, using the above mentioned methods, the kit comprising a temperature-sensitive probe of the present invention or a copolymer of the present invention. This reagent kit for the measurement of a temperature can be suitably used for the measurement of a temperature in a micro-space, especially intracellular temperature measurement. The reagent kit can be used in research fields such as medicine, biology, and bioengineering, and medical fields such as diagnosis and treatment.

Methods and a kit for the measurement of a temperature of the present invention can be applied to various fields of research and development. For example, in the bioengineering field, it is expected that culture conditions can be considered efficiently in fermentative production of useful substances using microorganisms by adding intracellular temperature, which had been difficult to be accurately measured, to analysis parameters.

Methods and a kit for the measurement of a temperature of the present invention can be applied to various medical uses. For example, using a temperature-sensitive probe according to the present invention for some tissues of patients enables discrimination between cancer cells with more heat production and normal cells without such production. Furthermore, as an application, this probe can be used for development of more efficient thermotherapy, etc. Alternatively, after a temperature-sensitive probe according to the present invention is introduced into a brown adipocyte with more heat production, change in temperature due to addition of various materials to the cell are measured, enabling the screening of materials which activate a brown adipocyte.

Methods and a kit for the measurement of a temperature of the present invention can also be applied to elucidation of various physiological phenomena. For example, by investigating how a TRP channel, a receptor which senses in vitro temperature and causes biological reactions, is associated with intracellular temperature, the TRP channel may be activated by an approach different from conventional one. By investigating the relationship between intracellular temperature distribution and intracellular or extracellular biological reactions, the effects of local temperature distribution on biological reactions can be evaluated, and cells can be controlled by local heating with an infrared laser, etc.

A temperature measurement method and a cell introduction method of a temperature-sensitive probe according to the present invention can be performed either in vitro or in vivo. In one embodiment, these methods are performed in vitro.

EXAMPLES

The present invention will be described in more detail below by way of Examples, but the present invention is not limited to these Examples.

A. Study on Temperature-Sensitive Probe Introducible into Cell by Mixing with Cell in Solvent
Reagent and Data Measurement After purifying by recrystallization with methanol, α,α'-azobisisobutyronitrile was used. Regarding other reagents, purchases were used without being purified.

Using a BRUKER AVANCE 400 spectrometer (400 MHz), $^1$H-NMR was measured and chemical shift was indicated by ppm. Using a JASCO GPC system (JASCO PU-2080 pump, JASCO RI-2031 differential refractometer, JASCO CO-2060 column oven, Shodex GPC KD-806M column), the number average molecular weight and weight average molecular weight were calculated by using a calibration curve obtained from a polystyrene standard sample. In silica gel column chromatography, Kanto Chemical silica gel 60N (40-50 μm) was used. In the measurement of an absorbance, a JASCO V-550 ultraviolet visible light spectrophotometer was used.

Example 1: Synthesis of N-{2-[(7-N,N-dimethyl-aminosulfonyl)-2,1,3-benzoxadiazol-4-yl](methyl)amino}ethyl-N-methylacrylamide

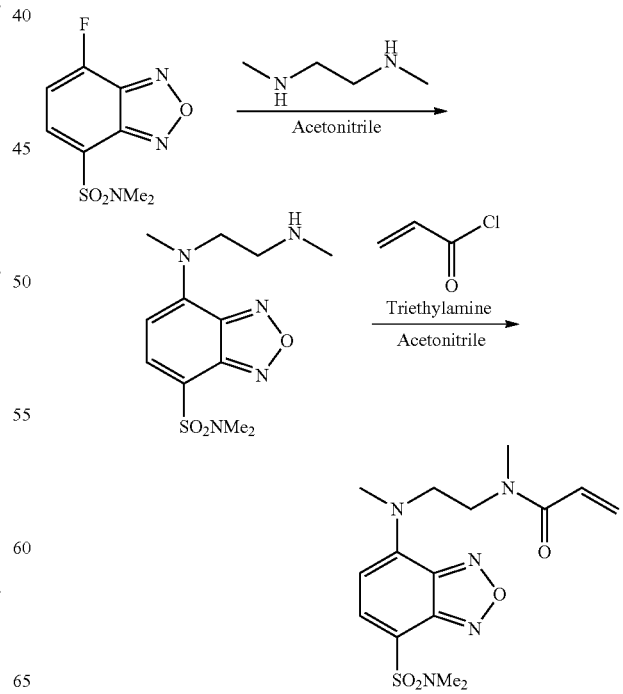

4-N,N-dimethylaminosulfonyl-7-fluoro-2,1,3-benzoxadiazole (94 mg) was dissolved in acetonitrile (5 ml), and this solution was added to N,N'-dimethylethylenediamine (1.29 ml), followed by stirring at room temperature for 15 minutes. After completion of the reaction, the reaction solution was evaporated to dryness under reduced pressure, and then purified by silica gel column chromatography (using dichloromethane:methanol=10:1→5:1 as a developing solvent) to obtain N,N-dimethyl-7-[methyl{2-(methylamino)ethyl}amino]-2,1,3-benzoxadiazole-4-sulfonamide as an orange liquid (113 mg, 94%).

$^1$H-NMR (CDCl$_3$) δ7.87 (1H, d, J=8.4 Hz), 6.08 (1H, d, J=8.4 Hz), 4.15 (2H, t, J=6.6 Hz), 3.35 (3H, s), 2.94 (2H, t, J=6.8 Hz), 2.87 (6H, s), 2.48 (3H, s).

N,N-dimethyl-7-[methyl{2-(methylamino)ethyl}amino]-2,1,3-benzoxadiazole-4-sulfonamide (113 mg) was dissolved in acetonitrile (10 ml), and triethylamine (50.2 μL, 1 eq) and acrylic acid chloride (38.0 μL, 1.3 eq) were added at 0° C., followed by stirring at 0° C. for 1 hour. To the reaction solution, Na$_2$CO$_3$ (1 g) was added, followed by filtration, evaporation to dryness under reduced pressure and further purification by silica gel column chromatography (using ethyl acetate-n-hexane=3:1→4:1 as a developing solvent) to obtain the titled compound as an orange crystal (106.1 mg, 80%).

$^1$H-NMR (CDCl$_3$) δ7.88 (1H, d, J=8.4 Hz), 6.48 (1H, dd, J=16.8 Hz, 10.4 Hz), 6.28 (1H, d, J=16.8 Hz), 6.14 (1H, d, J=8.4 Hz), 5.68 (1H, d, J=10.4 Hz), 4.27 (2H, t, J=7.00 Hz), 3.74 (2H, t, J=6.8 Hz), 3.29, 3.12 (3H, s), 2.88 (6H, s).

Example 2: Synthesis of N-n-propylacrylamide

To benzene (125 mL), N-n-propylamine (8.2 mL) and triethylamine (16.7 mL, 1.2 eq) were added. After stirring well in an ice bath using a stirrer, acrylic acid chloride (9.7 mL, 1.2 eq) was added by 3 mL every 10 minutes, and then the temperature was returned to room temperature. The reaction solution was filtered and isolated with 0.1N hydrochloric acid. After the benzene fraction of the upper layer was extracted and anhydrous sodium sulfate was added, the solution was evaporated to dryness under reduced pressure and subjected to first purification by silica gel column chromatography (using dichloromethane-methanol=50:1 as a developing solvent). The fraction containing the objective compound was collected again, evaporated to dryness under reduced pressure, and then subjected to second purification by silica gel column chromatography (using ethyl acetate-hexane=1:2 as a developing solvent) to obtain the titled compound as a colorless transparent liquid (3.74 g, 33%).

$^1$H-NMR (CDCl$_3$) δ6.28 (1H, dd, J=16.8 Hz, 1.6 Hz), 6.08 (1H, dd, J=16.8 Hz, 10.4 Hz), 5.64 (1H, dd, J=10.4 Hz, 1.6 Hz), 5.55 (1H, br), 3.30 (2H, m), 1.58 (2H, m), 0.95 (3H, t, J=7.6 Hz).

Example 3: Production of N-n-propylacrylamide/3-sulfopropylacrylate/N-{2-[(7-N,N-dimethylaminosulfonyl)-2,1,3-benzoxadiazol-4-yl](methyl)amino}ethyl-N-methylacrylamide Copolymer

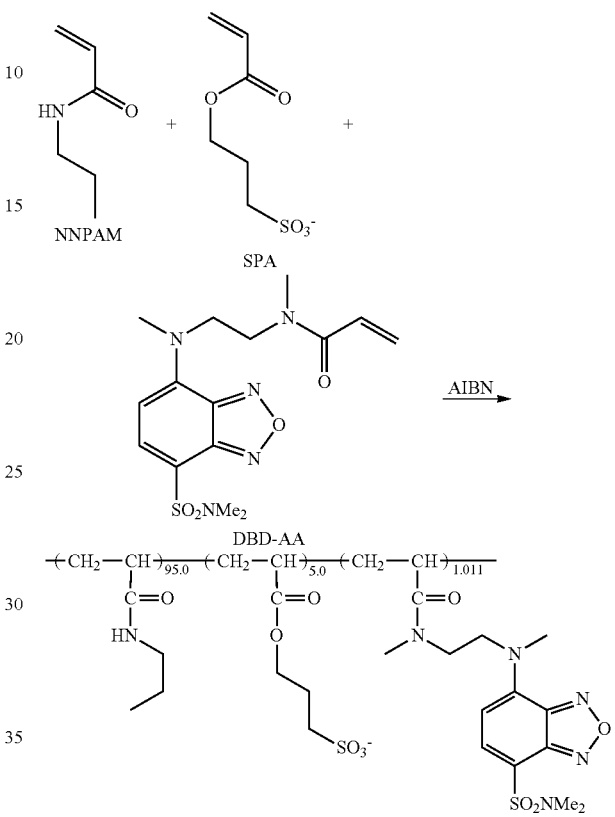

N-n-propylacrylamide (269 mg, 2.375 mmol, hereinafter also referred to as "NNPAM"), 3-sulfopropylacrylate potassium salt (29.0 mg, 125 μmol, hereinafter also referred to as "SPA potassium salt"), DBD-AA (9.13 mg, 25 μmol), and AIBN (4.13 mg, 25 μmol) were dissolved in DMF (5 ml), and then dissolved oxygen was removed by passing through a nitrogen-argon gas for 30 minutes. Thereafter, the mixture was reacted at 60° C. for 16.5 hours and DMF was partially distilled off from the reaction solution under reduced pressure, and then the solution was poured into diethylether (200 ml). The crystal thus obtained was collected by filtration, dried under reduced pressure and then dissolved in 10 ml of pure water. Using a Visking tube having a diameter of 28.6 mm (cellulose tube for dialysis), the solution was purified by dialyzing well with 1,000 ml of a dialysis outer liquid. The purified product was freeze-dried to obtain the titled copolymer as a pale yellow powder (161 mg, 52%).

The number average molecular weight was 17,606 and the weight average molecular weight was 39,184, and a composition ratio of each unit in a copolymer was as follows: NNPAM:SPA:DBD-AA=95.0:5.0:1.011. The proportions of a NNPAM unit and a SPA unit in a copolymer was calculated from an integrated value in the $^1$H-NMR measurement, and the proportion of a DBD-AA unit was calculated by comparing an absorbance in methanol with 4-N,N-(dimethylamino)-7-N,N-dimethylaminosulfonyl-2,1,3-benzoxadiazole.

Example 4: Production of N-n-propylacrylamide/(3-acrylamidepropyl)trimethylammonium/N-{2-[(7-N,N-dimethylaminosulfonyl)-2,1,3-benzoxadiazol-4-yl](methyl)amino}ethyl-N-methylacrylamide copolymer

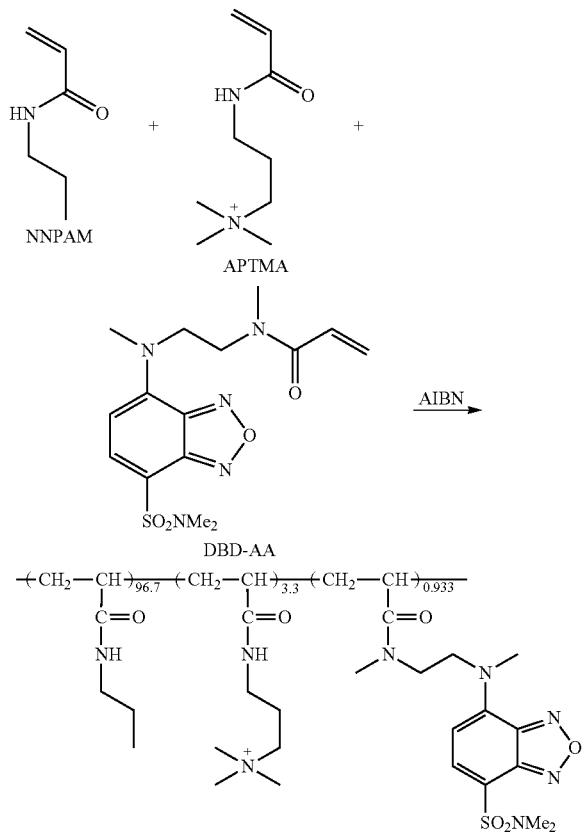

NNPAM (275 mg, 2.44 mmol), (3-acrylamidepropyl)trimethylammonium chloride (17.5 mg, 62.5 μmol, hereinafter also referred to as "APTMA chloride"), DBD-AA (9.13 mg, 25 μmol), and AIBN (4.05 mg, 25 μmol) were dissolved in DMF (5 ml) and then dissolved oxygen was removed by passing through an argon gas for 30 minutes. Thereafter, the mixture was reacted at 60° C. for 19 hours and DMF was partially distilled off from the reaction solution under reduced pressure, and then the solution was poured into diethylether (200 ml). The crystal thus obtained was collected by filtration, dried under reduced pressure and then dissolved in 10 ml of pure water. Using a Visking tube having a diameter of 28.6 mm (cellulose tube for dialysis), the solution was purified by dialyzing well with 1,000 ml of a dialysis outer liquid. The purified product was freeze-dried to obtain the titled copolymer as a pale yellow powder (200 mg, 66%).

The number average molecular weight was 10,061 and the weight average molecular weight was 21,637, and a composition ratio of each unit in a copolymer was as follows: NNPAM:APTMA:DBD-AA=96.7:3.3:0.933. The proportions of a NNPAM unit and an APTMA unit in a copolymer was calculated from an integrated value in the $^1$H-NMR measurement, and the proportion of a DBD-AA unit was calculated by comparing an absorbance in methanol with 4-N,N-(dimethylamino)-7-N,N-dimethylaminosulfonyl-2,1,3-benzoxadiazole.

Example 5: Production of N-n-propylacrylamide/(3-acrylamidepropyl)trimethylammonium/N-{2-[(7-N,N-dimethylaminosulfonyl)-2,1,3-benzoxadiazol-4-yl](methyl)amino}ethyl-N-methylacrylamide copolymer In the same manner as in Example 4, synthesis was performed. Using NNPAM (270 mg, 2.38 mmol), APTMA (34.4 mg, 125 μmol), DBD-AA (9.18 mg, 25 μmol), and AIBN (4.09 mg, 25 μmol), the titled copolymer was obtained as a pale yellow powder (229 mg, 74%).

The number average molecular weight was 8,166 and the weight average molecular weight was 15,213, and a composition ratio of each unit in a copolymer was as follows: NNPAM:APTMA:DBD-AA=94.3:5.7:0.888. The calculation method is as shown in Example 4.

Example 6: Production of N-n-propylacrylamide/(3-acrylamidepropyl)trimethylammonium/N-{2-[(7-N,N-dimethylaminosulfonyl)-2,1,3-benzoxadiazol-4-yl](methyl)amino}ethyl-N-methylacrylamide copolymer In the same manner as in Example 4, synthesis was performed. Using NNPAM (262 mg, 2.31 mmol), APTMA (51.9 mg, 188 μmol), DBD-AA (9.22 mg, 25 μmol), and AIBN (4.15 mg, 25 μmol), the titled copolymer was obtained as a pale yellow powder (238 mg, 76%).

The number average molecular weight was 6,579 and the weight average molecular weight was 11,603, and a composition ratio of each unit in a copolymer was as follows: NNPAM:APTMA:DBD-AA=90.9:9.1:0.896. The calculation method is as shown in Example 4.

Example 7: Production of N-n-propylacrylamide/(3-acrylamidepropyl)trimethylammonium/N-{2-[(7-N,N-dimethylaminosulfonyl)-2,1,3-benzoxadiazol-4-yl](methyl)amino}ethyl-N-methylacrylamide copolymer In the same manner as in Example 4, synthesis was performed. Using NNPAM (212 mg, 1.88 mmol), APTMA (173.6 mg, 625 μmol), DBD-AA (9.18 mg, 25 μmol), and AIBN (4.18 mg, 25 μmol), the titled copolymer was obtained as a pale yellow powder (251 mg, 70%).

The number average molecular weight was 4,043 and the weight average molecular weight was 5,459, and a composition ratio of each unit in a copolymer was as follows: NNPAM:APTMA:DBD-AA=74.4:25.6:0.902. The proportions of a NNPAM unit and an APTMA unit in a copolymer was calculated from an integrated value in the $^1$H-NMR measurement, and the proportion of a DBD-AA unit was calculated by comparing an absorbance in methanol with 4-N,N-(dimethylamino)-7-N,N-dimethylaminosulfonyl-2,1,3-benzoxadiazole.

Example 8: Production of dimethylacrylamide/(3-acrylamidepropyl)trimethylammonium/N-{2-[(7-N,N-dimethylaminosulfonyl)-2,1,3-benzoxadiazol-4-yl](methyl)amino}ethyl-N-methylacrylamide copolymer Dimethylacrylamide (229 mg, 2.31 mmol, hereinafter also referred to as "DMAM"), APTMA (52.0 mg, 188

μmol), DBD-AA (9.18 mg, 25 μmol), and AIBN (4.07 mg, 25 μmol) were dissolved in DMF (5 ml), and then dissolved oxygen was removed by passing through an argon gas for 30 minutes. Thereafter, the mixture was reacted at 60° C. for 16 hours and DMF was partially distilled off from the reaction solution under reduced pressure, and then the solution was poured into diethylether (200 ml). The crystal thus obtained was collected by filtration, dried under reduced pressure and then dissolved in 10 ml of pure water. Using a Visking tube having a diameter of 28.6 mm (cellulose tube for dialysis), the solution was purified by dialyzing well with 1,000 ml of a dialysis outer liquid. The purified product was freeze-dried to obtain the titled copolymer as a pale yellow powder (185 mg, 66%).

The number average molecular weight was 5,633 and the weight average molecular weight was 8,468, and a composition ratio of each unit in a copolymer was as follows: DMAM:APTMA:DBD-AA=79.6:20.4:0.831. The proportions of a DMAM unit and an APTMA unit in a copolymer was calculated from an integrated value in the $^1$H-NMR measurement, and the proportion of a DBD-AA unit was calculated by comparing an absorbance in methanol with 4-N,N-(dimethylamino)-7-N,N-dimethylaminosulfonyl-2,1,3-benzoxadiazole.

Example 9: Production of N-n-propylacrylamide/N-{2-[(7-N,N-dimethylaminosulfonyl)-2,1,3-benzoxadiazol-4-yl](methyl)amino}ethyl-N-methylacrylamide Copolymer

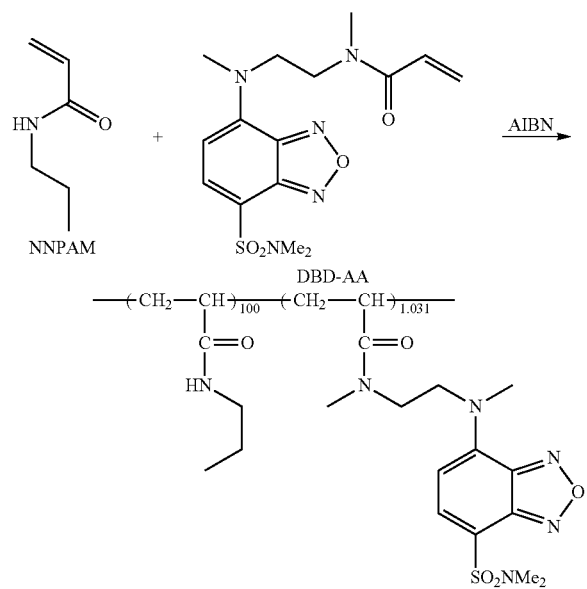

NNPAM (142 mg, 1.25 mmol), AIBN (2.02 mg, 12.5 μmol), and DBD-AA (4.62 mg, 12.5 μmol) were dissolved in DMF (5 ml), and then dissolved oxygen was removed by passing through a nitrogen gas for 30 minutes. Thereafter, the mixture was reacted at 60° C. for 8 hours and then the reaction solution was poured into 200 ml of diethylether. The crystal thus obtained was collected by filtration and then purified by a reprecipitation operation (acetone (2.5 ml)-diethylether (200 ml)) to obtain the titled copolymer as a pale yellow powder (87 mg, 58%).

The number average molecular weight was 36,033 and the weight average molecular weight was 92,042, and a composition ratio of each unit in a copolymer was as follows: NNPAM:DBD-AA=100:1.031. The proportion of a DBD-AA unit was calculated by comparing an absorbance in methanol with 4-N,N-(dimethylamino)-7-N,N-dimethylaminosulfonyl-2,1,3-benzoxadiazole.

Example 10: Production of N-n-propylacrylamide/vinylbenzyltrimethylammonium/N-{2-[(7-N,N-dimethylaminosulfonyl)-2,1,3-benzoxadiazol-4-yl](methyl)amino}ethyl-N-methylacrylamide copolymer

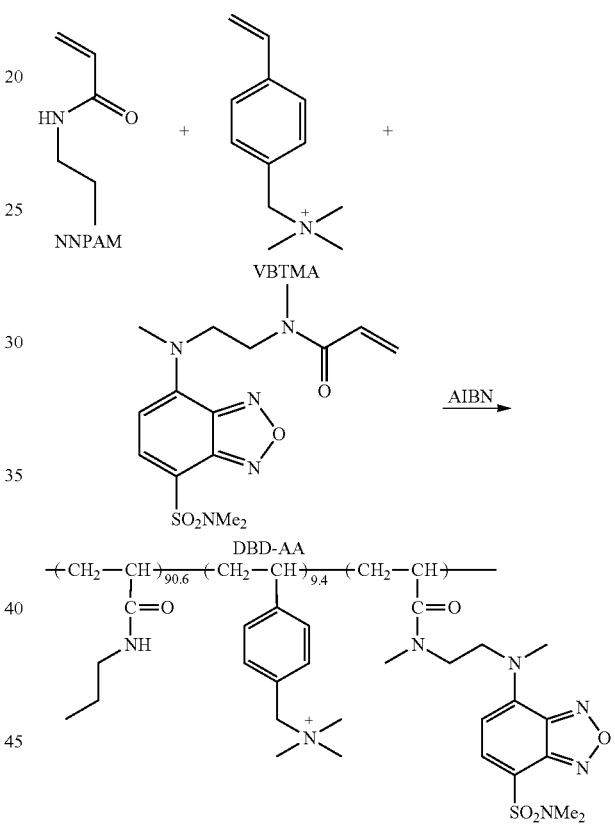

NNPAM (268.7 mg, 2.375 mmol), vinylbenzyltrimethylammonium chloride (23.2 mg, 125 μmol, hereinafter also referred to as "VBTMA chloride"), DBD-AA (1.84 mg, 5 μmol), and AIBN (4.05 mg, 25 μmol) were dissolved in DMF (5 ml), and then dissolved oxygen was removed by passing through an argon gas for 30 minutes. Thereafter, the mixture was reacted at 60° C. for 14 hours and then the solution was poured into diethylether (200 ml). The crystal thus obtained was collected by filtration, dried under reduced pressure and then dissolved in 10 ml of pure water. Using a Visking tube having a diameter of 28.6 mm (cellulose tube for dialysis), the solution was purified by dialyzing well with 1,000 ml of a dialysis outer liquid. The purified product was freeze-dried to obtain the titled copolymer as a pale yellow powder (41 mg, 14%).

A composition ratio of each unit in a copolymer was as follows: NNPAM:VBTMA=90.6:9.4. The proportions of a NNPAM unit and a VBTMA unit in a copolymer were calculated from an integrated value in the $^1$H-NMR measurement.

Example 11: Production of N-n-propylacrylamide/N-isopropylacrylamide/(3-acrylamidepropyl)trimethylammonium/N-{2-[(7-N,N-dimethylaminosulfonyl)-2,1,3-benzoxadiazol-4-yl](methyl)amino}ethyl-N-methylacrylamide Copolymer In the same manner as in Example 4, synthesis was performed. Specifically, NNPAM (137.5 mg, 1.22 mmol), N-isopropylacrylamide (137.5 mg, 1.22 mmol, hereinafter also referred to as "NIPAM") (3-acrylamidepropyl)trimethylammonium chloride (17.5 mg, 62.5 μmol, hereinafter also referred to as "APTMA chloride"), DBD-AA (9.13 mg, 25 μmol), and AIBN (4.05 mg, 25 μmol) were dissolved in DMF (5 ml), and then dissolved oxygen was removed by passing through an argon gas for 30 minutes. Thereafter, the mixture was reacted at 60° C. for 19 hours and DMF was partially distilled off under reduced pressure from the reaction solution, and then the solution was poured into diethylether (200 ml). The crystal thus obtained was collected by filtration, dried under reduced pressure and then dissolved in 10 ml of pure water. Using a Visking tube having a diameter of 28.6 mm (cellulose tube for dialysis), the solution was purified by dialyzing well with 1,000 ml of a dialysis outer liquid. The purified product was freeze-dried to obtain the titled copolymer as a pale yellow powder (154 mg, 50%).

The number average molecular weight was 19,730 and the weight average molecular weight was 10,386, and a composition ratio of each unit in a copolymer was as follows: NNPAM:NIPAM:APTMA:DBD-AA=49.8:46.9:3.3:0.805. The proportions of a NNPAM unit, a NIPAM unit, and an APTMA unit in a copolymer was calculated from an integrated value in the $^1$H-NMR measurement, and the proportion of a DBD-AA unit was calculated by comparing an absorbance in methanol with 4-N,N-(dimethylamino)-7-N,N-dimethylaminosulfonyl-2,1,3-benzoxadiazole.

Example 12: Production of N-isopropylacrylamide/(3-acrylamidepropyl)trimethylammonium/N-{2-[(7-N,N-dimethylaminosulfonyl)-2,1,3-benzoxadiazol-4-yl](methyl)amino}ethyl-N-methylacrylamide copolymer NIPAM (275 mg, 2.44 mmol), (3-acrylamidepropyl)trimethylammonium chloride (17.5 mg, 62.5 μmol, hereinafter also referred to as "APTMA chloride"), DBD-AA (9.13 mg, 25 μmol), and AIBN (4.05 mg, 25 μmol) were dissolved in DMF (5 ml), and then dissolved oxygen was removed by passing through an argon gas for 30 minutes. Thereafter, the mixture was reacted at 60° C. for 19 hours and DMF was partially distilled off from the reaction solution under reduced pressure, and then the solution was poured into diethylether (200 ml). The crystal thus obtained was collected by filtration, dried under reduced pressure and then dissolved in 10 ml of pure water. Using a Visking tube having a diameter of 28.6 mm (cellulose tube for dialysis), the solution was purified by dialyzing well with 1,000 ml of a dialysis outer liquid. The purified product was freeze-dried to obtain the titled copolymer as a pale yellow powder (139 mg, 45%).

The number average molecular weight was 23,312 and the weight average molecular weight was 11,737, and a composition ratio of each unit in a copolymer was as follows: NIPAM:APTMA:DBD-AA=96.4:3.6:0.814. The proportions of a NIPAM unit and an APTMA unit in a copolymer was calculated from an integrated value in the $^1$H-NMR measurement, and the proportion of a DBD-AA unit was calculated by comparing an absorbance in methanol with 4-N,N-(dimethylamino)-7-N,N-dimethylaminosulfonyl-2,1,3-benzoxadiazole.

The copolymers produced in Examples 3, 4, 5, 6, 7, 8, 9, 10, 11, and 12 are hereinafter referred to as compounds 1, 2, 3, 4, 5, 6, 7, 8, 9, and 10, respectively. Features of substances of compounds 1 to 10 are summarized in the following table.

|  | Thermoresponsive unit (a) | Ionic unit (b) | a:b (before reaction) | a:b (after reaction) |
|---|---|---|---|---|
| Compound 1 | NNPAM | SPA | 95.0:5.0 | 95.0:5.0 |
| Compound 2 | NNPAM | APTMA | 97.5:2.5 | 96.7:3.3 |
| Compound 3 | NNPAM | APTMA | 95.0:5.0 | 94.3:5.7 |
| Compound 4 | NNPAM | APTMA | 92.5:7.5 | 90.9:9.1 |
| Compound 5 | NNPAM | APTMA | 75.0:25.0 | 74.4:25.6 |
| Compound 6 | DMAM | APTMA | 92.5:7.5 | 79.4:20.4 |
| Compound 7 | NNPAM | — | 100:0 | 100:0 |
| Compound 8 | NNPAM | VBTMA | 95.0:5.0 | 90.6:9.4 |
| Compound 9 | NNPAM/NIPAM (1:1) | APTMA | 97.5 (48.75/48.75):2.5 | 96.7 (49.8/46.9):3.3 |
| Compound 10 | NIPAM | APTMA | 97.5:2.5 | 96.4:3.6 |

Example 13: Test of Polymer Introduction into Cell

Yeast *Saccharomyces* SYT001 strains (Appl. Environ. Microbiol. 2008; 74: 2787-2796) were inoculated into 3 mL of a YPD (yeast extract 1%, peptone 2%, and glucose 2%) medium, and aerobically incubated with shaking at 25° C. for 1 day. After the absorbance (OD600) at 600 nm as a fungus concentration of the culture solution was measured, the culture solution was centrifuged (3,000 rpm, 5 minutes), and the cell was washed twice with water, and washed well, and then pure water was added so that OD600 was 1, and the cell was suspended. Compounds 1 to 7 dissolved in pure water at the concentration of 5% were added to the cell suspension so that the final concentration was 0.05%, and the suspension was incubated for at 25° C. for 0.5 hours. Then, the suspension was centrifuged (10,000 rpm, 1 minute), the supernatant was rapidly removed, and the cells were washed once again with cold water. The washed yeast cells were suspended in water again, and the yeast cell suspension was placed on a slide glass (SUPERFROST: MATSUNAMI) and sealed with a cover glass (MATSUNAMI), and then the slide glass was placed on a stage (Olympus) and observed by a confocal laser scanning microscope (FV1000, Olympus) and a 100× oil-immersion objective lens (UplanSApo N.A.1.40, Olympus). A laser (Multi Ar laser) of 473 nm was applied to the cell, and fluorescent images for fluorescence wavelengths ranging from 500 nm to 600 nm were observed.

Fluorescent images when each compound is introduced are shown in FIG. 1. If APTMA was contained in a unit, regions with a high fluorescence intensity overlapping a differential interference image were intracellularly observed, however, if APTMA was not contained (compound 7) and if SPA, an anionic unit, was contained (compound 1), no fluorescent images were observed at all.

Example 14: Evaluation of Efficiency of Polymer Introduction into Cell

In the same manner as in Example 13, compounds 2 to 6 at the concentration of 0.05% were mixed with and introduced into yeast *Saccharomyces* SYT001 strains. The yeast cells into which the compounds were introduced was subjected to a flow cytometer (FACSCalibur, BD) analysis. Conditions at measurement are as follows: the number of cells measured was set at 10,000, FSC voltage was set at E-1, SSC voltage was set at 201, FL1 voltage was set at 566 V, and FSC threshold was set at 52. After the excitation light of argon laser of 488 nm was irradiated to the cell, fluorescence derived from each compound was detected with a fluorescence detector (FL1) of 515 nm to 545 nm. Regions specific to the yeast cells were selected by SSC and FSC, and a histogram in which the signal fluorescence intensity of FL1, fluorescence emitted from a polymer, was plotted on the horizontal axis and the number of cells having the fluorescence intensity was plotted on the longitudinal axis was prepared to perform an analysis.

Figure 2:
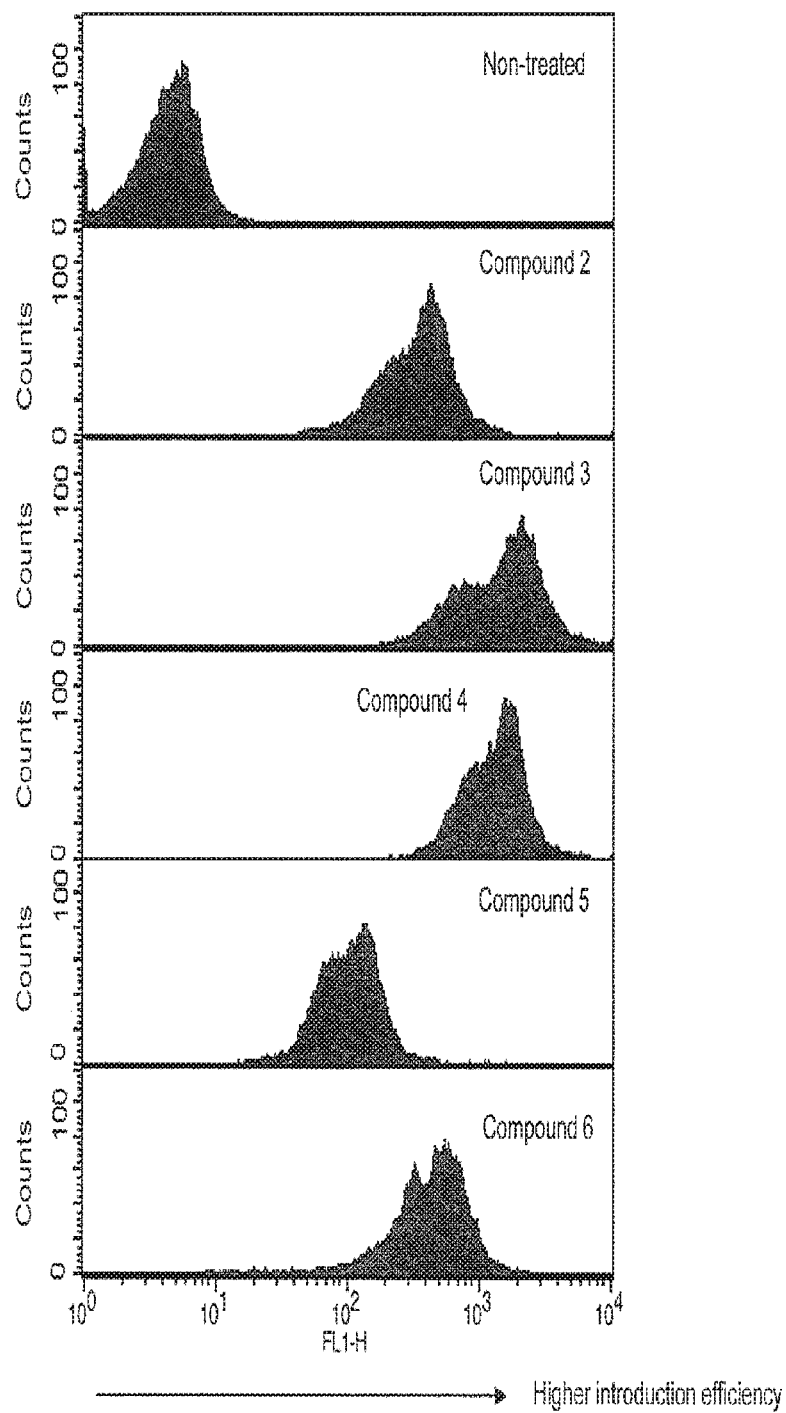
FIG. 2 is a histogram when compounds 2 to 6 were mixed with yeast *Saccharomyces cerevisiae* SYT001 and the fluorescence of the yeast cells was counted by a flow cytometer (excitation wavelength: 488 nm, fluorescence: 515 nm to 545 nm).

The evaluation results are shown in FIG. 2. The drawing shows that the further right the peak of the histogram goes, the larger the amount of polymer introduction into cells is; it can be seen that the higher the proportion of APTMA is (compounds 2 to 5), the more the number of cells with a high intracellular fluorescence intensity is. Similar to the results observed in Example 13, it was revealed that the more the amount of APTMA introduction is, the easier a probe enters into a cell. Comparison between the results of compound 4 and compound 6 showed that this finding is not due to a thermoresponsive unit.

Example 15: Qualitative Evaluation of Ionic Strength of Each Compound in Solution Compounds 1 to 7 were dissolved in pure water at the concentration of 5%, and electrophoresis was performed with a 1% agarose TAE gel (Genius, SK bio). The applied amount was 5 µl. Electrophoresis was performed at 50 V for 1.5 hours. Using ImageQuant LAS 4000 (GE Healthcare), the gel after electrophoresis was excited with Blue Epi light (460 nm, GE Healthcare) and the excitation light and the scattered light were cut with a Y515 filter (GE Healthcare) to detect fluorescence from each probe.

Figure 3:
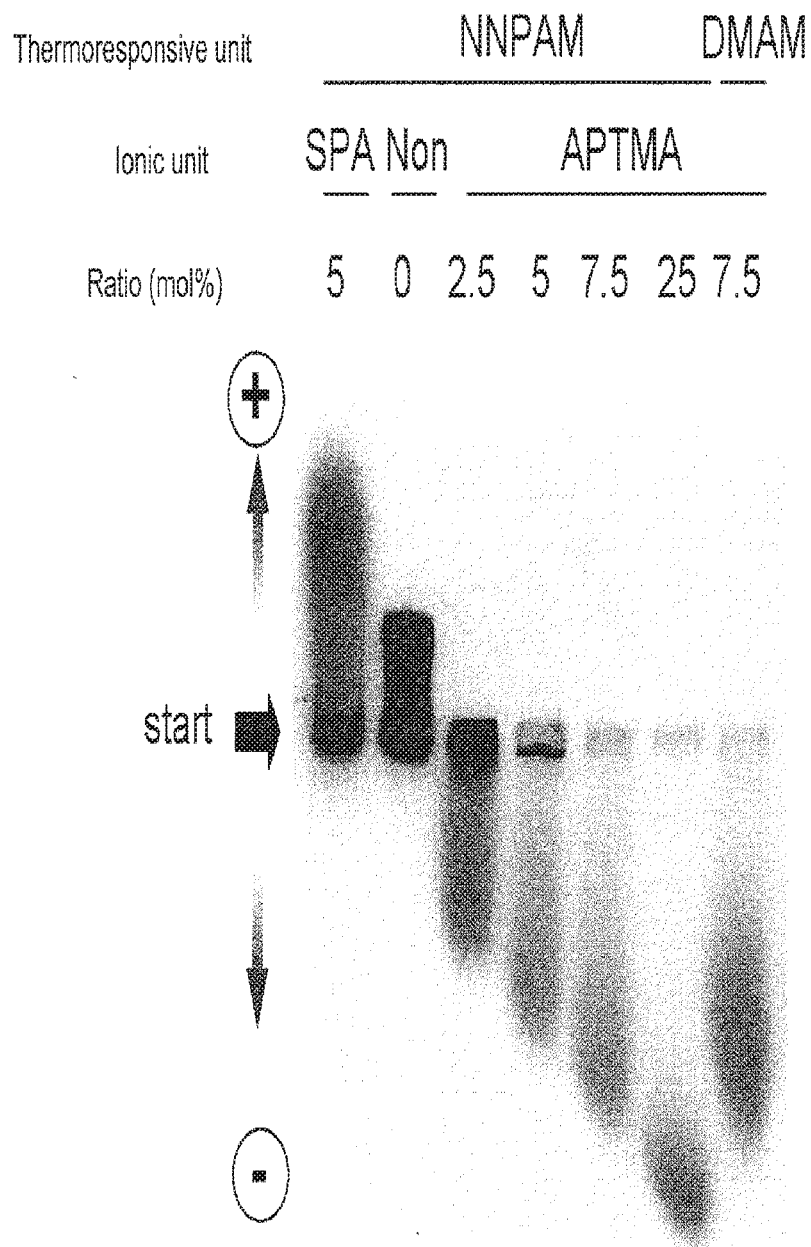
FIG. 3 is a diagram when compounds 1 to 7 were subjected to agarose gel electrophoresis and the ionic strength of each compound was qualitatively evaluated.

The results of the gel after electrophoresis are shown in FIG. 3. For a probe into which APTMA, a cationic group, was not introduced, it was found that the analyte migrates slightly toward the positive charge side from the applied site partly because the main chain itself of acrylamide is negatively charged. For a probe into which SPA, an anionic unit, was introduced, the analyte migrated more toward the positive electrode side, confirming that the entire polymer is negatively charged. On the other hand, for polymers into which a cationic unit was introduced, the analyte migrated more toward the negative electrode side depending on the introduction rate of APTMA, confirming that the introduction amount of APTMA is correlated with cationicity. Furthermore, for a probe into which APTMA was introduced at a proportion of 9.1%, no change in mobility due to NNPAM and DMAM, a thermoresponsive unit, were observed, also confirming that no change in cationicity due to a thermoresponsive unit.

Example 16: Thermoresponsivity Test

A thermoresponsivity test of compounds 2, 3, 4, 5, and 6 in 150 mM KCl was performed by the following procedure. A JASCO FP-6500 spectrofluorometer was used, and using ultrapure water obtained from a Milli-Q reagent system made in Millipore Corporation, KCl purchased from Wako Pure Chemical Industries, Ltd. dissolved to make a 150 mM concentration was used as a solvent. The initial concentration of the compounds in this experiment was 0.01 w/v %, and the excitation wavelength was 456 nm. A JASCO ETC-273T water-cooled Peltier thermostated cell holder was used for temperature control of the solution, and temperature was measured with its accompanying thermocouple. Solution temperature was raised in steps of 2° C., and the fluorescence intensity at each temperature was measured.

Figure 4:
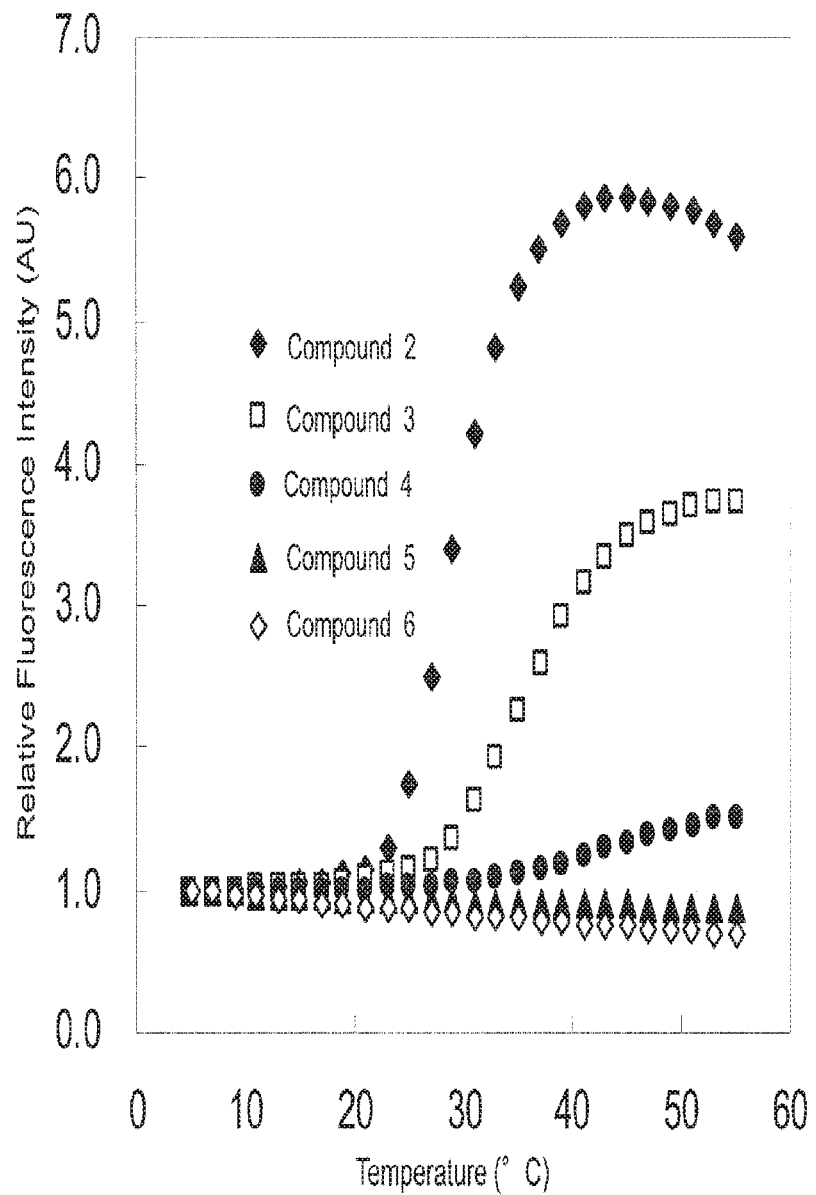
FIG. 4 is an example of thermoresponsivity test results (0.01 w/v %, excitation wavelength of 456 nm) of the fluorescence intensities of compounds 2 to 6 (black rhombus: compound 2, white square: compound 3, black circle: compound 4, black triangle: compound 5, white rhombus: compound 6) in an aqueous 150 mM potassium chloride solution.

The test results are shown in FIG. 4. When DMAM was used as a thermoresponsive unit, no response to change in temperature was observed and no change in fluorescence intensity were observed, while when NNPAM was used as a thermoresponsive unit, change in fluorescence intensity sensitively responding to change in temperature were observed up to 9.1% of the mole fraction of APTMA in the copolymer. However, when the mole fraction of APTMA in the copolymer was 25.6%, the fraction of a thermoresponsive unit becomes low and the fraction of an ionic group becomes too high, resulting in inhibition of the expansion and contraction of a polymer by electrostatic effects, and thus no change in fluorescence intensity responding to temperature were observed. Taken together with the results of Example 13 to 16, it was revealed that in order to sensitively and simply measure intracellular measurement without using a special method, the fraction of APTMA to the sum of NNPAM and APTMA is preferably 2.5% to 7.5% of the monomer input in molar quantity and 3.3% to 9.1% in mole fraction actually contained in the copolymer.

Example 17: Evaluation of Potassium Chloride Concentration Dependency in Thermoresponsivity Test The KCl concentration dependency in the thermoresponsivity of compound 2 was tested and examined by the following procedure. The experimental methods are same as in Example 13, and a solvent was prepared so that KCl concentrations were 0 mM (pure water), 150 mM, 200 mM, and 250 mM.

Figure 5:
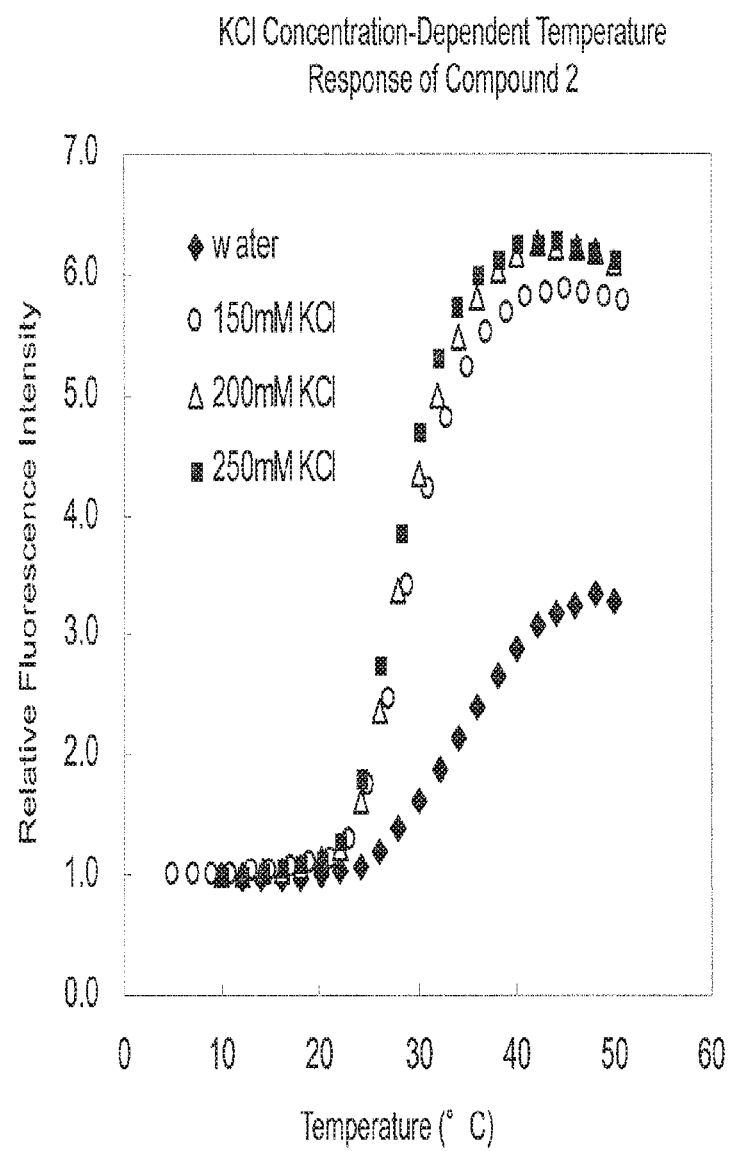
FIG. 5 is an example of thermoresponsivity test results of compound 2 in 0, 150, 200, and aqueous 250 mM potassium chloride solutions (all of which 0.01 w/v %, excitation wavelength of 456 nm, fluorescence wavelength of 566 nm) (black rhombus: in water, white circle: in 150 mM KCl, white triangle: in 200 mM KCl, black square: in 250 mM KCl).

The test results are shown in FIG. 5. Generally, intracellular potassium concentration is estimated to be 150 mM to 250 mM, and it is known that change in intracellular potassium concentration is small unless there is special environmental change. Change in temperature responsivity to change in the concentration of a potassium chloride solution within this range were slightly observed, while change in intracellular potassium concentration were far lower than these change, suggesting no effects on intracellular temperature measurement.

Example 18: Evaluation of pH Responsivity

The pH dependency in the thermoresponsitivity of compound 2 was tested and examined by the following procedure. Using ultrapure water obtained from a Milli-Q reagent system made in Millipore Corporation as a solvent, pH was adjusted to 4 with hydrochloric acid. The ultrapure water was used as a solvent of pH 7. The experimental methods are same as in Example 13.

Figure 6:
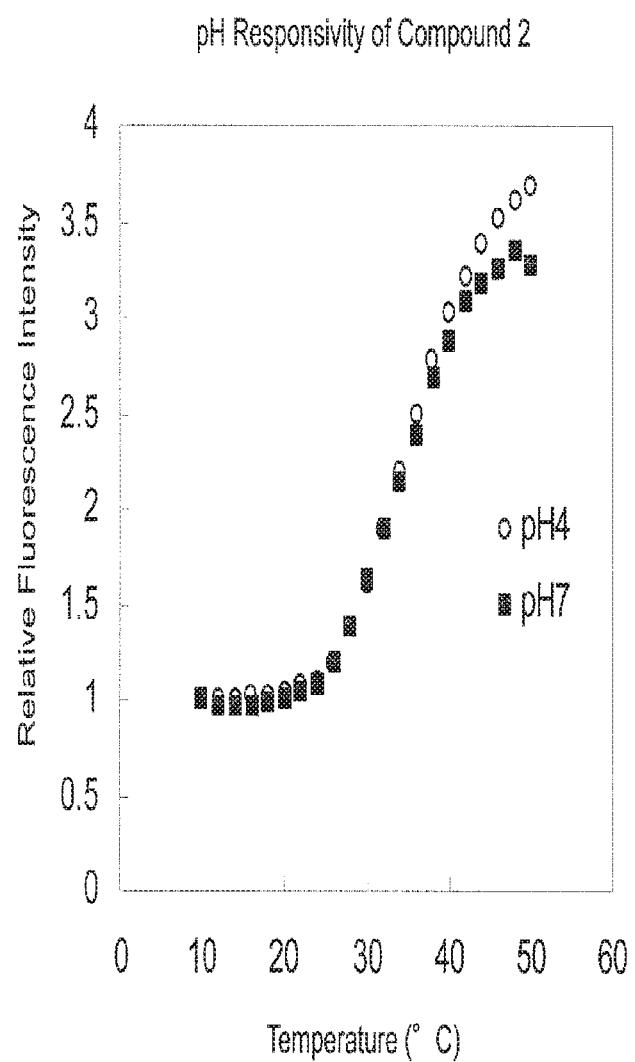
FIG. 6 is an example of a thermoresponsivity test of compound 2 in water at pH 4 and 7 (both of which 0.01 w/v %, excitation wavelength of 456 nm, fluorescence wavelength of 566 nm) (white circle: pH 4, black square: pH 7).

The test results are shown in FIG. 6. In a usual cellular temperature range (20° C. to 40° C.), almost no change in fluorescence intensity due to change in pH were observed. In other words, it was revealed that change in pH have almost no effects on temperature responsivity, showing that fluorescence intensity reflects pH more sensitively.

Example 19: Evaluation of Solvent on Incorporation Efficiency of Probe into Cell In the same manner as in Example 13, compounds 2 and 3 at the concentration of 0.05% were mixed with and suspended in yeast *Saccharomyces* SYT001 strains, and a probe was introduced into the yeast. Six types of solutions and medium of water, 1 M sorbitol, PBS, YPD (yeast extract 1%, peptone 2%, and glucose 2%), 50 mM KCl, and 100 mM KCl were used as solutions and medium for suspending the cell when the compounds and the cell were mixed. The yeast into which each of compounds 2 and 3 were introduced was subjected to flow cytometer (FACSCalibur, BD) analysis. The conditions at measurement and analysis methods are the same as in Example 14.

Figure 7:
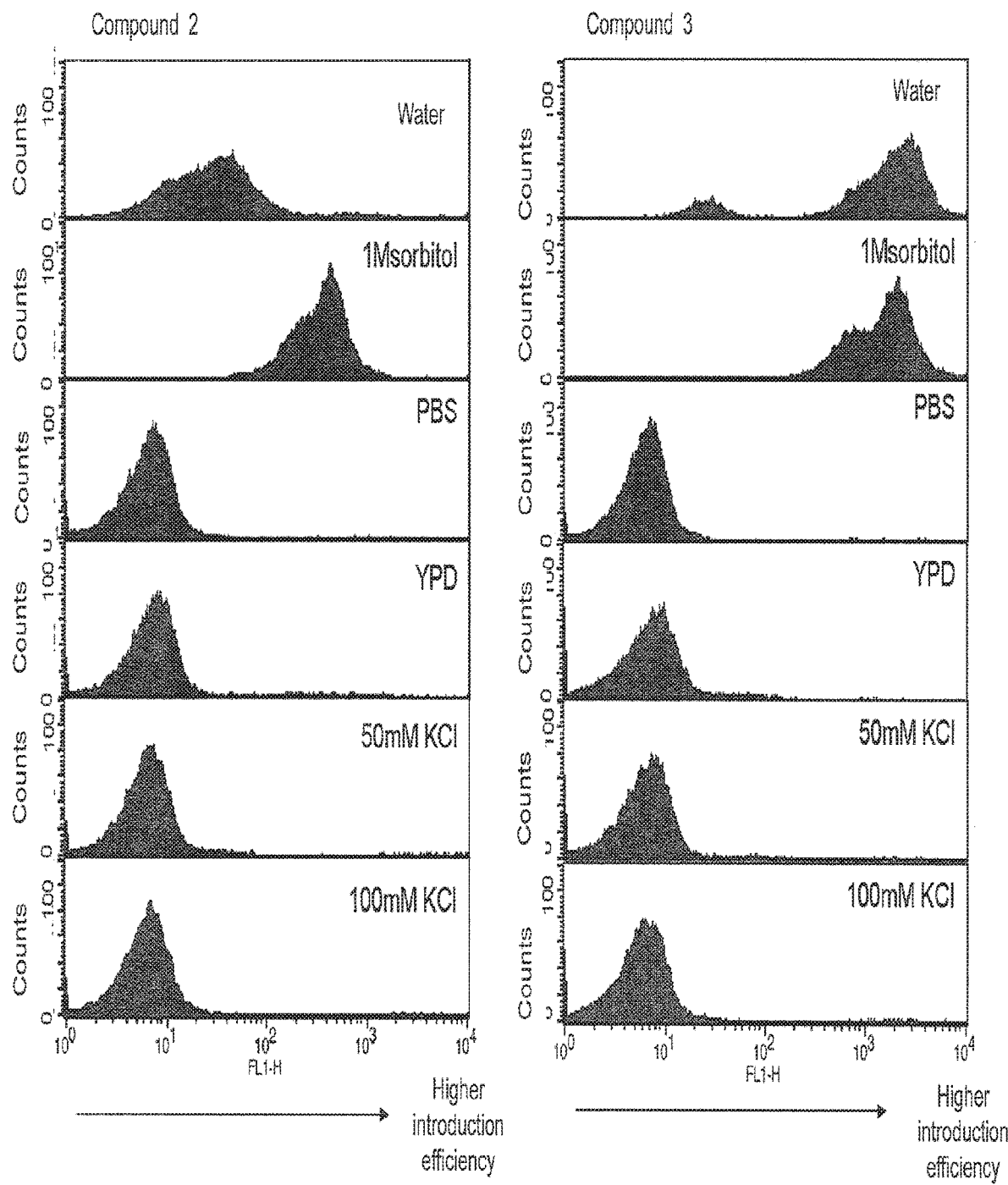
FIG. 7 is a histogram when compounds 2 and 3 were mixed with yeast Saccharomyces cerevisiae SYT001 in six types of solutions and medium of water, 1 M sorbitol, PBS, YPD (yeast extract 1%, peptone 2%, and glucose 2%), 50 mM KCl, and 100 mM KCl and the fluorescence of the yeast cells was detected with a flow cytometer (excitation wavelength: 488 nm, fluorescence: 515 nm to 545 nm).

The analysis results are shown in FIG. 7. Although a cell population with high fluorescence intensity due to compounds 2 and 3 in the yeast was observed in water and a 1 M sorbitol solution, no cell population with high fluorescence intensity was observed in a YPD medium, a PBS buffer, and a KCl solution. Therefore, it was revealed that when a polymer of the present invention is introduced into a cell, the polymer and the cell need to be mixed after the solution is once replaced with a solution with a low ionic strength.

Example 20: Evaluation of Mixing Time at Probe Introduction into Cell

Yeast *Saccharomyces* SYT001 strains were inoculated into a YPD (yeast extract 1%, peptone 2%, and glucose 2%) medium, and aerobically incubated with shaking at 25° C. for 1 day. After the absorbance (OD600) at 600 nm as a fungus concentration of the culture solution was measured, the culture solution was centrifuged (3,000 rpm, 5 minutes), and the cell was washed twice with water, and washed well, and then pure water was added so that OD600 was 1, and the cell was suspended. Compound 2 dissolved in pure water at the concentration of 5% was added to the cell suspension so that the final concentration was 0.05%, and the suspension was incubated for at 25° C. for 5, 10, 15, 20, 30, 40, 50, and 60 minutes. Then, the suspension was centrifuged (10,000 rpm, 1 minute), the supernatant was rapidly removed, and the cell was washed once again with cold water. The washed yeast was suspended in water again, and the yeast was subjected to flow cytometer (FACSCalibur, BD) analysis. The conditions at measurement and analysis methods are the same as in Example 14.

Figure 8:
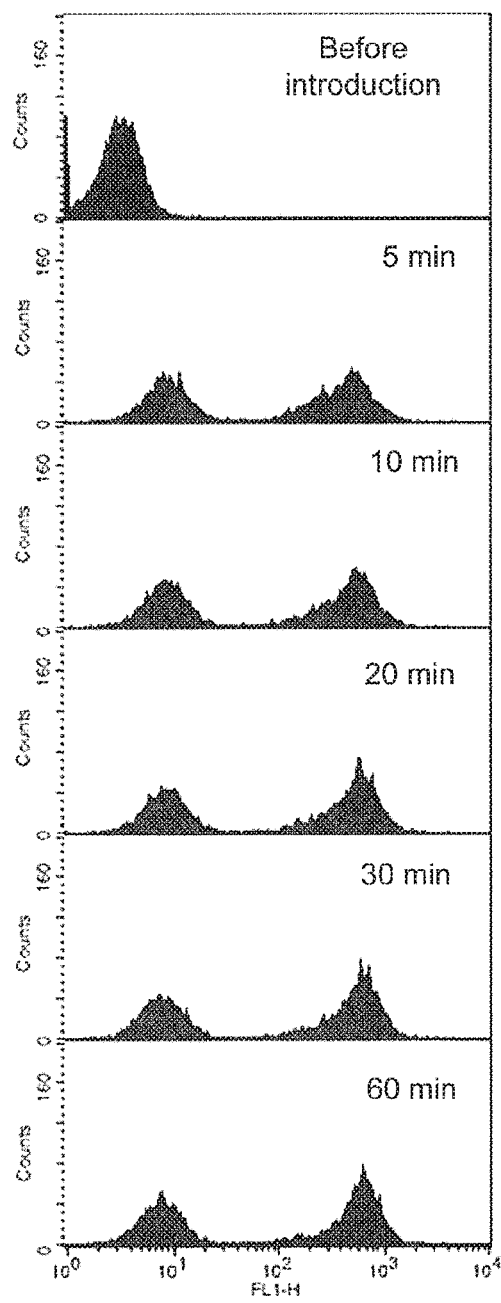
FIG. 8 is a histogram when compound 2 was mixed with yeast Saccharomyces cerevisiae SYT001 in water for 5, 10, 20, 30, or 60 minutes, and then the fluorescence of the yeast cells was detected with a flow cytometer (excitation wavelength: 488 nm, fluorescence wavelength: 515 nm to 545 nm).

The analysis results are shown in FIG. 8. Although the yeast before introduction emitted almost no fluorescence, increased fluorescence intensity was observed immediately after 5 minutes of mixing with a polymer. Then, even when the time of contact between the polymer and the yeast was longer, there were almost no change in the proportion of the yeast introduced. In other words, it was indicated that since a probe of the present invention is intracellularly introduced immediately after contacting with a cell, long-time incubation, etc. is not required and can be simply incorporated into a cell.

Example 21: Measurement of Temperature in Yeast Cells

In the same manner as in Example 13, compounds 2, 3, 4, and 6 at the concentration of 0.05% were mixed with and suspended in yeast *Saccharomyces* SYT001 strains, and a polymer was introduced into the cell. The cell into which the polymer was introduced was suspended in water at the concentration of OD600=1 and put into a cuvette, and a spherical stirrer with a diameter of 2 mm was put into the cuvette. The cuvette was placed in a JASCO FP-6500 spectrofluorometer and rotated at a speed of about 600 rpm to prevent sinking of the yeast, and fluorescence spectrum was measured. The excitation wavelength was 456 nm. A JASCO ETC-273T water-cooled Peltier thermostated cell holder was used for temperature control of the solution, and temperature was measured with its accompanying thermocouple. Solution temperature was raised in steps of 5° C., the solution was incubated for 10 minutes after temperature rise so that intracellular temperature and extracellular temperature were constant, and the fluorescence intensity at each temperature was measured.

Figure 9:
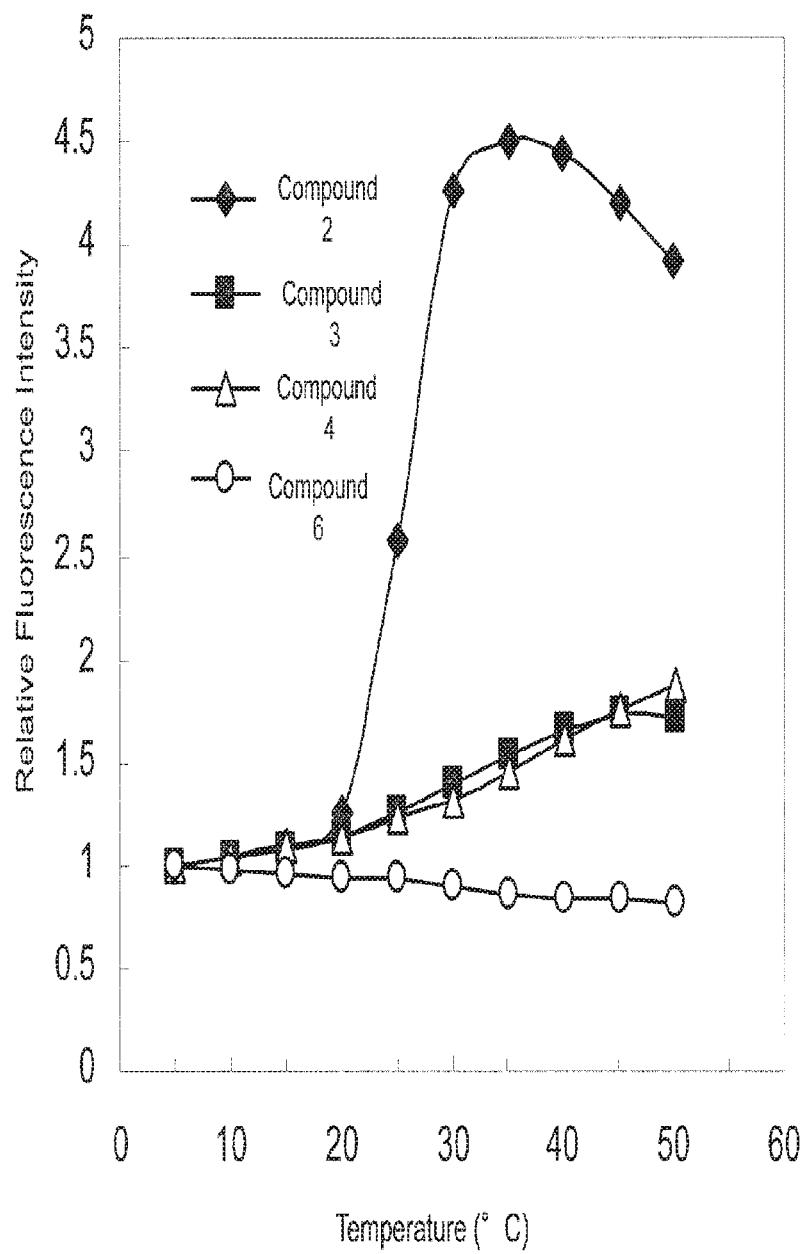
FIG. 9 is an example of thermoresponsivity test results of the fluorescence intensities of compounds 2, 3, 4, and 6 in yeast cells (black rhombus: compound 2, black square: compound 3, white triangle: compound 4, X: compound 6).

The measurement results are shown in FIG. 9. For the results, the fluorescence intensity at 5° C. was defined as 1, and the longitudinal axis was represented by relative fluorescence intensity. The fluorescence wavelength when the maximum fluorescence intensity of each compound was recorded was used. Similar to the results of the thermoresponsitivity of the polymer in 150 mM KCl in Example 16, also in a cell, the polymer developed according to the present invention reflects intracellular temperature, and intracellular fluorescence intensity was increased with increases in temperature. When DMAM, which is non-thermosensitivity, was used, it had been revealed that a probe was intracellularly introduced from the results of the above mentioned examples, but the fluorescence intensity was not increased in response to temperature, as expected, it can be confirmed that DMAM cannot be used as a probe which measures temperature.

Example 22: Accurate Measurement of Intracellular Temperature by Calculating Ratio of Fluorescence Intensity In the same manner as in Example 13, compound 3 at the concentration of 0.05% was mixed with and suspended in yeast *Saccharomyces* SYT001 strains, and a polymer was introduced into the cell. The yeast into which the polymer was introduced was suspended in water again. The yeast cell suspension was poured into a glass bottom dish (35 mm Glass Base Dish, IWAKI), placed on a water jacket stage incubator (CRYO-WJMSI, okolab), and observed by a confocal laser scanning microscope (FV1000, Olympus) and a 100× oil-immersion objective lens (UplanSApo N.A.1.40, Olympus) while temperature was controlled. A laser (Multi Ar laser) of 473 nm was applied to the cell, and fluorescent images for fluorescence wavelengths ranging from 520 nm to 560 nm (P1) and fluorescent images for fluorescence wavelengths ranging from 570 nm to 610 nm (P2) were observed. The obtained images were processed in a FV10-ASW analysis software (Olympus) to calculate a ratio (P1/P2), and images were prepared (P3). The temperature was raised from 15° C. to 40° C. in steps of 5° C., and observation was performed after 10 minutes when temperature was constant.

Figure 10:
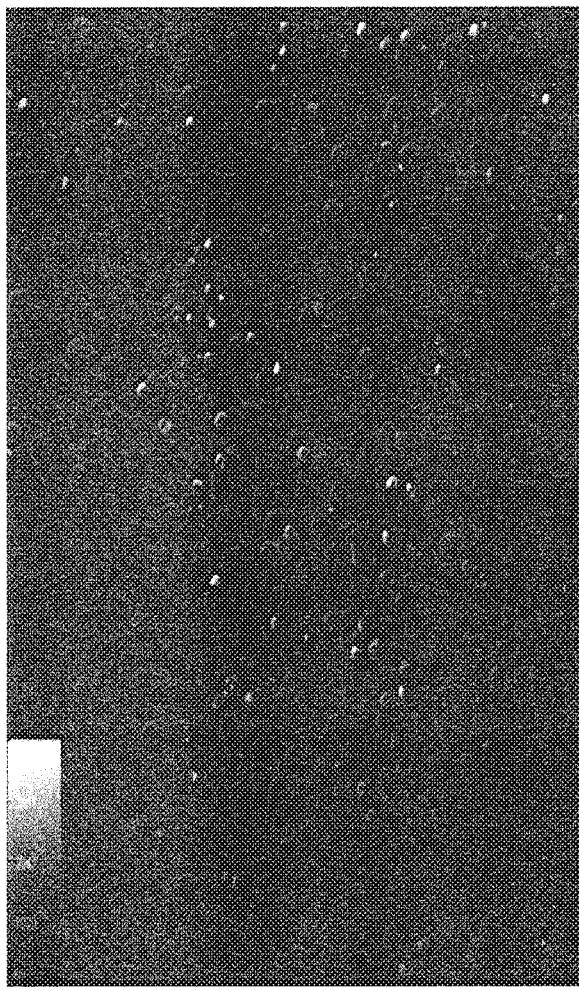
FIG. 10 is an example of photographs when compound 3 is intracellularly introduced into Saccharomyces cerevisiae SYT001 cells and observed by a confocal laser scanning microscope (excitation wavelength of 473 nm, fluorescence wavelength of 520-560 nm).
Figure 10:
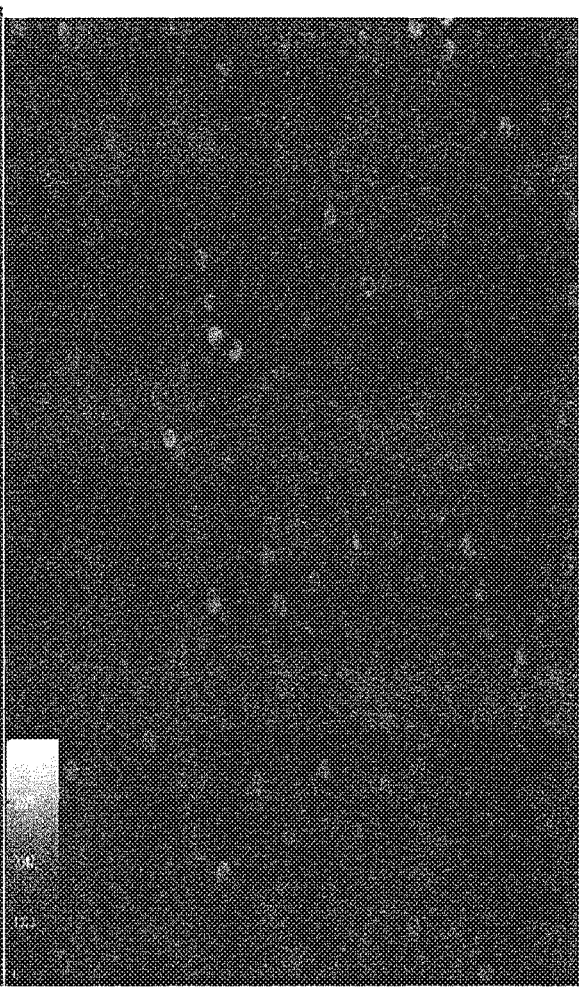
Figure 11:
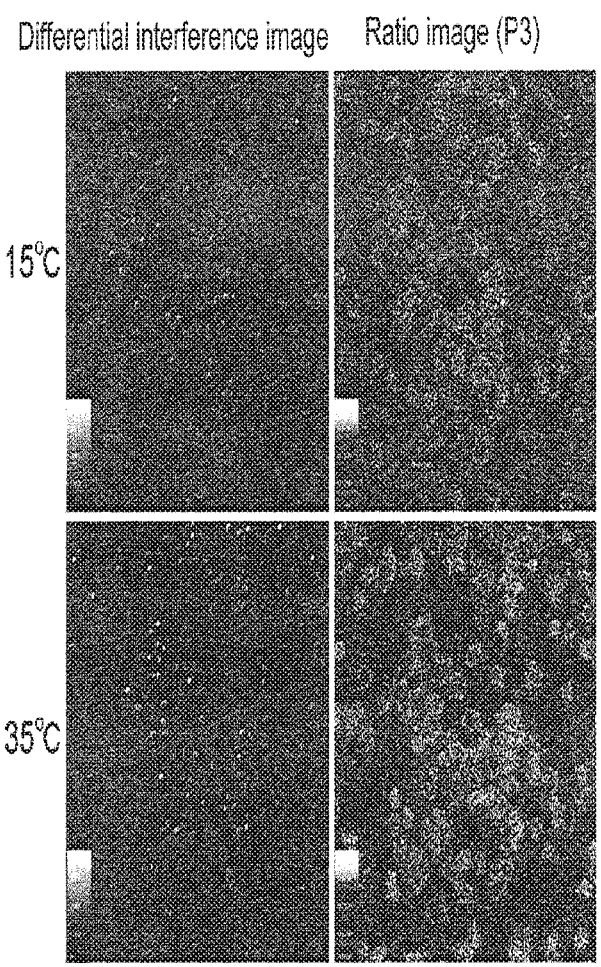
FIG. 11 is an example of fluorescent images (P3) obtained by intracellularly introducing compound 3 into Saccharomyces cerevisiae SYT001 cells to be observed by a confocal laser scanning microscope (excitation wavelength of 473 nm), and by calculating a ratio between fluorescent images at a fluorescence wavelength of 520-560 nm (P1) and fluorescent images at a fluorescence wavelength of 570-610 nm (P2).

The results of P1 at 35° C. are shown in FIG. 10. As is clear from the results, the temperature cannot be accurately estimated from simple fluorescence intensity because the fluorescence intensity does not correspond to temperature. Specifically, the temperature of a cell with high fluorescence intensity is not always high, and it is possible that simply the amount of probe introduction is large. To resolve this, the thermoresponsitivity of this probe needs to be evaluated under the same measurement condition as that for determination of the amount of intracellular probe introduction, however, especially in the latter, accurate calculation is difficult because the fluorescence intensity depends on temperature. Thus, images P3 calculated from a ratio between P1 and P2 at 15° C. and 35° C. are shown in FIG. 11. In FIG. 11, the ratio of fluorescence intensity is represented in pseudocolor so that the ratio is 0.5 (black) to 1.0 (white). As a curve example of a calibration curve, a ratio of fluorescence intensity (520-560 nm/570-610 nm) was calculated from the fluorescence spectrum at each temperature when compound 3 was introduced into the yeast as measured in Example 20, and the temperature response curve was shown in FIG. 12.

Figure 12:
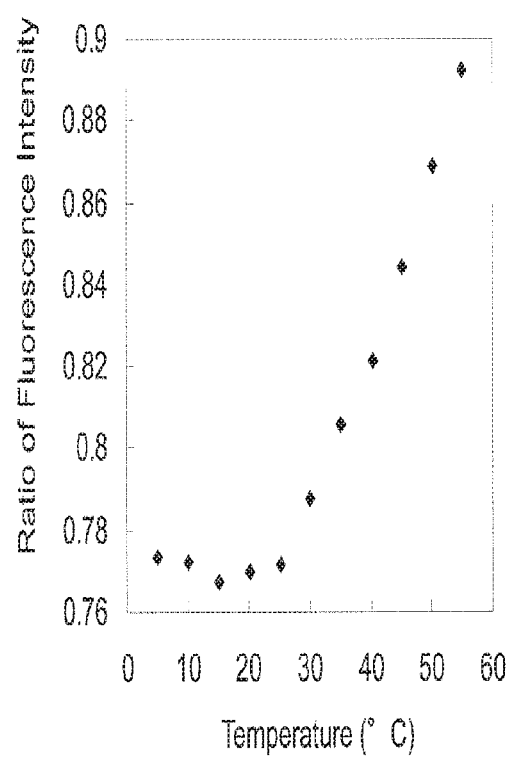
FIG. 12 is an example of a temperature response curve obtained by, using a spectrofluorometer, calculating a ratio of fluorescence intensity (520-560 nm/570-610 nm) from the fluorescence spectrum at each temperature when compound 3 is introduced into yeast, and by plotting the ratio of fluorescence intensity for each temperature.
Figure 13:
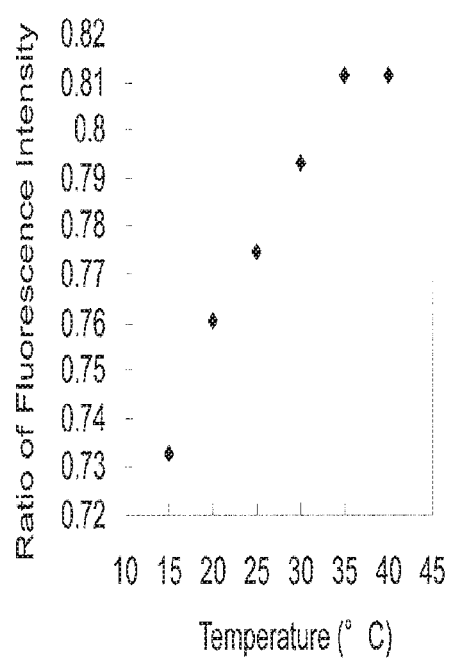
FIG. 13 is an example of a temperature response curve obtained by, using a fluorescence microscope, intracellularly introducing compound 3 into yeast Saccharomyces cerevisiae SYT001 to be observed by a confocal laser scanning microscope (excitation wavelength of 473 nm), by calculating a ratio of fluorescence intensity (P1/P2) between the fluorescence intensities from fluorescent images at a fluorescence wavelength of 520-560 nm (P1) and the fluorescence intensities from fluorescent images at a fluorescence wavelength of 570-610 nm (P2), and by plotting a ratio of fluorescence intensity for each temperature.

Furthermore, from a microscope photograph at each temperature, by surrounding the entire photographed field and by plotting a ratio of fluorescence intensity (P1/P2) and temperature, the results were as shown in FIG. 13. Values in FIG. 12 and FIG. 13 are near each other, this revealed that intracellular temperature can be calculated from a ratio of fluorescence intensity by microscopy (FIG. 11) with the calibration curve in FIG. 12.

This result revealed that it is possible not only to compare temperatures of the same cell but also to compare intracellular temperatures of other cells under the same condition. Specifically, for example, differences in individual cell temperature in a yeast population can be used for grasping the physiological state of the cell, etc.

Example 23: Evaluation of Cytotoxicity of Probe

In the same manner as in Example 13, compounds 2 to 7 at the concentration of 0.005%, 0.025%, 0.05%, or 0.25% were mixed with and suspended in yeast *Saccharomyces* SYT001 strains, and a polymer was introduced into the cell. After the yeast into which the polymer was introduced was washed twice with water and suspended in water again, the yeast was spotted on a YPD plate so that the number of cells was $10^4$, $10^3$, $10^2$, or 10 and incubated at 25° C. for 2 days, and then the plate was photographed, and cytotoxicity was qualitatively evaluated.

Figure 14:
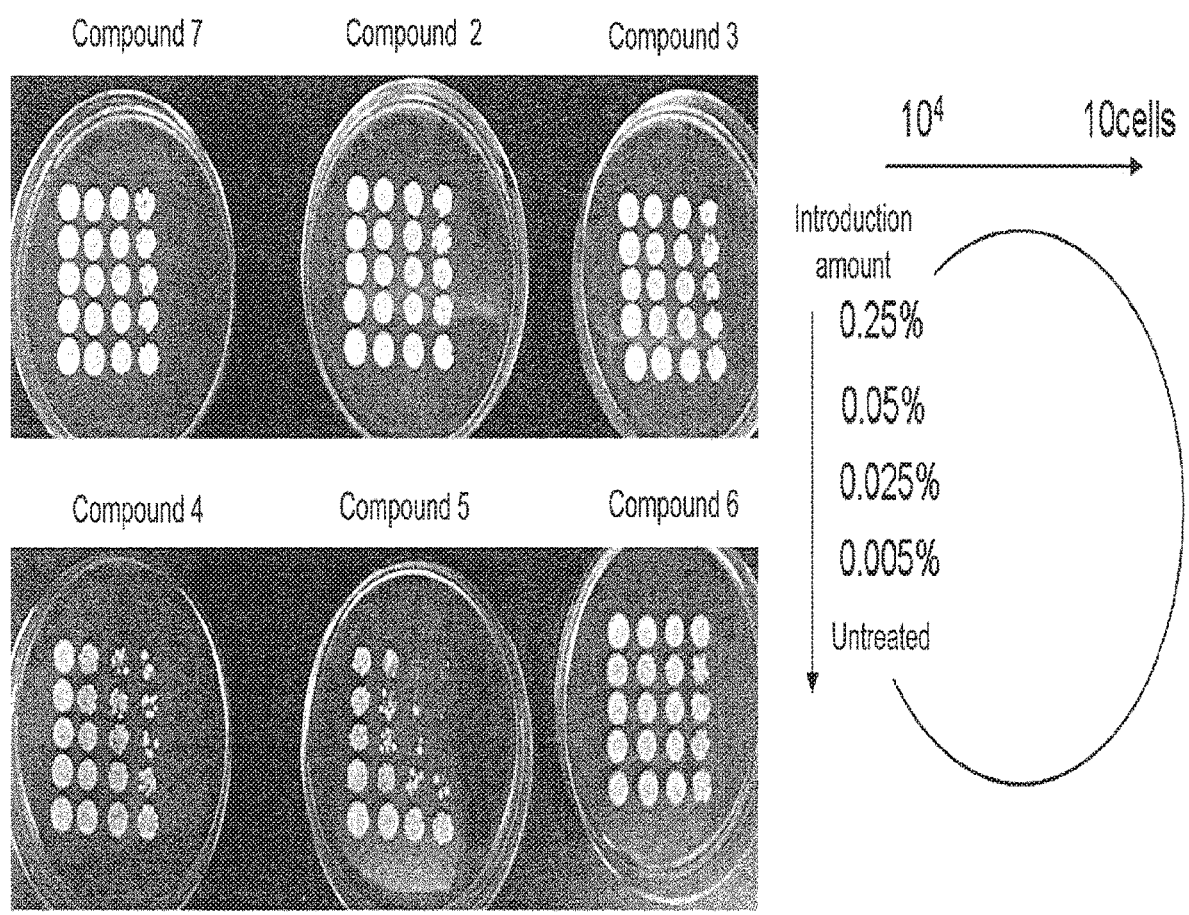
FIG. 14 is a set of photographs of plates taken by the following procedure. Compounds 2 to 7 at the concentration of 0.005%, 0.025%, 0.05%, or 0.25% were mixed with and suspended in yeast Saccharomyces SYT001 strains, a polymer was introduced into the cell, the yeast into which the polymer was introduced was washed twice with water, and the yeast was suspended in water again, and then the yeast was spotted on a YPD plate so that the number of cells was $10^4$, $10^3$, $10^2$, or 10, and the yeast was incubated at 25° C. for 2 days.

The results are shown in FIG. 14. It was found that toxicity was gradually increased depending on the additive amount when the mole fraction of APTMA in the copolymer was more than 9.1%. It can be seen that especially when the mole fraction of APTMA in the copolymer was 25.6%, there was considerable toxicity regardless of the introduction amount. However, for compounds 2 and 3 with a mole fraction of APTMA in the copolymer, which is useful as an intracellular introduction type temperature measurement probe, of 3.3% or 5.7%, less toxicity was observed even when the introduction amount was 0.05%. Meanwhile, since probes seem to be introduced into almost all cells from the results of FIG. 2 in Example 14, it was showed that cytotoxicity is low even when a probe is intracellularly introduced.

Example 24: Application of Probe of Present Invention to Cultured Cells

Human embryonic kidney (HEK)293T cells and mouse macrophage-like RAW264 cells were incubated in a DMEM medium (10% FBS, 1% penicillin-streptomycin) and a 35 mm glass bottom dish (seeded $1 \times 10^6$ cells/ml). After one day, compounds 1, 4, and 7 were added so that the final concentration was 0.05%, and incubated at 37° C. for 2 hours. Then, the medium was washed with PBS at microscopy, and replaced with a phenol red-free medium to perform microscopy. The microscopy was performed with a confocal laser scanning microscope (FV1000, Olympus) and a 60× oil-immersion objective lens (UplanSApo N.A.1.40, Olympus). A laser (Multi Ar laser) of 473 nm was applied to the cells, and fluorescent images for fluorescence wavelengths ranging from 500 nm to 600 nm were observed.

Figure 15:
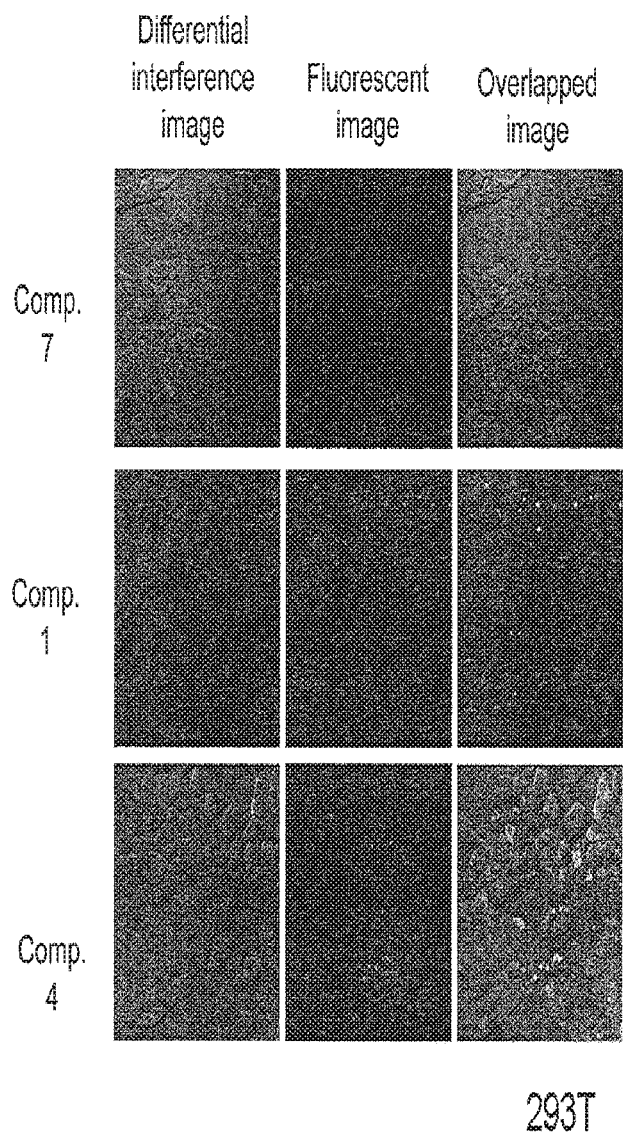
FIG. 15 is a set of fluorescent images obtained by mixing a human embryonic kidney (HEK) 293T cell with compound 1, 4, or 7 at the final concentration of 0.05% to be observed by a confocal laser scanning microscope (excitation wavelength of 473 nm, fluorescence wavelength of 500-600 nm).
Figure 16:
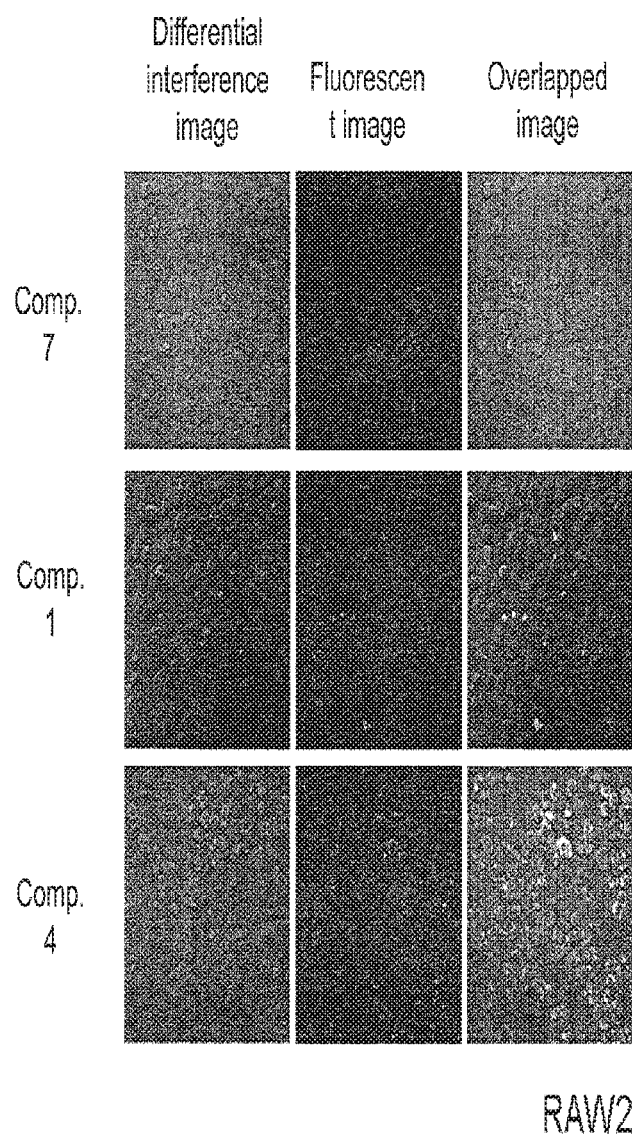
FIG. 16 is a set of fluorescent images obtained by mixing a RAW264 mouse macrophage-like cell with compound 1, 4, or 7 at the final concentration of 0.05% to be observed by a confocal laser scanning microscope (excitation wavelength of 473 nm, fluorescence wavelength of 500-600 nm).

The results of HEK293T cells are shown in FIG. 15 and the results of RAW264 cells are shown in FIG. 16. In both FIG. 15 and FIG. 16, no signal in the fluorescent images was observed at all for compound 7 without an ionic group, while increased intracellular signal intensity was observed for compound 4 into which APTMA, a cationic group, was introduced. Meanwhile, an intracellular signal was slightly observed also for compound 1 into which an anionic group was introduced, but both its number and intensity were very low, indicating that a cationic group is important for probe introduction into a cell. It was also indicated that a probe of the present invention is applicable also to animal cells.

Example 25: Application of Probe of Present Invention to *E. coli*

*E. coli* DH5α was inoculated into a YPD (tryptone 10 g, yeast extract 5 g, and sodium chloride 5 g) medium, and incubated at 37° C. for 16 hours. Then, after the absorbance (OD600) at 600 nm as a fungus concentration of the culture solution was measured, the culture solution was centrifuged (12,000 rpm, 1 minute), and the cell was washed twice with water, and washed well, and then pure water was added so that OD600 was 0.1, and the cell was suspended. Compound 4 dissolved in pure water at the concentration of 5% were added to the cell suspension so that the final concentration was 0.05%, and the suspension was incubated for at 25° C. for 0.5 hours. Then, the suspension was centrifuged (12,000 rpm, 1 minute), the supernatant was rapidly removed, and the cell was washed once again with cold water. The washed *E. coli* was suspended in water again, poured into a glass bottom dish (35 mm Glass Base Dish, IWAKI), placed on a water jacket stage incubator (CRYO-WIMSI, okolab), and observed by a confocal laser scanning microscope (FV1000, Olympus) and a 100× oil-immersion objective lens (UplanSApo N.A.1.40, Olympus) while temperature was controlled. A laser (Multi Ar laser) of 473 nm was applied to the cell, and fluorescent images for fluorescence wavelengths ranging from 500 nm to 600 nm were observed. Measurement was performed at two observational temperatures of 25° C. and 41° C.

Figure 17:
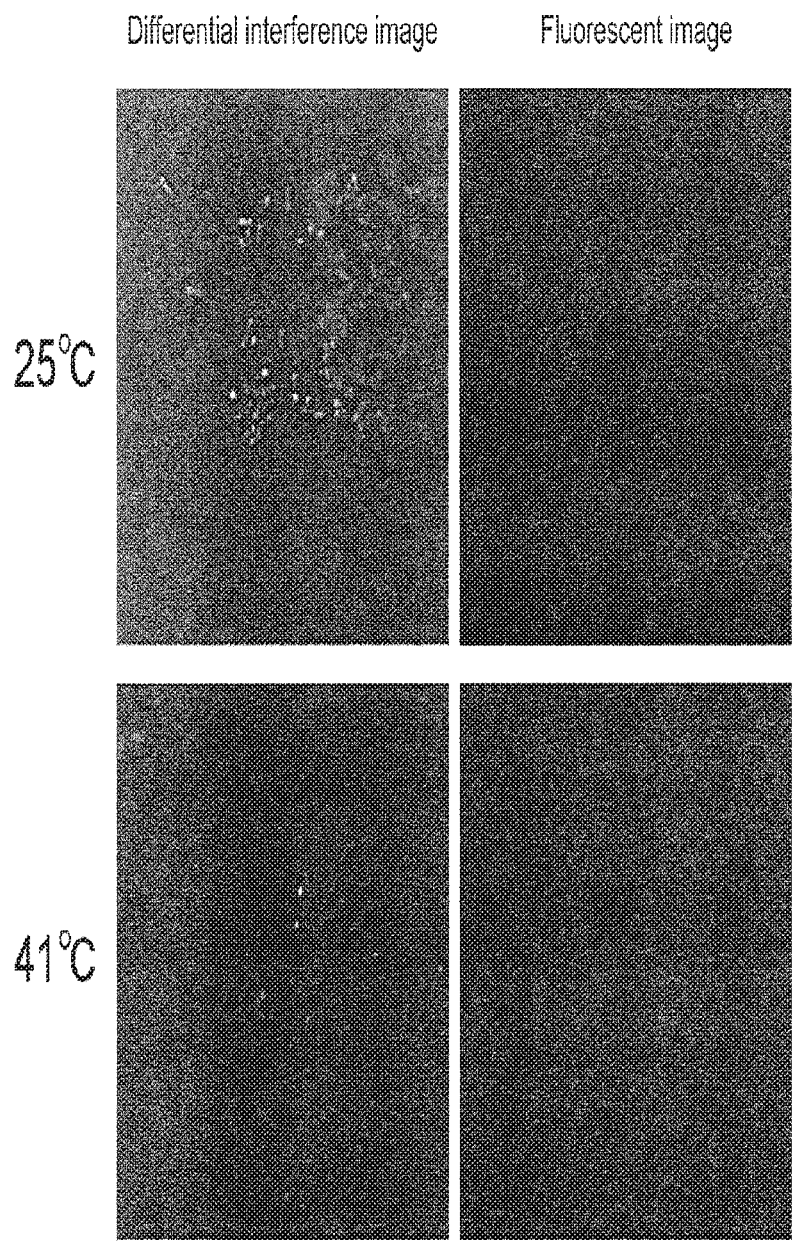
FIG. 17 is an example of photographs when compound 4 was mixed with E. coli DH5a cells and observed by a confocal laser scanning microscope under the temperature condition of 25° C. or 41° C. (excitation wavelength of 473 nm, fluorescence wavelength of 500-600 nm).

The results are shown in FIG. 17. As shown in FIG. 17, it was revealed that also in *E. coli*, a cationic temperature-sensitive probe of the present invention is introduced into a cell, and the number of cells with high fluorescence intensity with a rise in temperature. In other words, it was indicated that this polymer is applicable to microorganisms such as *E. coli* and can be applied to various cell strains.

Example 26: Test of Polymer Introduction into Cell

Yeast *Saccharomyces* SYT001 strains were inoculated into 3 mL of a YPD (yeast extract 1%, peptone 2%, and glucose 2%) medium, and aerobically incubated with shaking at 25° C. for 1 day. After the absorbance (OD600) at 600 nm as a fungus concentration of the culture solution was measured, the culture solution was centrifuged (3,000 rpm, 5 minutes), and the cell was washed twice with water, and washed well, and then pure water was added so that OD600 was 1, and the cell was suspended. Compound 8 dissolved in pure water at the concentration of 5% was added to the cell suspension so that the final concentration was 0.05%, and the suspension was incubated for at 25° C. for 0.5 hours. Then, the suspension was centrifuged (10,000 rpm, 1 minute), the supernatant was rapidly removed, and the cell was washed once again with cold water. The washed yeast was suspended in water again, and the yeast cell suspension was placed on a slide glass (SUPERFROST: MATSUNAMI) and sealed with a cover glass (MATSUNAMI), and then the slide glass was placed on a stage (Olympus) and observed by a confocal laser scanning microscope (FV1000, Olympus) and a 100× oil-immersion objective lens (UplanSApo N.A.1.40, Olympus). A laser (Multi Ar laser) of 473 nm was applied to the cell, and fluorescent images for fluorescence wavelengths ranging from 500 nm to 600 nm were observed.

Figure 18:
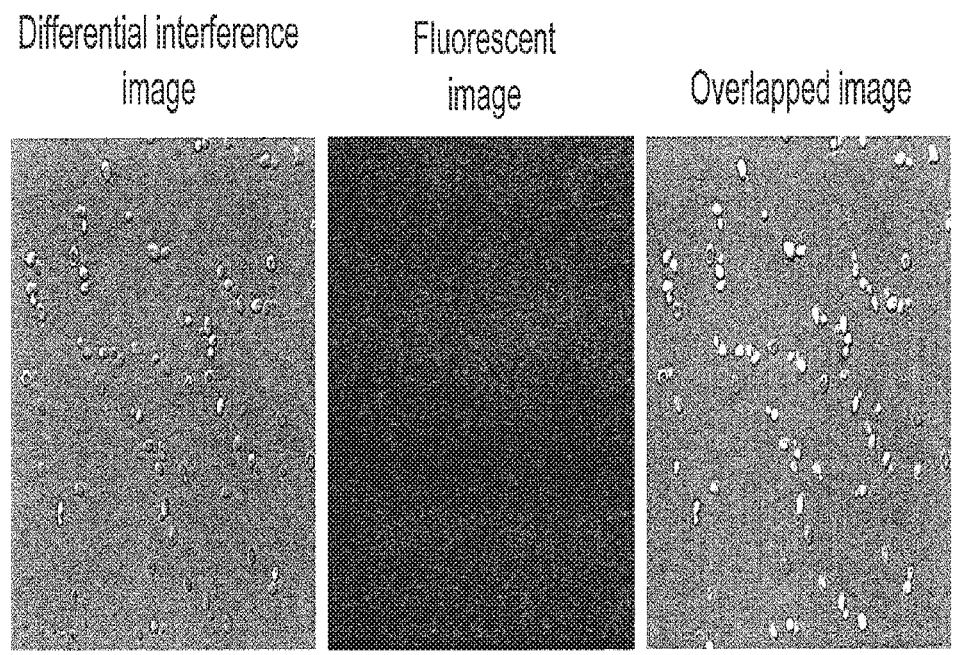
FIG. 18 is an example of photographs when compound 8 was mixed with Saccharomyces cerevisiae SYT001 cells and observed by a confocal laser scanning microscope (excitation wavelength of 473 nm, fluorescence wavelength of 500-600 nm).

A fluorescent image when compound 8 is introduced is shown in FIG. 18. If not only APTMA but also VBTMA, which is also a cationic unit, is in a unit, regions with a high fluorescence intensity overlapping a differential interference image were intracellularly observed. Therefore, it was found that substances other than APTMA can be used for a cell introduction type cationic unit.

Example 27: Thermoresponsivity Test

A thermoresponsivity test of compound 8 in 150 mM KCl was performed by the following procedure. A JASCO FP-6500 spectrofluorometer was used, and using ultrapure water obtained from a Milli-Q reagent system made in Millipore Corporation, KCl purchased from Wako Pure Chemical Industries, Ltd. dissolved to make a 150 mM concentration was used as a solvent. The initial concentration of the compound in this experiment was 0.01 w/v %, and the excitation wavelength was 456 nm. A JASCO ETC-273T water-cooled Peltier thermostated cell holder was used for temperature control of the solution, and temperature was measured with its accompanying thermocouple. Solution temperature was raised in steps of 2° C., and the fluorescence intensity at each temperature was measured.

Figure 19:
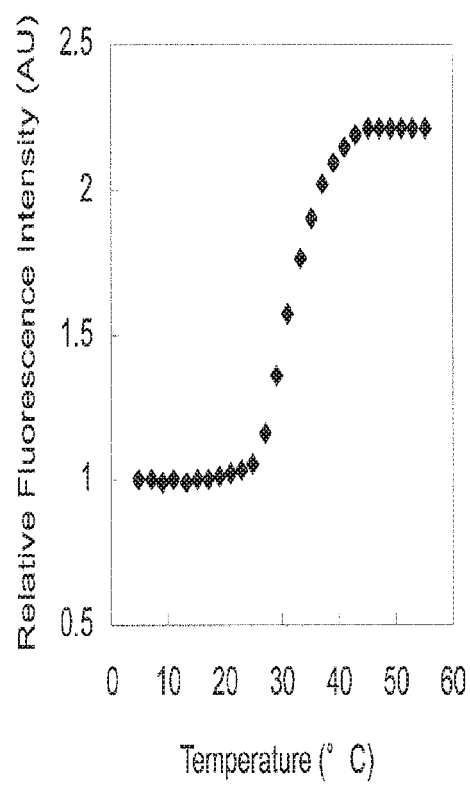
FIG. 19 is an example of thermoresponsivity test results (0.01 w/v %, excitation wavelength of 456 nm) of the fluorescence intensity of compound 8 (black rhombus) in an aqueous 150 mM potassium chloride solution.

The test results are shown in FIG. 19. Even when VBTMA was used as a cationic unit, change in fluorescence intensity in response to temperature increase in a 150 mM potassium chloride solution could be confirmed. With regard to temperature responsivity, it is desirable that acrylamide, methacrylamide, or acrylic acid is contained in all units, however, it was revealed that if the mole fraction in a copolymer is about 10% as in this example, the probe functions as a probe that well responds to temperature even when a usual vinyl-type monomer such as styrene group is comprised in a unit.

Example 28: Measurement of Temperature in Yeast Cells

In the same manner as in Example 13, compound 8 at the concentration of 0.05% was mixed with and suspended in yeast *Saccharomyces* SYT001 strains, and a polymer was introduced into the cell. The cell into which the polymer was introduced was suspended in water at the concentration of OD600=1 and put into a cuvette, and a spherical stirrer with a diameter of 2 mm was put into the cuvette. The cuvette was placed in a JASCO FP-6500 spectrofluorometer and rotated at a speed of about 600 rpm to prevent sinking of the yeast, and fluorescence spectrum was measured. The excitation wavelength was 456 nm. A JASCO ETC-273T water-cooled Peltier thermostated cell holder was used for temperature control of the solution, and temperature was measured with its accompanying thermocouple. Solution temperature was raised in steps of 5° C., the solution was incubated for 10 minutes after temperature rise so that intracellular temperature and extracellular temperature were constant, and the fluorescence intensity at each temperature was measured.

Figure 20:
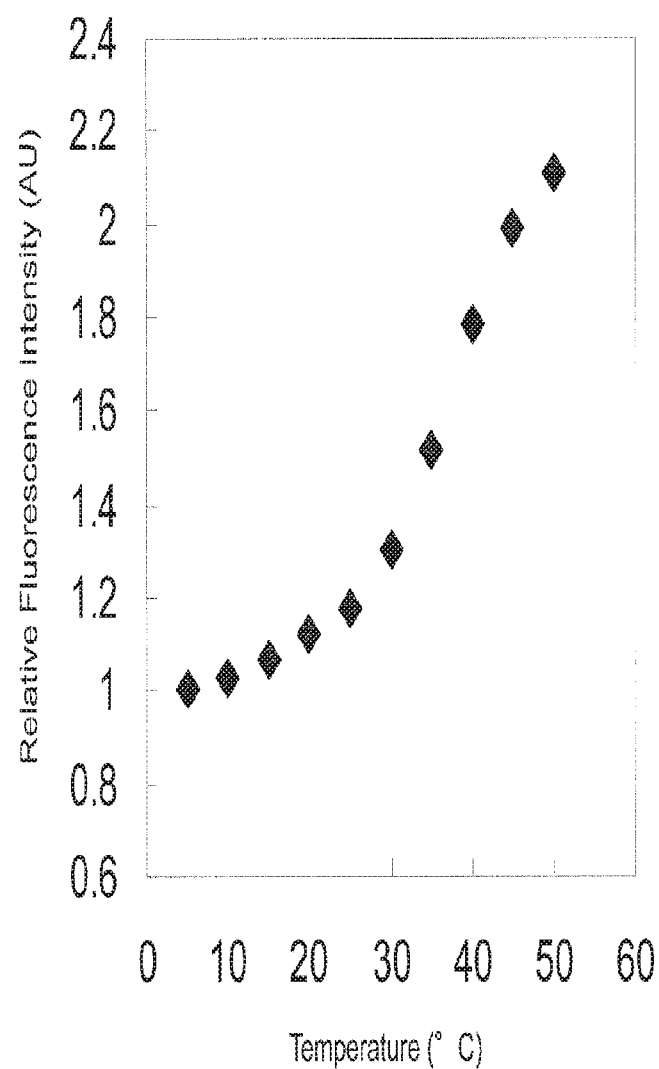
FIG. 20 is an example of thermoresponsivity test results of the fluorescence intensity of compound 8 in yeast cells (black rhombus).

The measurement results are shown in FIG. 20. For the results, the fluorescence intensity at 5° C. was defined as 1, and the longitudinal axis was represented by relative fluorescence intensity. The fluorescence wavelength when the maximum fluorescence intensity of each compound was recorded was used. Similar to the results of the thermo-responsivity of the polymer in 150 mM KCl in Example 16, also in a cell, the polymer developed according to the present invention reflects intracellular temperature, and intracellular fluorescence intensity was increased with increases in temperature. The results of Example 26 to 28 revealed that also for a probe using a cationic unit other than APTMA, the probe can be simply introduced into a cell and has a function that the fluorescence intensity increases in response to temperature rise in a cell.

Example 29: Test of Polymer Introduction into Yeast Cells for Compounds 9 and 10

Yeast *Saccharomyces* SYT001 strains were inoculated into 3 mL of a YPD (yeast extract 1%, peptone 2%, and glucose 2%) medium, and aerobically incubated with shaking at 25° C. for 1 day. After the absorbance (OD600) at 600 nm as a fungus concentration of the culture solution was measured, the culture solution was centrifuged (3,000 rpm, 5 minutes), and the cell was washed twice with 1.2 M sorbitol, and washed well, and then 1.2 M sorbitol was added so that OD600 was 1, and the solution was suspended. Compounds 9 and 10 dissolved in pure water at the concentration of 5% were added to the cell suspension so that the final concentration was 0.05%, and the suspension was incubated for at 25° C. for 20 minutes. Then, the suspension was centrifuged (12,000 rpm, 1 minute), the supernatant was rapidly removed, and the cell was washed once again with cold 1.2 M sorbitol and 50 mM KCl. The washed yeast was suspended in 1.2 M sorbitol again, and the yeast cell suspension was placed on a slide glass (SUPERFROST: MATSUNAMI) and sealed with a cover glass (MATSUNAMI), and then the slide glass was placed on a stage (Olympus) and observed by a confocal laser scanning microscope (FV1000, Olympus) and a 100× oil-immersion objective lens (UplanSApo N.A.1.40, Olympus). A laser (Multi Ar laser) of 473 nm was applied to the cell, and fluorescent images for fluorescence wavelengths ranging from 500 nm to 600 nm were observed.

Figure 21:
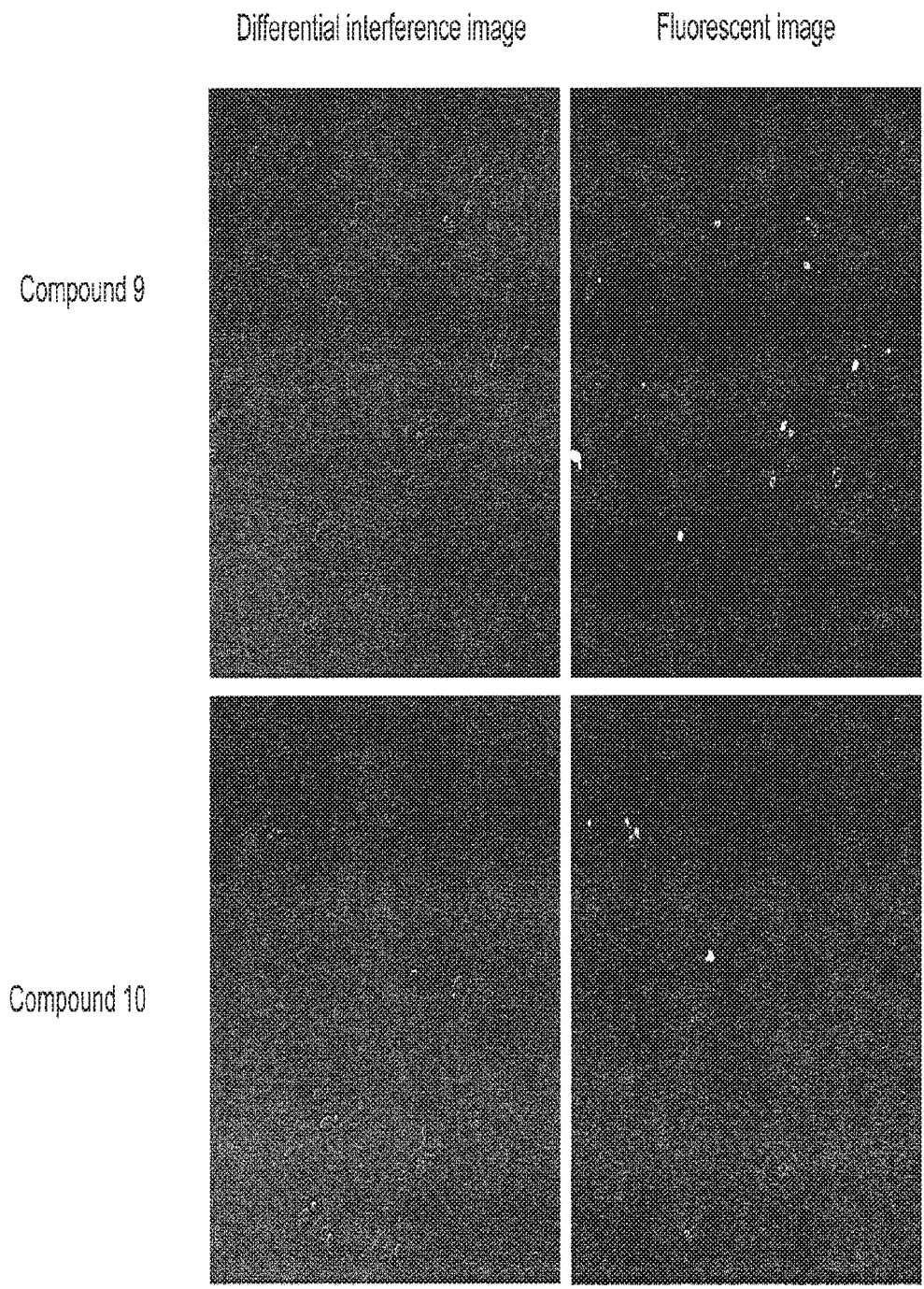
FIG. 21 is an example of photographs when compound 9 or 10 was mixed with Saccharomyces cerevisiae SYT001 cells and observed by a confocal laser scanning microscope (excitation wavelength of 473 nm, fluorescence wavelength of 500-600 nm).

Fluorescent images when compounds 9 and 10 were introduced are shown in FIG. 21. It could be confirmed that even when substances other than NNPAM are used for a thermoresponsive unit, a probe can be introduced into a cell. Furthermore, it was confirmed that a probe can be introduced into a cell even when two thermoresponsive units of NIPAM and NNPAM are used.

Example 30: Thermoresponsivity Test

A thermoresponsivity test of compounds 2, 9, and 10 in 150 mM KCl was performed similar to Example 16. Solution temperature was raised in steps of 2° C., and the fluorescence intensity at each temperature was measured.

Figure 22:
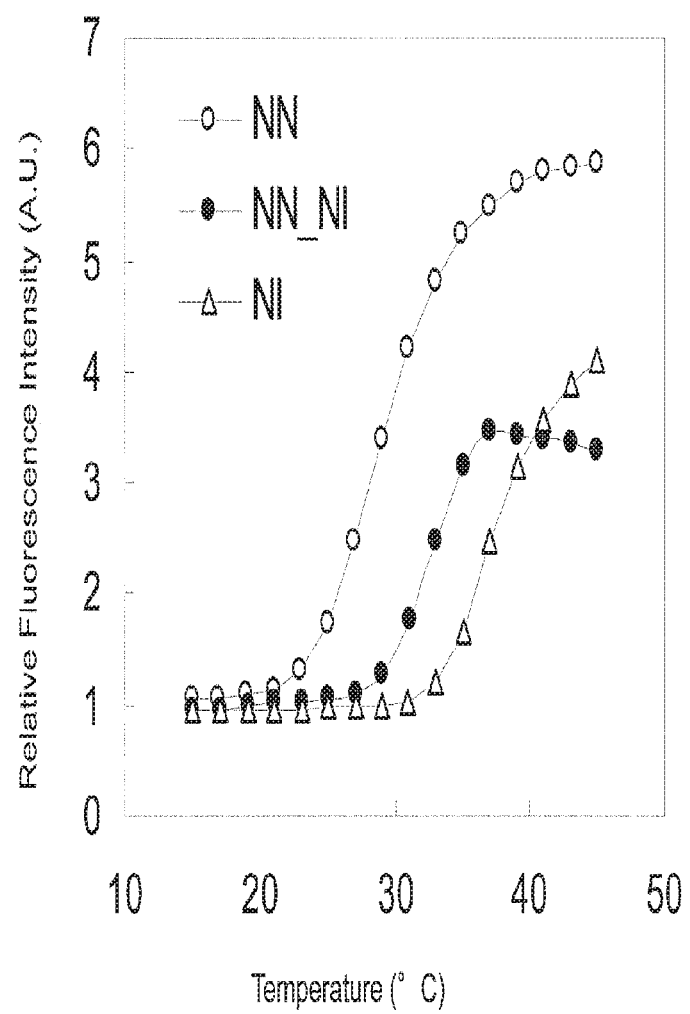
FIG. 22 is an example of thermoresponsivity test results (0.01 w/v %, excitation wavelength of 456 nm) of the fluorescence intensities of compounds 2, 9, and 10 (white circle: compound 2, black circle: compound 9, white triangle: compound 10) in an aqueous 150 mM potassium chloride solution.

The test results are shown in FIG. 22. It could be confirmed that by changing a thermoresponsive site from NNPAM to NIPAM, a temperature-responsive region can be changed. It was found that in NNPAM/NIPAM in which a copolymer was synthesized by mixing both monomers at a ratio of 1:1, the temperature-responsive region falls between the temperature-responsive regions of NNPAM and NIPAM. It could be confirmed that by changing these fractions, a fluorescent temperature sensor responding to an arbitrary temperature range near 30° C. to 50° C. can be made.

Example 31: Change in Measurement Range of Temperature in Yeast Cells Due to Differences in Thermoresponsive Unit In the same manner as in Example 29, compounds 2, 9, and 10 at the concentration of 0.05% were mixed with and suspended in yeast *Saccharomyces* SYT001 strains, and a polymer was introduced into the cell. The cell into which the polymer was introduced was suspended in PBS at the concentration of OD600=1 and put into a cuvette, and a spherical stirrer with a diameter of 2 mm was put into the cuvette. The cuvette was placed in a JASCO FP-6500 spectrofluorometer and rotated at a speed of about 800 rpm to prevent sinking of the yeast, and fluorescence spectrum was measured. The excitation wavelength was 456 nm. A JASCO ETC-273T water-cooled Peltier thermostated cell holder was used for temperature control of the solution, and the temperature in the cell holder was measured with its accompanying thermometer. Solution temperature was raised in steps of 5° C., the solution was incubated for 5 minutes after temperature rise so that intracellular temperature and extracellular temperature were constant, and the fluorescence intensity at each temperature was measured.

Figure 23:
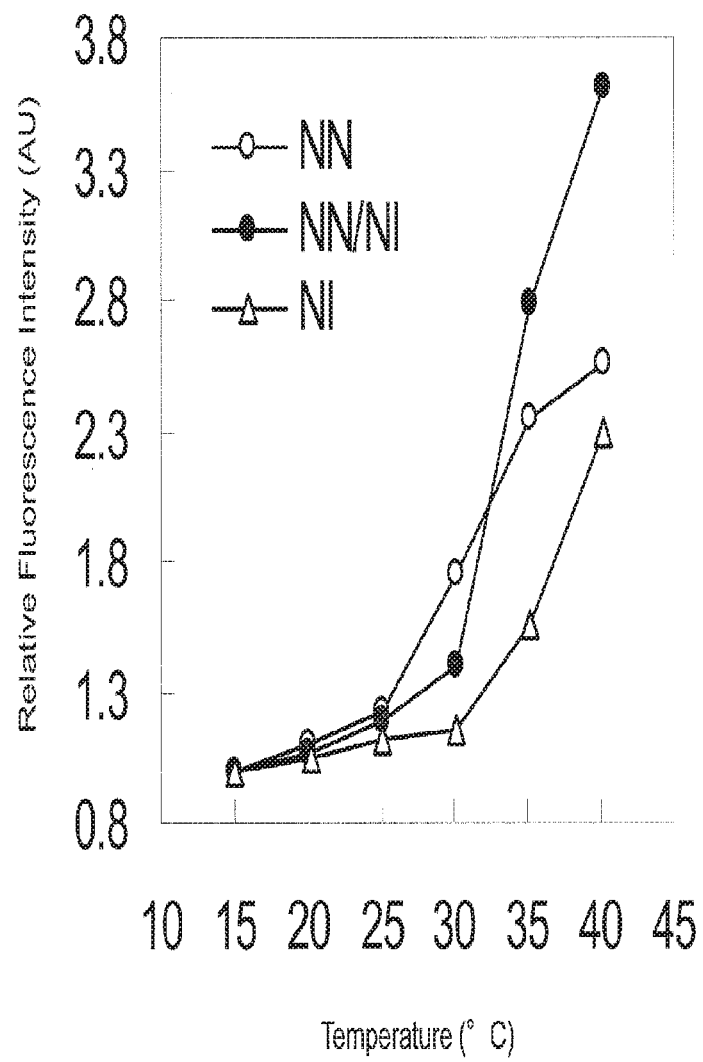
FIG. 23 is an example of thermoresponsivity test results of the fluorescence intensities of compounds 2, 9, and 10 in yeast cells (white circle: compound 2, black circle: compound 9, white triangle: compound 10).

The measurement results are shown in FIG. 23. For the results, the fluorescence intensity at 10° C. was defined as 1, and the longitudinal axis was represented by relative fluorescence intensity. The fluorescence wavelength when the maximum fluorescence intensity of each compound was recorded was used. It was revealed that the fluorescence intensity was changed in the range of 25° C. to 35° C. when a thermoresponsive site was NNPAM, changed in the range of 30° C. to 40° C. in the case of NNPAM/NIPAM, and changed at 35° C. or more in the case of NIPAM alone. Although it was clear from FIG. 22 that the temperature-responsive region can be changed in a solution, it could be demonstrated that the thermoresponsive site can be freely changed depending on an intracellular temperature region to be measured without not largely changing its responsive region also in a cell.

Example 32: Thermoresponsivity Test on Changes in Fluorescence Lifetime

Using a yeast cell suspension containing compounds 2, 9, and 10 prepared in Example 31, a thermoresponsivity test of change in fluorescence lifetime was performed. A Fluoro-Cube 3000U (Horiba Jobin Yvon) time correlation single photon counting method fluorescence lifetime measurement device was used, and the excitation wavelength was 456 nm. For excitation of the solution, using LED (NanoLED-456, Horiba), measurement was performed at a pulse repetition rate of 1 MHz. A JASCO ETC-273T water-cooled Peltier thermostated cell holder was used for temperature control of the solution, and temperature in the cell holder was measured with its accompanying thermometer. After temperature in the solution was confirmed to be stable with a thermocouple before measurement, the fluorescence lifetime at each temperature was measured with a fluorescence wavelength of 560 nm. The fluorescence decay curve obtained was approximated with the following formula, and fluorescence lifetime of two components was obtained.

$I(t)=A+B_1 \exp(-t/\tau_1)+B_2 \exp(-t/\tau_2)$

From the fluorescence lifetime thus obtained, mean fluorescence lifetime at each temperature was calculated by the following equation:

$$<\tau_f> = \frac{B_1\tau_1 + B_2\tau_2}{B_1 + B_2}$$

Figure 24:
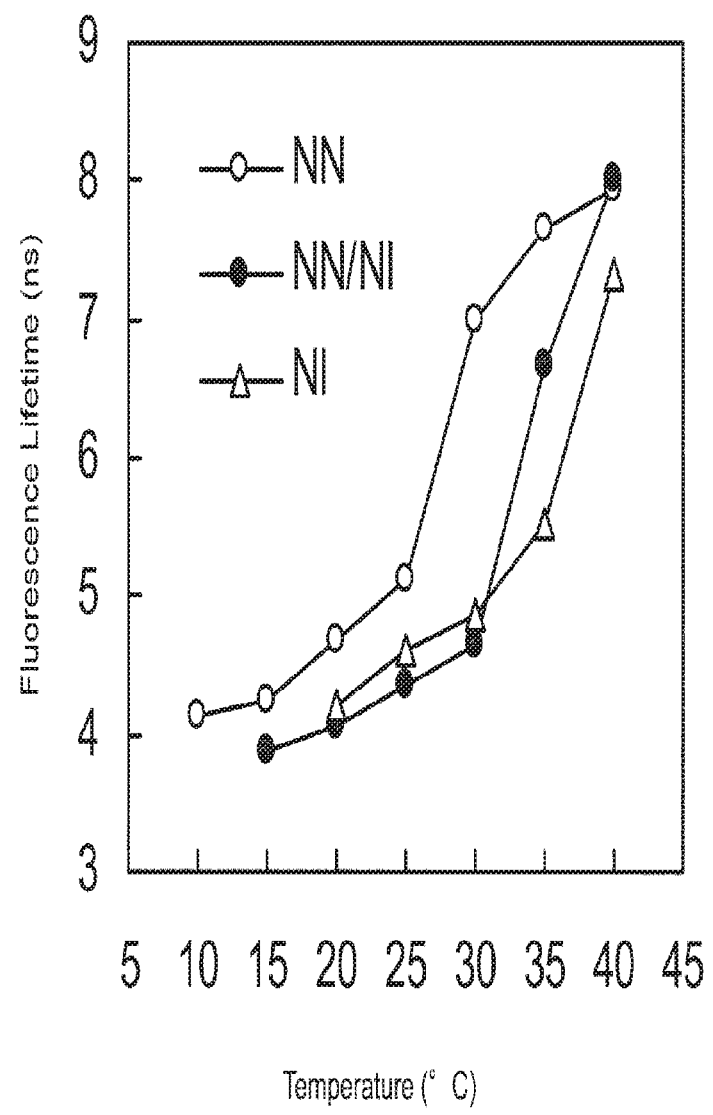
FIG. 24 is an example of thermoresponsivity test results of the fluorescence lifetimes of compound 2, 9, and 10 in yeast cells (white circle: compound 2, black circle: compound 9, white triangle: compound 10).

The test results are shown in FIG. 24. Similar to the results of Example 31, it was revealed that the fluorescence lifetime was changed in the range of 25° C. to 35° C. when a thermoresponsive site was NNPAM, changed in the range of 30° C. to 40° C. in the case of NNPAM/NIPAM, and changed at 35° C. or more in the case of NIPAM alone. It was confirmed that mean fluorescence lifetime is prolonged with higher temperature, and that mean fluorescence lifetime is changed sensitively responding to change in temperature.

Example 33: Probe Introduction into Cultured Cells (Non-Adherent Cells)

MOLT-4 cell (human acute lymphoblastic leukemia (T cell)) was incubated in a RPMI 1640 medium (10% FBS) and a 100 mm dish (seeded 1×10$^6$ cells/ml). After one day, 3 ml of the culture solution was centrifuged (1,000 rpm, 1 minute), and the medium was removed and the cell was washed with 5% glucose. Then, the cell was suspended in 1 ml of 5% glucose again, and compound 2 was added so that the final concentration was 0.05%. At 15° C., after 10 minutes, the solution was centrifuged, the supernatant was removed, and the cell was washed with PBS, and then the cell was suspended in PBS to confirm whether the probe is introduced by microscopy. Microscopy was performed with a confocal laser scanning microscope (FV1000, Olympus) and a 60× oil-immersion objective lens (UplanSApo N.A.1.40, Olympus). A laser (Multi Ar laser) of 473 nm was applied to the cell, and fluorescent images for fluorescence wavelengths ranging from 500 nm to 600 nm were observed.

Figure 25:
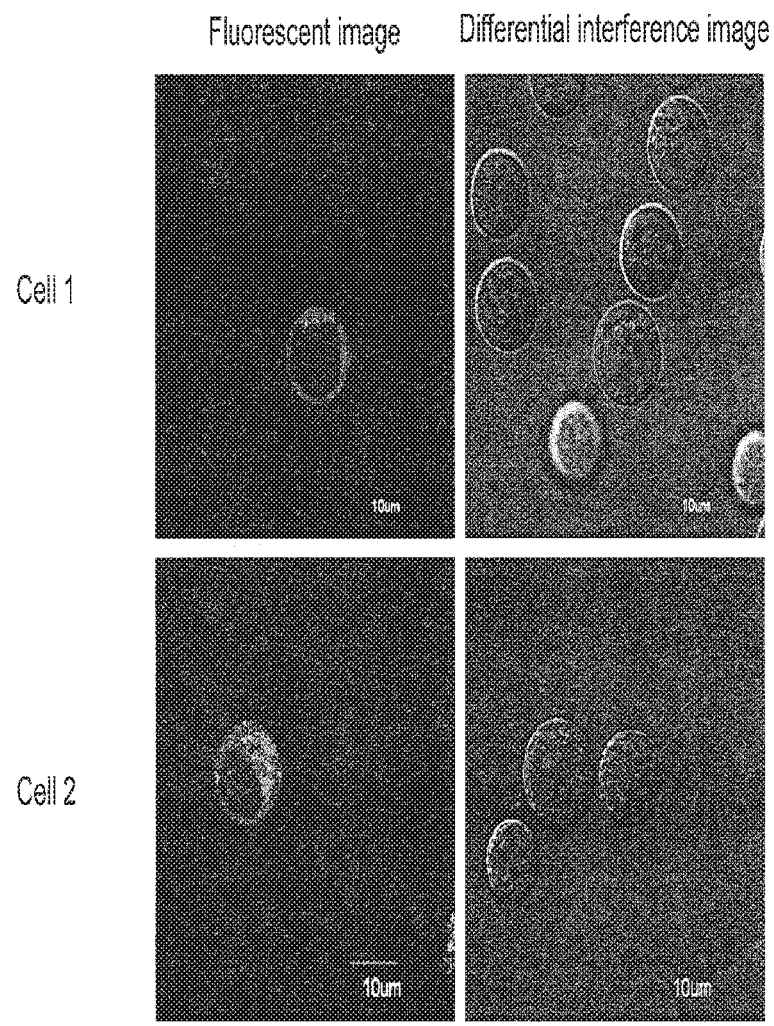
FIG. 25 is an example of photographs when compound 2 was mixed with non-adherent MOLT-4 cells, and observed by a confocal laser scanning microscope (excitation wavelength of 473 nm, fluorescence wavelength of 500-600 nm).

The results are shown in FIG. 25. Probe introduction could be confirmed also in MOLT-4, a non-adherent cell.

Example 34: Fluorescence Intensity Response of Compounds 9 and 10 in Cultured Cells (Non-Adherent Cells)

In the same manner as in Example 33, compounds 2, 9, and 10 were introduced into MOLT-4 cell. While suspended in PBS, the cell was put into a cuvette, and a spherical stirrer with a diameter of 2 mm was put into the cuvette. The cuvette was placed in a JASCO FP-6500 spectrofluorometer and rotated at a speed of about 800 rpm to prevent sinking of the cell, and fluorescence spectrum was measured. The excitation wavelength was 456 nm. A JASCO ETC-273T water-cooled Peltier thermostated cell holder was used for temperature control of the solution, and temperature in the cell holder was measured with its accompanying thermometer. Solution temperature was raised in steps of 5° C., the solution was incubated for 5 minutes after temperature rise so that intracellular temperature and extracellular temperature were constant, and the fluorescence intensity at each temperature was measured.

Figure 26:
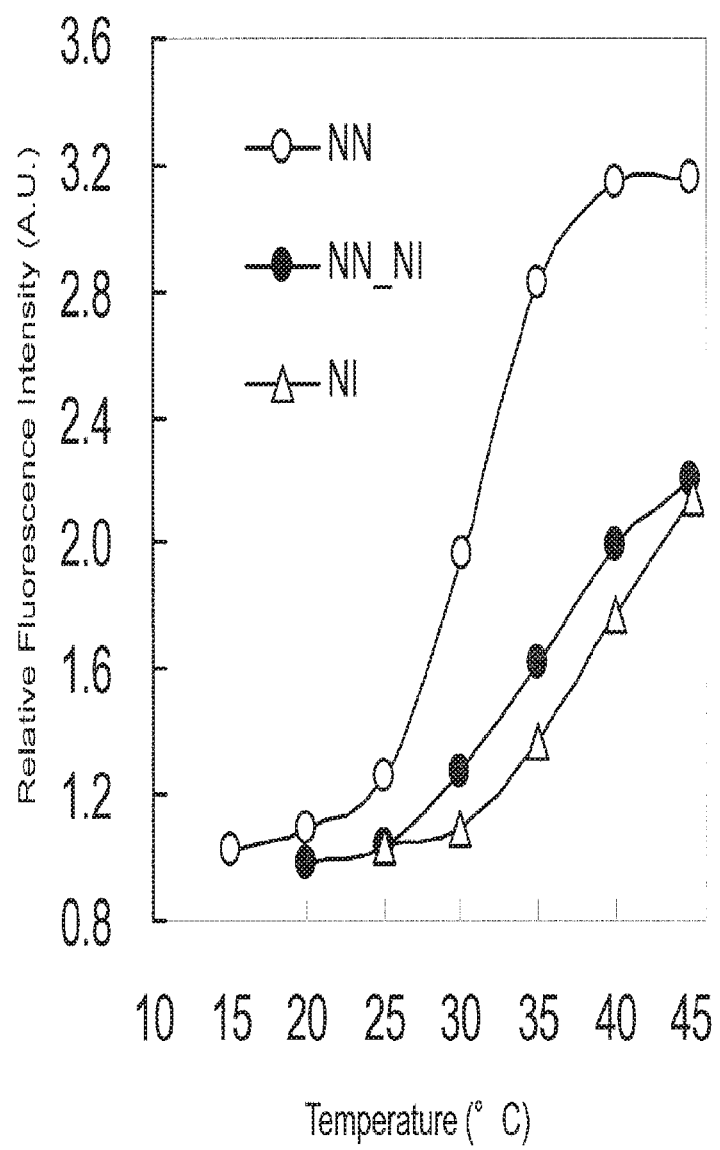
FIG. 26 is an example of thermoresponsivity test results of the fluorescence intensities of compounds 2, 9, and 10 in cultured cells (MOLT-4, non-adherent cell) (white circle: compound 2, black circle: compound 9, white triangle: compound 10).

The results are shown in FIG. 26. It was revealed that intracellular response was observed in NNPAM, NNPAM/NIPAM, and NIPAM in the order of lowest to highest temperature region. This is similar to the experimental results of the yeast in Example 31, and it was indicated that a thermoresponsive unit corresponding to targeted measurement temperature can be selected and measured also in cultured cells.

Example 35: Fluorescence Lifetime Response of Compounds 9 and 10 in Cultured Cells (Non-Adherent Cells)

Using MOLT-4 cells into which compound 2, 9, or 10 were introduced prepared as in Example 33, fluorescence lifetime was measured. Measurement was performed while the cell was suspended in PBS, and the measurement methods are exactly the same as in Example 32.

Figure 27:
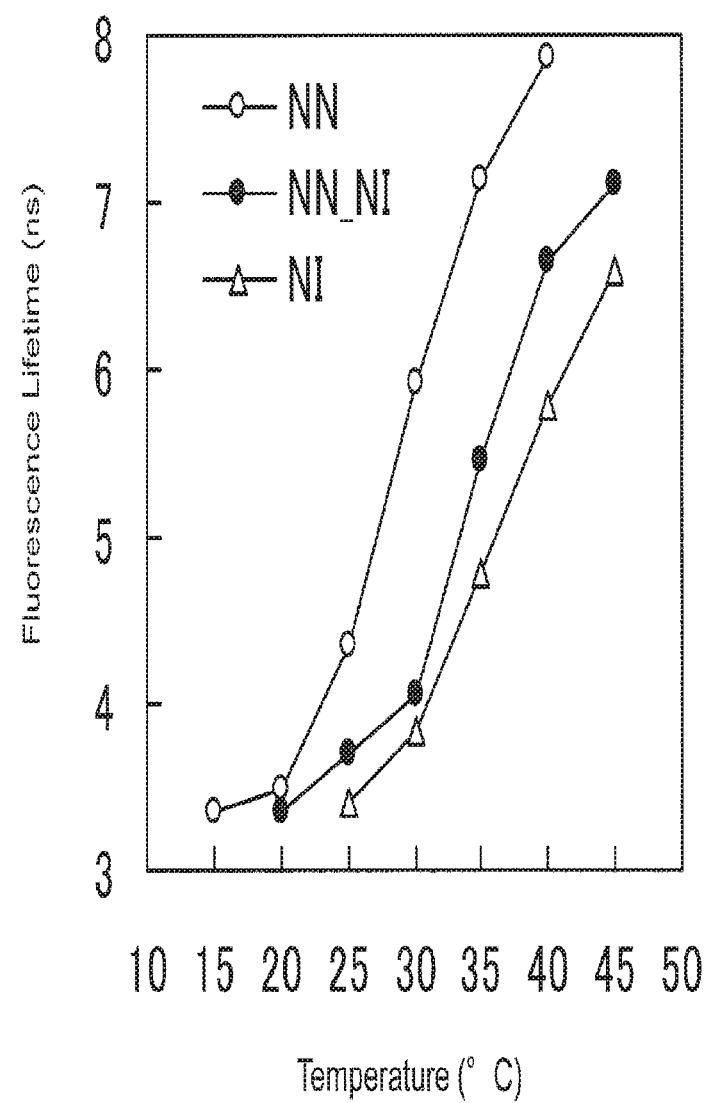
FIG. 27 is an example of thermoresponsivity test results of the fluorescence lifetimes of compounds 2, 9, and 10 in cultured cells (MOLT-4, non-adherent cell) (white circle: compound 2, black circle: compound 9, white triangle: compound 10).

The results are shown in FIG. 27. Similar to FIG. 26, it was revealed that intracellular response was observed in NNPAM, NNPAM/NIPAM, and NIPAM in the order of lowest to highest temperature region. Together with the results of Example 34, it was strongly indicated that a thermoresponsive unit corresponding to targeted measurement temperature can be selected and measured also in cultured cells.

Example 36: Effects of Compounds 9 and 10 in Microscopy

HEK293T was incubated in a DMEM medium (10% FBS, 1% penicillin-streptomycin) and a 35 mm glass bottom dish (seeded 1×10$^6$ cells/ml). After one day, the medium was replaced with 5% glucose, and compound 2, 9, or 10 was added so that the final concentration was 0.05%. At 15° C., after 10 minutes, the cell was washed with PBS, and then the medium was replaced with a phenol red-free medium, and microscopy was performed. The microscopy was performed with a confocal laser scanning microscope (FV1000, Olympus) and a 60× oil-immersion objective lens (UplanSApo N.A.1.40, Olympus). A laser (Multi Ar laser) of 473 nm was applied to the cell, and fluorescent images for fluorescence wavelengths ranging from 500 nm to 600 nm were observed.

Figure 28:
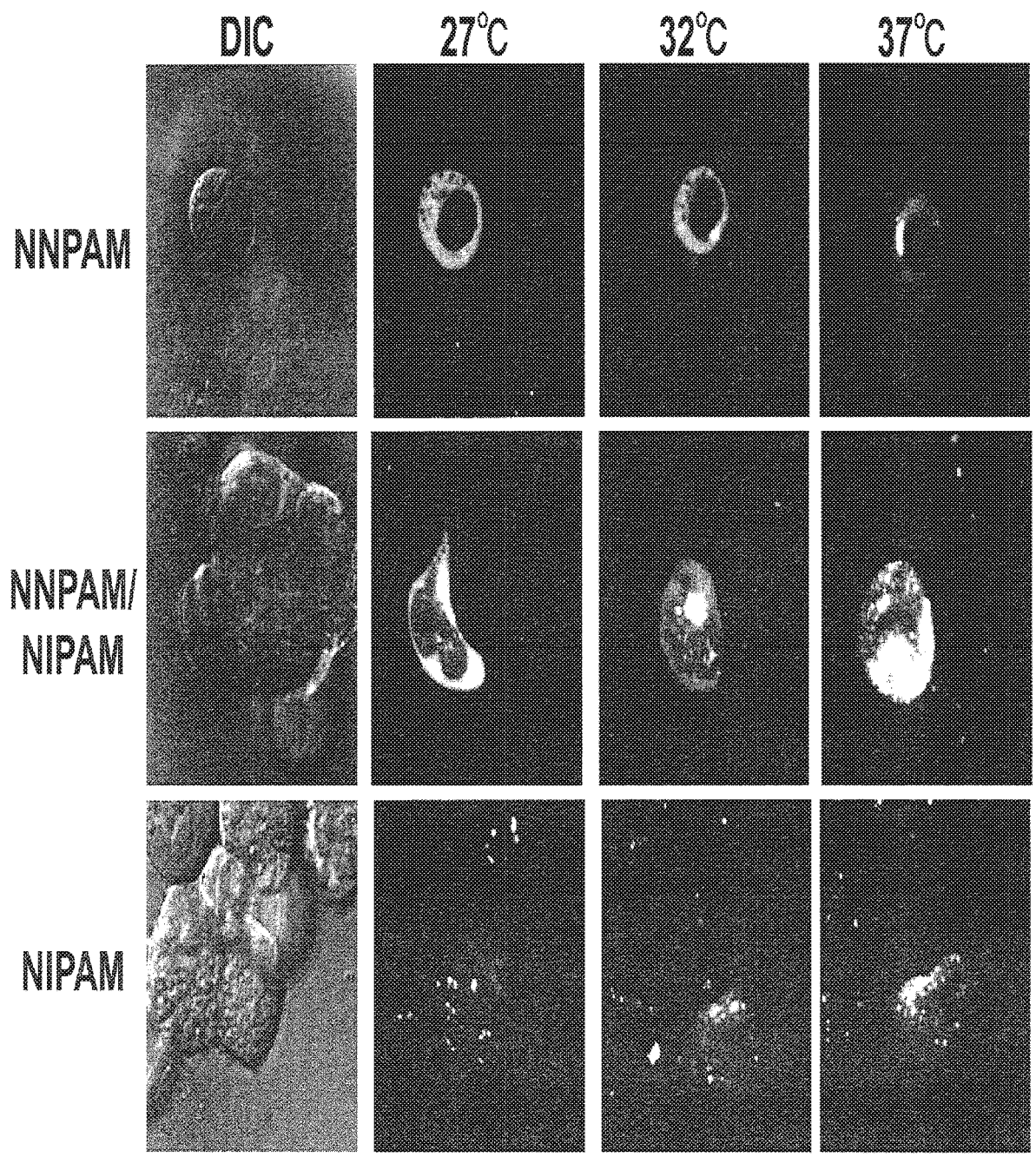
FIG. 28 is an example of photographs when compound 2, 9, or 10 was mixed with an HEK293T cell and observed by a confocal laser scanning microscope (excitation wavelength of 473 nm, fluorescence wavelength of 500-600 nm).

The results are shown in FIG. 28. It was revealed also by microscopy that when NNPAM was used for a thermoresponsive unit, increased fluorescence intensity at about 37° C., which is an optimal proliferation temperature of cells, was less observed, while when NNPAM/NIPAM was used, a strong fluorescence response at about 37° C. was seen. It was expected that use of NIPAM enables measurement of a higher measurement region. Based on the results, it was indicated also by microscopy that a different thermoresponsive unit can be used.

Example 37: Effects of Compound 9 in Microscopy (Ratiometric Measurement Using Ratio of Fluorescence Intensity)

Using a sample of HEK293T into which compound 9 was introduced as in Example 36, a ratio of fluorescence intensity was measured, and whether the temperature can be measured independent of fluorescence intensity was investigated. Microscopy was performed with a confocal laser scanning microscope (FV1000, Olympus) and a 60× oil-immersion objective lens (UplanSApo N.A.1.40, Olympus). A laser (Multi Ar laser) of 473 nm was applied to the cell. Fluorescent images for fluorescence wavelengths ranging from 500 nm to 550 nm (CH1), fluorescent images for fluorescence wavelengths ranging from 600 nm to 650 nm (CH2), and ratio images obtained by dividing the fluorescence intensity of CH1 by the fluorescence intensity of CH2 were observed.

Figure 29:
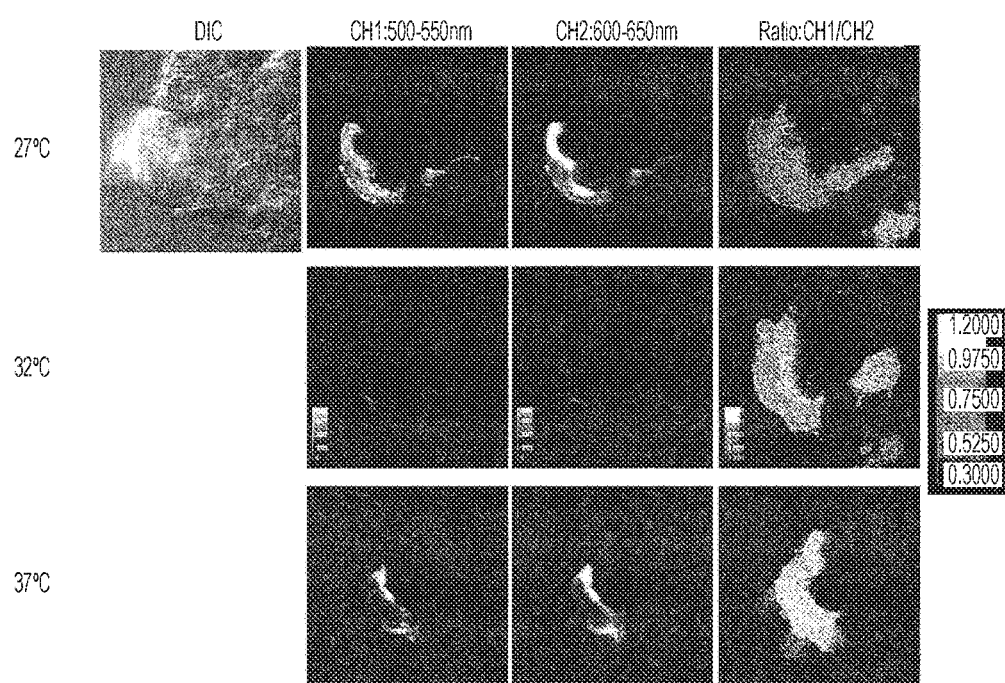
FIG. 29 is an example of fluorescent images (ratio: CH1/CH2) obtained by introducing compound 9 into an HEK293T cell to be observed by a confocal laser scanning microscope (excitation wavelength of 473 nm), and by calculating a ratio between fluorescent images at a fluorescence wavelength of 500-550 nm (CH1) and fluorescent images at a fluorescence wavelength of 600-650 nm (CH2).

The results are shown in FIG. 29. Even in cells in which the fluorescence intensity seems not to be simply increased by only CH1 and CH2, by calculating its ratio, it became clear that the ratio was increased, and thus it was clearly indicated that temperature was raised.

B. Study on Ratiometric Temperature-Sensitive ProbeReagent and Data Measurement

After purifying by recrystallization with methanol, α,α'-azobisisobutyronitrile (AIBN) was used. After purifying by recrystallization with n-hexane, N-isopropylacrylamide (NIPAM) was used. Regarding other reagents, purchases were used without being purified.

Using a BRUKER AVANCE 400 spectrometer (400 MHz), $^1$H-NMR was measured and chemical shift was indicated by ppm. Using a JASCO GPC system (JASCO PU-2080 pump, JASCO RI-2031 differential refractometer, JASCO CO-2060 column oven, Shodex GPC KD-806M column), the number average molecular weight and weight average molecular weight were calculated by using a calibration curve obtained from a polystyrene standard sample. In silica gel column chromatography, Kanto Chemical silica gel 60N (40-50 μm) was used. In the measurement of an absorbance, a JASCO V-550 ultraviolet visible light spectrophotometer was used.

Example B1-1: Synthesis of 8-(4-acrylamidephenyl)-4,4-difluoro-1,3,5,7-tetramethyl-4-bora-3a,4a-diaza-s-indacene (BODIPY-AA)

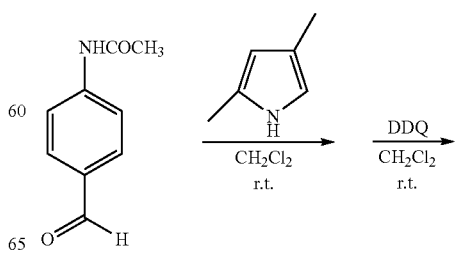

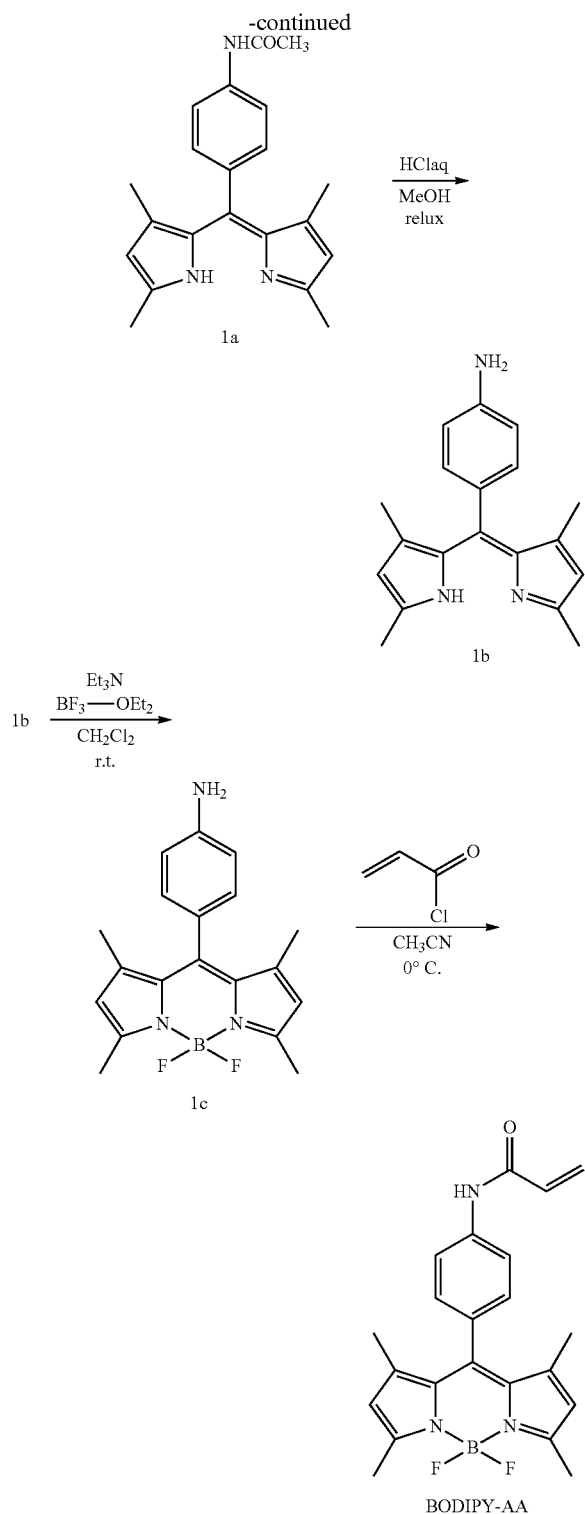

Under argon atmosphere, 4-acetamidebenzaldehyde (200 mg, 1.23 mmol), and 2,4-dimethylpyrrole (253 μL, 2.45 mmol) were dissolved in dichloromethane (70 mL, dehydrated with molecular sieves 4A) and one droplet of trifluoroacetic acid was added, followed by stirring at room temperature for 6 hours. To this reaction solution, a suspension prepared by suspending 2,3-dichloro-5,6-dicyano-1,4-benzoquinone (DDQ) (278.3 mg, 1.23 mmol) in dichloromethane (5 mL, dehydrated with molecular sieves 4A) was added and a vessel was washed with 3 mL of dichloromethane, and then the wash was also added. After stirring at room temperature for 30 minutes, the reaction solution was washed in turn with water (100 mL×2) and saturated brine, and then the solvent was distilled off by drying over $Na_2SO_4$. The crude product thus obtained was purified by alumina chromatography (dichloromethane→dichloromethane:methanol=100:1-50:1 for the first time, dichloromethane→dichloromethane:methanol=100:1 for the second time, and dichloromethane:methanol=200:1 for the third time) to obtain the objective product (compound 1a) as a pale brown crystal (31 mg, 7.5%).

1H NMR (400 MHz, $CDCl_3$) of the compound 1a is as follows.

δ7.61 (d, 2H, J=8.4 Hz), 7.29 (br, 1H), 7.24 (d, 2H, J=8.4 Hz), 5.89 (s, 2H), 2.34 (s, 6H), 2.21 (s, 3H), 1.34 (s, 6H).

The compound 1a thus obtained (66 mg, 0.20 mmol) was dissolved in 10 mL of methanol and 10 mL of 1N hydrochloric acid was added, followed by heating at reflux for 4 hours. After cooling to room temperature, the reaction solution was neutralized with a 2N NaOH solution. After extracting with dichloromethane (100 mL×3), the organic layer was washed in turn with water and saturated brine and then the solvent was distilled off by drying over $Na_2SO_4$. The crude product thus obtained was purified by alumina chromatography (dichloromethane:methanol=20:1) to obtain the objective product (compound 1b) as a pale brown crystal (46 mg, 79%).

1H NMR (400 MHz, $CDCl_3$) of the compound 1b is as follows.

δ7.05-7.03 (m, 2H), 6.75-6.73 (m, 2H), 5.89 (s, 2H), 3.76 (br, 2H), 2.34 (s, 6H), 1.42 (s, 6H)

Under argon atmosphere, the compound 1b (20 mg, 0.069 mmol) was dissolved in 25 mL of dichloromethane, and then triethylamine (200 μL), boron trifluoride-ethylether complex (200 μL) was added thereto in this order, followed by stirring at room temperature for 2 hours. The reaction solution was poured into 80 mL of water, thereby terminating the reaction, and then the solution was made alkaline by adding a 2N NaOH solution. After extracting with dichloromethane, the organic layer was washed with saturated brine and then the solvent was distilled off by drying over $Na_2SO_4$. The crude product thus obtained was purified by alumina chromatography (dichloromethane:hexane=1:1) to obtain the objective product (compound 1c) as a red crystal (22 mg, 96%).

1H NMR (400 MHz, $CDCl_3$) of the compound 1c is as follows.

δ7.02-7.00 (m, 2H), 6.79-6.77 (m, 2H), 5.97 (2H), 3.83 (br, 2H), 2.55 (s, 6H), 1.50 (s, 6H).

13C NMR (100 MHz, $CDCl_3$) of the compound 1c is as follows.

δ155.0, 147.0, 143.2, 142.6, 132.0, 129.0, 124.7, 120.9, 115.4, 14.6, 14.5.

The compound 1c (10 mg, 0.029 mmol) was dissolved in 2 mL of acetonitrile and triethylamine (4.1 μL, 0.029 mmol) was added, and then acrylic acid chloride (3.1 μL, 0.038 mmol) was added at 0° C. After stirring at room temperature for 2 hours, $K_2CO_3$ was added and a salt was filtered. The filtrate was distilled off and the crude product thus obtained was purified by silica gel chromatography (dichloromethane:hexane=3:1→100% dichloromethane) to obtain the titled compound (BODIPY-AA) as an orange crystal (11 mg, 97%).

The results of 1H NMR (400 MHz, methanol-d4) of BODIPY-AA are as follows.

δ7.88-7.86 (m, 2H), 7.31-7.29 (m, 2H), 6.51-6.37 (m, 2H), 6.07 (s, 2H), 5.81 (dd, 1H, J=2.4, 9.6 Hz), 2.49 (s, 6H), 1.48 (s, 6H).

The results of 13C NMR (100 MHz, CDCl$_3$) of BODIPY-AA are as follow.

δ163.5, 155.5, 143.1, 141.1, 138.6, 131.6, 130.9, 128.8, 128.5, 121.2, 120.1, 14.6.

Example B1-2: Synthesis of 4,4-difluoro-8-(4-isobutylamidephenyl)-1,3,5,7-tetramethyl-4-bora-3a,4a-diaza-s-indacene (BODIPY-IA)

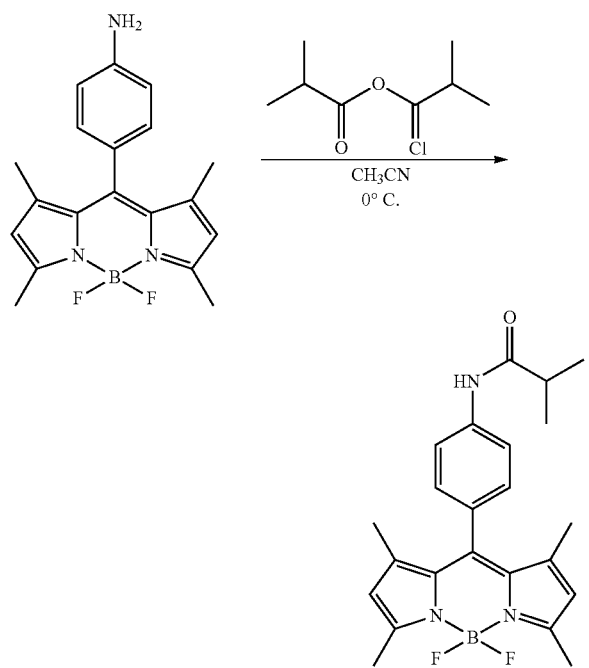

The compound 1c (10 mg, 0.029 mmol) synthesized in Example B1-1 was dissolved in 1 mL of acetonitrile, and then triethylamine (4.9 µL, 0.035 mmol) and isobutyric anhydride (7.4 µL, 0.044 mmol) were added in this order at 0° C., followed by stirring at room temperature for 3 hours. Furthermore, triethylamine (4.9 µL, 0.035 mmol) and isobutyric anhydride (7.4 µL, 0.044 mmol) were added, followed by stirring for 30 minutes, stirring at 40° C. for 2 hours, stirring at 50° C. for 3 hours, and further stirring overnight at room temperature. To this reaction solution, Na$_2$SO$_4$ was added and the solution was filtered. The filtrate was distilled off under reduced pressure and the crude product thus obtained was purified by silica gel chromatography (dichloromethane) to obtain the objective product as a red crystal (12 mg, 95%).

The results of 1H NMR (400 MHz, CDCl$_3$) of BODIPY-IA are as follows.

δ7.69 (d, 2H, J=8.2 Hz), 7.31 (br, 1H), 7.22 (d, 2H, 8.2 Hz), 5.98 (s, 2H), 2.55 (s, 6H), 1.43 (s, 6H), 1.29 (d, 6H, J=6.8 Hz), 1.25 (br, 1H).

The results of 13C NMR (100 MHz, CDCl$_3$) of BODIPY-IA are as follows.

δ175.3, 155.5, 143.1, 141.3, 138.9, 131.6, 130.5, 128.8, 121.2, 119.9, 36.9, 19.6, 14.64, 14.56.

Example B1-3: Calculation of Quantum Yield Varying Depending on Solvent of BODIPY-IA BODIPY-IA synthesized in Example B1-2 was dissolved in acetonitrile, methanol, hexane, ethyl acetate, and 75 v/v % water-25 v/v % dioxane, respectively in each concentration of 10 µM, and then an absolute fluorescence quantum yield was calculated using fluorophotometer FP8500 (JASCO Corporation) equipped with an integrating sphere unit ILF835. For the excitation wavelength, 470 nm was selected. An incident light area $S_0$ in a state where a sample is absent, a sample scattered light area S1, and a peak area $S_2$ of fluorescence wavelength were calculated, and then calculation was performed using the following equation.

Quantum yield=$S_2/(S_0-S_1)\times 100$

The results are shown in Table B1.

TABLE B1

| Solvent | Acetonitrile | Methanol | Hexane | Ethyl acetate | 75% water-25% dioxane |
|---|---|---|---|---|---|
| Quantum yield | 0.38 | 0.39 | 0.35 | 0.42 | 0.53 |

As is apparent from the results of Table B1, a BODIPY-AA fluorescence unit used newly in a temperature-sensitive probe exhibits a tendency that the quantum yield is decreased in a hydrophobic environment such as acetonitrile, while the quantum yield is increased in water. When this unit is incorporated into an acrylamide polymer, the surrounding BODIPY-AA is subjected to a hydrophilic environment and thus fluorescence quantum yield is increased, leading to generation of comparatively strong fluorescence at low temperature (in water) (in a state where acrylamide chains are in the form of strings), while the surrounding BODIPY-AA is subjected to a hydrophobic environment and thus fluorescence quantum yield is decreased, leading to generation of comparatively weak fluorescence at high temperature (in a state where acrylamide chains are aggregated). It is known that the fluorescence intensity increases with a rise in temperature in a fluorescence temperature sensor using a fluorescent pigment having a benzofurazan skeleton. Namely, it was assumed that use of both BODIPY and a fluorescent pigment having a benzofurazan skeleton enables detection of a change in fluorescence intensity depending on a change in temperature with satisfactory sensitivity.

Example B3: Synthesis of N-(2-{[7-(N,N-dimethylaminosulfonyl)-2,1,3-benzothiadiazol-4-yl]-(methyl)amino}ethyl)-N-methylacrylamide (DBThD-AA)

Synthesis was performed in accordance with the method disclosed in Document A (Chemistry A European Journal 2012; 18: 9552-563). After dissolving 3-chloro-1,2-phenylenediamine in toluene, N-thionylaniline was added. After heating at reflux at 130° C. for 3 hours, the solution was evaporated to dryness under reduced pressure and then purified by silica gel chromatography to obtain 4-chloro-2,1,3-benzothiadiazole. The product thus obtained was dissolved in concentrated sulfuric acid at 0° C., followed by stirring at 0° C. for 1 hour and a half, heating to 150° C., and further stirring for 2 hours and a half. After completion of the reaction, the reaction solution was poured into ice water, followed by extraction with dichloromethane. The organic layer was dried over $Na_2SO_4$, evaporated to dryness under reduced pressure, and then purified by silica gel chromatography to obtain 7-chloro-2,1,3-benzothiadiazole-4-sulfonyl chloride.

Furthermore, the substance thus obtained was dissolved in dichloromethane and then an aqueous dimethylamine solution dissolved in acetonitrile was added. After reacting at room temperature for 30 minutes, the reaction solution was evaporated to dryness under reduced pressure and then purified by silica gel chromatography to obtain 7-chloro-N,N-dimethyl-2,1,3-benzothiadiazole-4-sulfonamide. This substance was dissolved in acetonitrile and this solution was added to N,N'-dimethylethylenediamine. After reacting at 80° C. for 1 hour, the reaction solution was evaporated to dryness under reduced pressure and then purified by silica gel chromatography to obtain N,N-dimethyl-7-[methyl{2-(methylamino)ethyl}amino]-2,1,3-benzothiadiazole-4-sulfonamide.

The thus obtained N,N-dimethyl-7-[methyl{2-(methylamino)ethyl}amino]-2,1,3-benzothiadiazole-4-sulfonamide was dissolved in acetonitrile, and triethylamine (1 eq) and acrylic acid chloride (1.3 eq) were added at 0° C., followed by stirring at 0° C. for 1 hour. To the reaction solution, $Na_2CO_3$ (1 g) was added. After filtration, the filtrate was evaporated to dryness under reduced pressure and then purified by silica gel column chromatography (using dichloromethane/methanol as a developing solvent) to obtain the titled compound DBThD-AA as an orange crystal.

Example B4: Production of N-n-propylacrylamide/(3-acrylamidepropyl)trimethylammonium/N-{2-[(7-N,N-dimethylaminosulfonyl)-2,1,3-benzoxadiazol-4-yl](methyl)amino}ethyl-N-methylacrylamide/BODIPY-AA Copolymer NNPAM (543 mg, 4.8 mmol), (3-acrylamidepropyl)trimethylammonium chloride (55.1 mg, 0.2 mmol, hereinafter also referred to as "APTMA chloride"), DBThD-AA (9.59 mg, 25 μmol), BODIPY-AA (1.97 mg, 5 μmol), and AIBN (8.21 mg, 50 μmol) were dissolved in DMF (10 ml), and then dissolved oxygen was removed by passing through an argon gas for 30 minutes. Thereafter, the mixture was reacted at 60° C. for 4 hours and then cooled to room temperature. This solution was poured into diethylether (300 ml) while stirring. The crystal thus obtained was collected by filtration, dried under reduced pressure and dissolved in MeOH (1 mL), thereby causing reprecipitation, and then the precipitate was dissolved in pure water. Using a Visking tube having a diameter of 28.6 mm (cellulose tube for dialysis), the solution was purified by dialyzing well with 1,000 ml of a dialysis outer liquid. The purified product was freeze-dried to obtain the titled copolymer as a pale yellow powder (254.4 mg, 42%).

The number average molecular weight was 4,537 and the weight average molecular weight was 9,264, and a composition ratio of each unit in a copolymer was as follows: NNPAM:APTMA:DBThD-AA:BODIPY-AA=94.5:5.5:0.579:0.071. The proportions of a NNPAM unit and an APTMA unit in a copolymer was calculated from an integrated value in the $^1$H-NMR measurement, and the proportion of a DBThD-AA unit was calculated by comparing an absorbance in methanol with 4-N,N-(dimethylamino)-7-N,N-dimethylaminosulfonyl-2,1,3-benzothiadiazole. The proportion of a BODIPY-AA unit was calculated by comparing an absorbance in methanol with BODIPY-IA.

Example B5: Production of Copolymer in which Temperature-Sensitive Unit is Changed Using NIPAM and N-tert-butylacrylamide (NTBAM), which respectively cause a structural change at the temperature lower and higher than that in NNPAM as a temperature-sensitive unit used in Example B4, a copolymer was synthesized. Lists of the synthesized compounds are shown in Table B2. In the same manner as in Example B4, synthesis was performed to obtain a pale yellow powder.

TABLE B2

| Copolymer | Compound B1 | Compound B2 | Compound B3 | Compound B4 |
| --- | --- | --- | --- | --- |
| Thermoresponsive unit (a) | NNPAM | NIPAM | NNPAM/NIPAM | NNPAM/NTBAM |
| Cationic unit (b) | APTMA | APTMA | APTMA | APTMA |
| Before reaction (a:b:DBThD unit:BODIPY unit) | 96:4:0.5:0.1 | 96:4:0.5:0.1 | 96 (48/48):4:0.5:0.1 | 96 (48/48):4:0.5:0.1 |
| After reaction (a:b:DBThD unit:BODIPY unit) | 94.5:5.5:0.579:0.071 | 94.5:5.5:0.545:0.069 | 94.5 (48.1/46.5):5.5:0.595:0.076 | 94.5 (52.8/41.7):5.5:0.656:0.073 |
| Yield amount (mg) | 254.4 | 52.4 | 52.0 | 57.7 |
| Yield (%) | 42 | 34 | 34 | 35 |
| Weight average molecular weight | 9,264 | 17,652 | 11,762 | 13,786 |
| Number average molecular weight | 4,537 | 8,628 | 5,038 | 6,883 |

As shown in Table B2, all objective copolymers could be synthesized. The composition ratio of the copolymer was calculated in the same manner as in Example B4, and also the molecular weight of the copolymer was calculated in the same manner as in Example B4. The proportions of a thermoresponsive unit and an APTMA unit in the copolymer were calculated from an integrated value in the $^1$H-NMR measurement, and regarding the proportions of a DBD-AA unit and a BODIPY-AA unit, an absorbance in methanol was calculated from molar extinction coefficients at 447 nm and 498 nm of 4-N,N-(dimethylamino)-7-N,N-dimethylamino-sulfonyl-2,1,3-benzothiadiazole and BODIPY-IA.

Example B6: Production of Copolymer in which Cationic Unit is Changed

A copolymer, using APTMA as the cationic unit used in Example B4 in the larger proportion, was produced. Also, a copolymer, using VBTMA in place of APTMA as a cationic unit which is a quaternary ammonium salt, was synthesized. Lists of synthesized compounds are shown in Table B3. Synthesis was performed by using the same technique as in Example B4, a pale yellow powder was obtained.

TABLE B3

| Copolymer | Compound B5 | Compound B6 |
|---|---|---|
| Thermoresponsive unit (a) | NNPAM | NNPAM |
| Cationic unit (b) | APTMA | VBTMA |
| Before reaction (a:b:DBThD unit:BODIPY unit) | 94:6:0.5:0.1 | 98:2:0.5:0.1 |
| After reaction (a:b:DBThD unit:BODIPY unit) | 90.7:9.3:0.614:0.076 | 94.5:5.5:0.705:0.112 |
| Yield amount (mg) | 56.0 | 14.1 |
| Yield (%) | 35 | 9.5 |
| Weight average molecular weight | 3,275 | 12,427 |
| Number average molecular weight | 2,050 | 5,161 |

As shown in Table B3, all objective copolymers could be synthesized. The composition ratio of the copolymer was calculated in the same manner as in Example B4, and also the molecular weight of the copolymer was calculated in the same manner as in Example B4. The proportions of a NNPAM unit and a cationic unit in the copolymer were calculated from an integrated value in the $^1$H-NMR measurement, and regarding the proportions of a DBD-AA unit and a BODIPY-AA unit, an absorbance in methanol was calculated from molar extinction coefficients at 447 nm and 498 nm of 4-N,N-(dimethylamino)-7-N,N-dimethylamino-sulfonyl-2,1,3-benzothiadiazole and BODIPY-IA.

Example B7: Production of Copolymer in which Fluorescent Unit Ratio is Changed A copolymer in which a ratio of two fluorescent units of the copolymer synthesized in Example B4 is changed was synthesized. Lists of synthesized compounds are shown in Table B4. Synthesis was performed by using the same technique as in Example B4, a pale yellow powder was obtained.

TABLE B4

| Copolymer | Compound B7 | Compound B8 |
|---|---|---|
| Thermoresponsive unit (a) | NNPAM | NNPAM |
| Cationic unit (b) | APTMA | APTMA |
| Before reaction (a:b:DBThD unit:BODIPY unit) | 96:4:0.5:0.25 | 94:4:0.5:0.05 |
| After reaction (a:b:DBThD unit:BODIPY unit) | 92.8:7.2:0.718:0.271 | 94.3:5.7:0.639:0.034 |
| Yield amount (mg) | 34.3 | 73.1 |
| Yield (%) | 22 | 47 |
| Weight average molecular weight | 6,804 | 9,904 |
| Number average molecular weight | 2,926 | 3,936 |

As shown in Table B4, all objective copolymer could be synthesized. The composition ratio of the copolymer was calculated in the same manner as in Example B4, and also the molecular weight of the copolymer was calculated in the same manner as in Example B4. The proportions of a NNPAM unit and an APTMA unit in the copolymer were calculated from an integrated value in the $^1$H-NMR measurement, and regarding the proportions of a DBD-AA unit and a BODIPY-AA unit, an absorbance in methanol was calculated from molar extinction coefficients at 447 nm and 498 nm of 4-N,N-(dimethylamino)-7-N,N-dimethylamino-sulfonyl-2,1,3-benzothiadiazole and BODIPY-IA.

Example B8: Thermoresponsivity Test

A thermoresponsivity test of compounds B1 to B8 in 150 mM KCl was performed by the following procedure. JASCO FP-6500 spectrofluorometer was used, and using ultrapure water obtained from Milli-Q reagent system made in Millipore Corporation, KCl purchased from Wako Pure Chemical Industries, Ltd. dissolved to make a 150 mM concentration was used as a solvent. The initial concentration of the compounds in this experiment was 0.01 w/v %, and the excitation wavelength was 458 nm. JASCO ETC-273T water-cooled Peltier thermostated cell holder was used for temperature control of the solution, and temperature was measured with its accompanying thermocouple. Solution temperature was raised in steps of 1° C. or 2° C., and the fluorescence spectrum of 450-850 nm at each temperature was measured.

Figure 30:
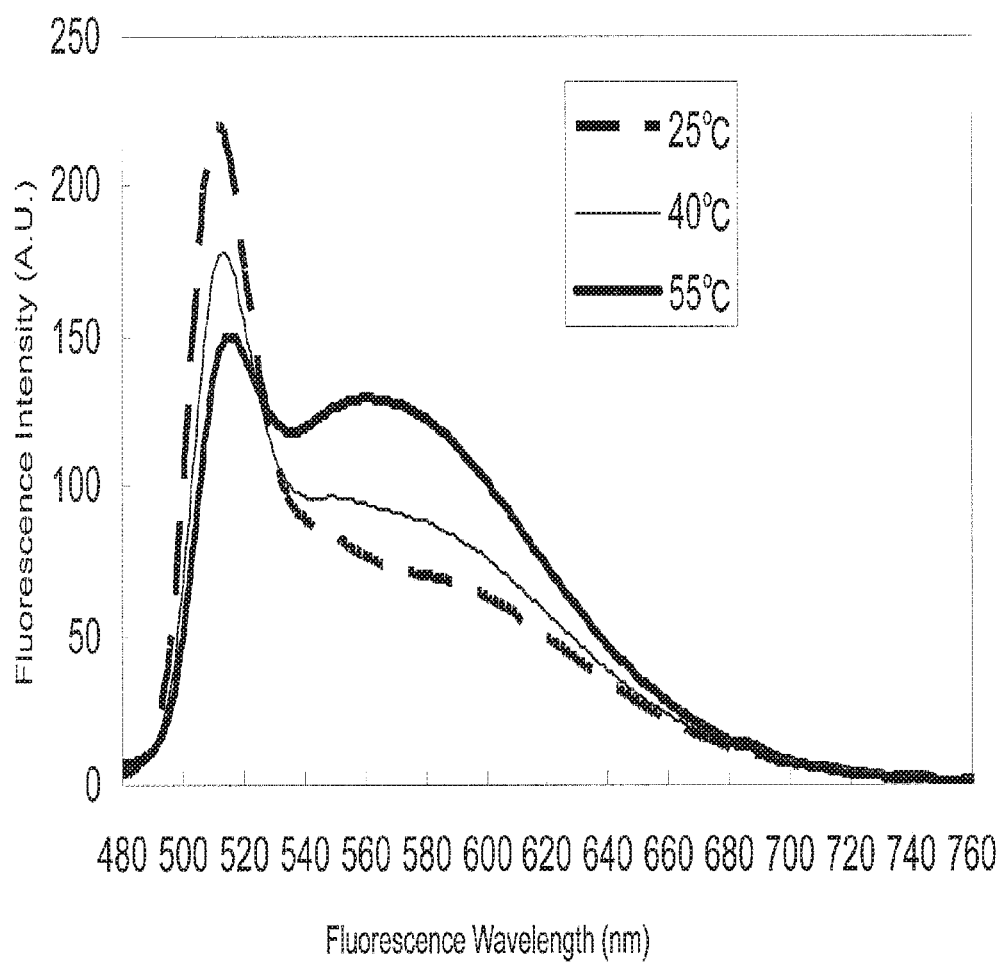
FIG. 30 is an example of change in fluorescence spectrum of compound B2 in an aqueous 150 mM potassium chloride solution (0.01 w/v %, excitation wavelength of 458 nm) at each temperature of 25° C. (dotted line), 40° C. (solid line), and 55° C. (thick line).

An example of change in spectrum when the temperature of compound B2 was changed is shown in FIG. 30. The results showed that in association with temperature rise, the fluorescence intensity at 500-520 nm, which is a fluorescence spectrum derived from BODIPY, was decreased and the fluorescence intensity at 540-600 nm, which is a fluorescence spectrum derived from DBThD, was increased. By calculating a ratio of these two wavelength regions, structural change of a copolymer with change in temperature can be grasped. In other words, it could be confirmed that the temperature surrounding the copolymer can be represented by a ratio of fluorescence intensity. The results of the change in spectrum revealed that by calculating a ratio of fluorescence intensities at 580 nm and 515 nm (FI580/FI510), change in ratio of fluorescence intensity for change in temperature become larger.

Figure 31:
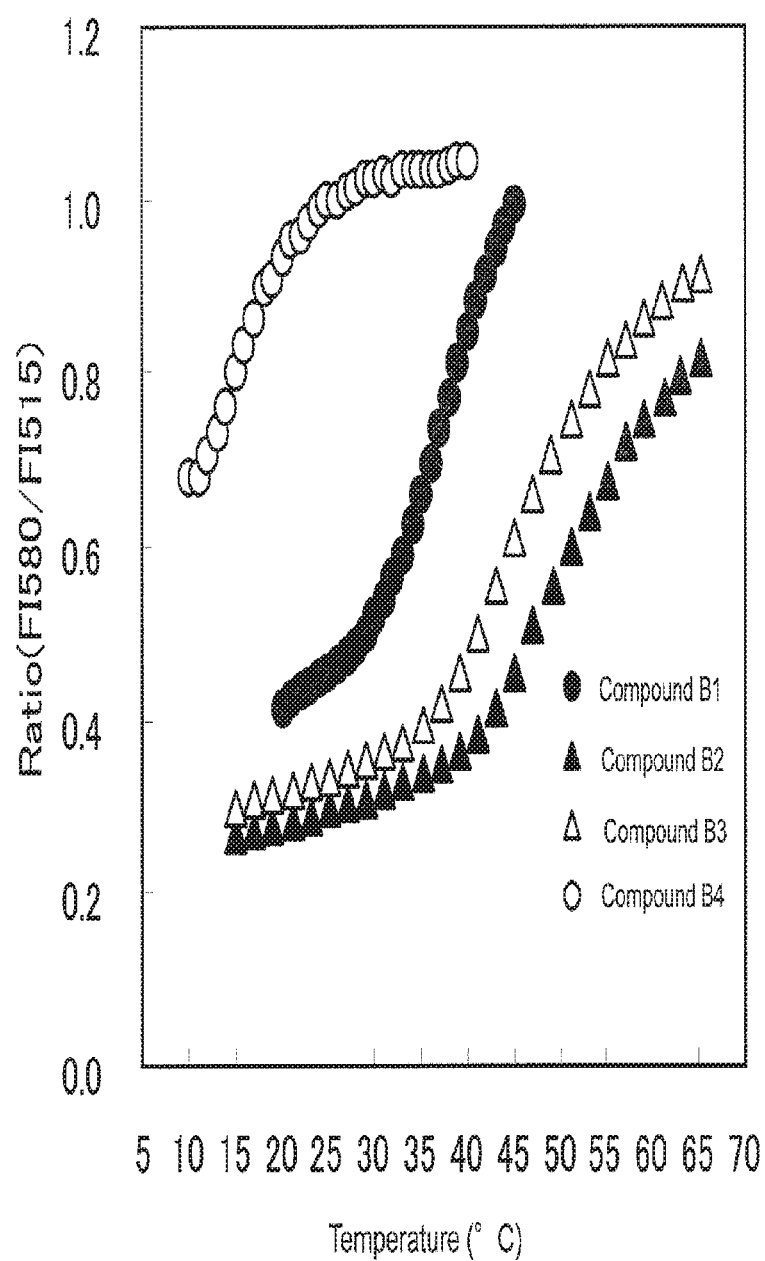
FIG. 31 is an example of thermoresponsivity test results (0.01 w/v %, excitation wavelength of 458 nm) of the ratio of fluorescence intensities (580 nm/515 nm) of compounds B1 to B4 (black circle: compound B1, black rhombus: compound B2, white triangle: compound B3, white circle: compound B4) in an aqueous 150 mM potassium chloride solution.
Figure 32:
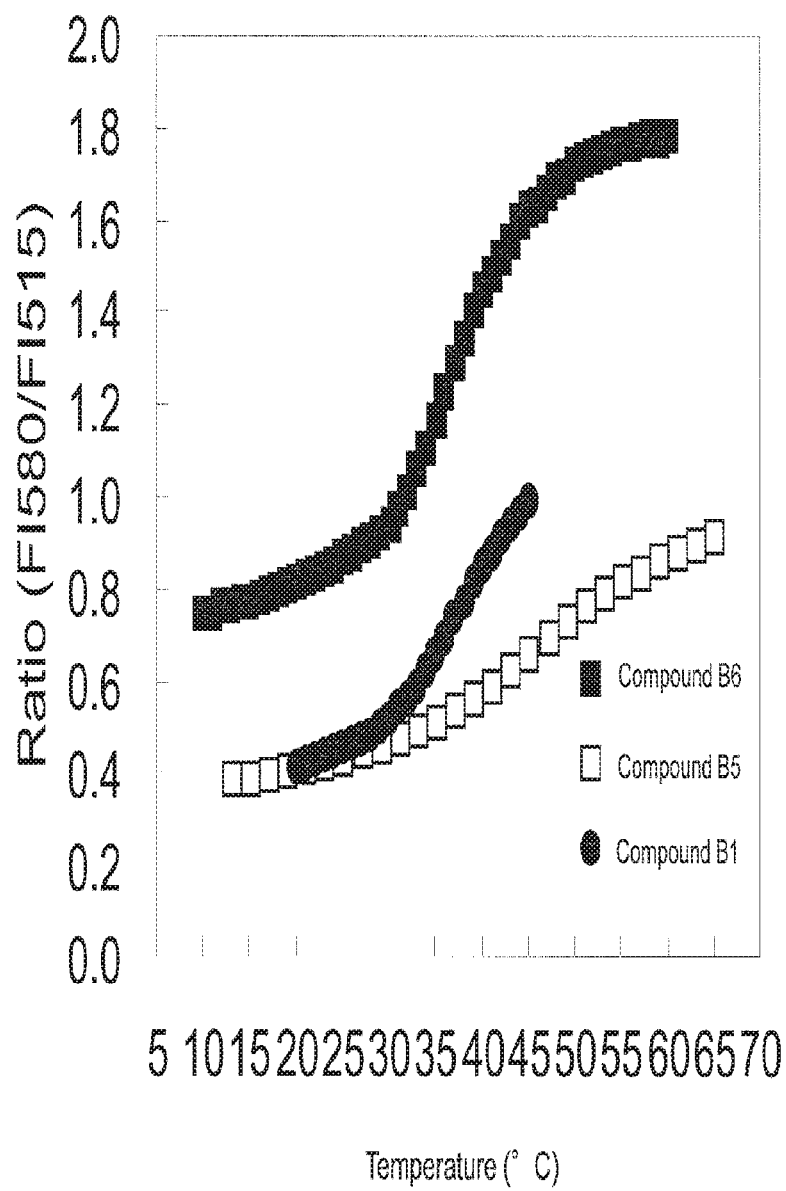
FIG. 32 is an example of thermoresponsivity test results (0.01 w/v %, excitation wavelength of 458 nm) of the ratio of fluorescence intensities (580 nm/515 nm) of compounds B1, B5, and B6 (black circle: compound B1, white square: compound B5, black square: compound B6) in an aqueous 150 mM potassium chloride solution.
Figure 33:
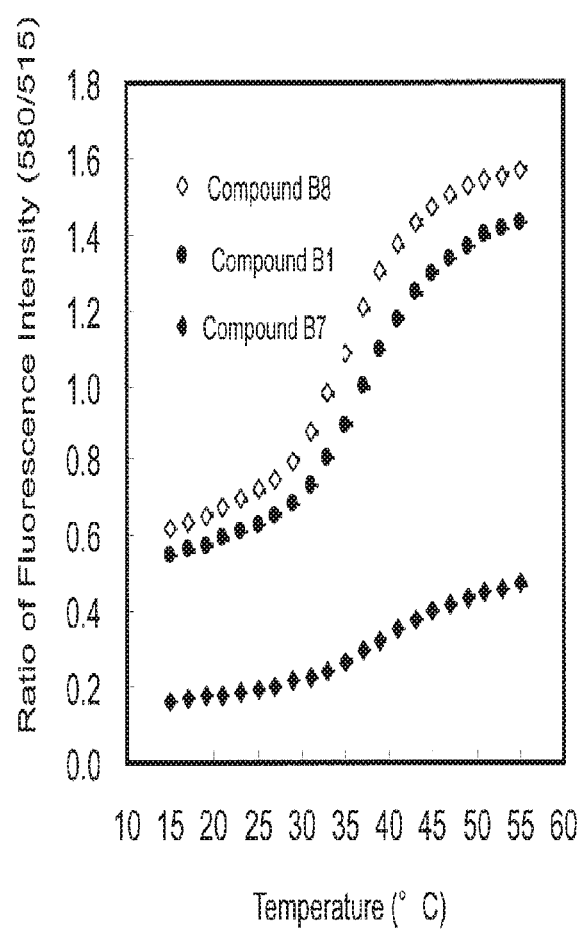
FIG. 33 is an example of thermoresponsivity test results (0.01 w/v %, excitation wavelength of 458 nm) of the ratio of fluorescence intensities (580 nm/515 nm) of compounds B1, B7, and B8 (black circle: compound B1) in an aqueous 150 mM potassium chloride solution.

Thus, a ratio of fluorescence intensity at 580 nm and 515 nm (FI580/FI510) of each compound at each temperature is shown in FIG. 31 to 33. As shown in FIG. 31, the temperature range in which a temperature-sensitive unit responds becomes higher in the order of NTBAM, NNPAM, and NIPAM; it was found that depending on the nature of a temperature-sensitive responsive element used, the responding temperature range can be freely controlled and temperature can be determined with a ratio of fluorescence intensity. As shown in FIG. 32, a ratio of fluorescence intensity for temperature was increased also in a copolymer using VBTMA as a cationic unit (compound B6). Also in a copolymer using a different composition ratio of APTMA (compound B5), a ratio of fluorescence intensity for temperature was increased. Furthermore, FIG. 33 shows that temperature can be similarly determined with an intensity ratio also for a copolymer using different two fluorescent unit ratios.

Example B9: Evaluation of Potassium Chloride Concentration Dependency in Thermoresponsivity Test The KCl concentration dependency in the thermoresponsitivity of compound B1 was tested and examined by the following procedure. The experimental methods are same as in Example B8. The initial concentration of compound B1 in this experiment was 0.005 w/v %, and a solvent was prepared so that KCl concentrations were 125 mM, 150 mM, and 175 mM.

Figure 34:
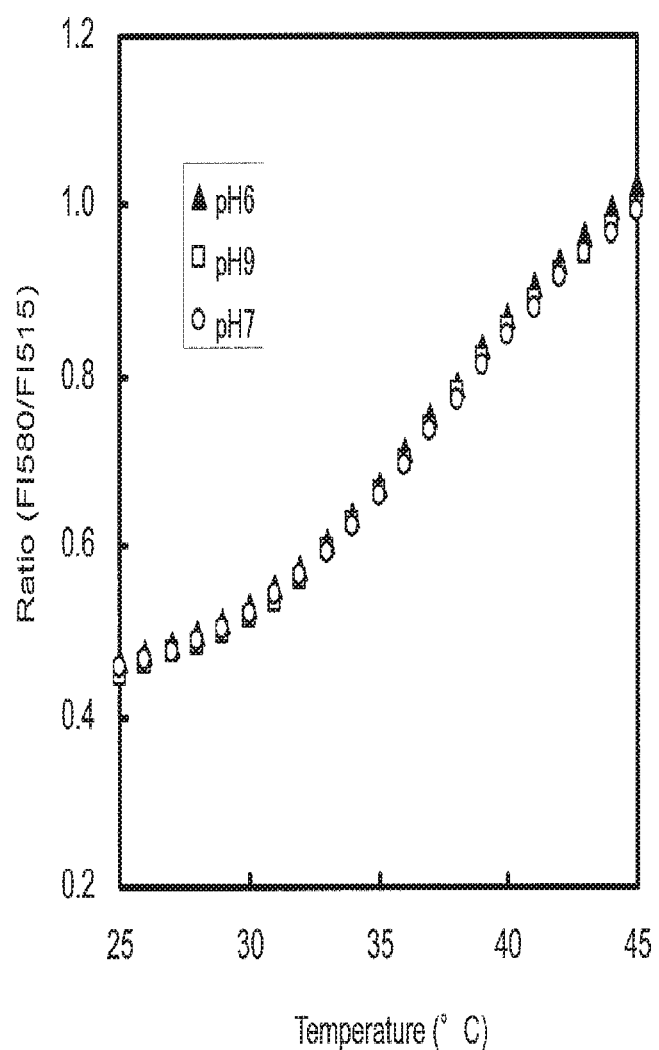
FIG. 34 is an example of thermoresponsivity test results of compound B1 in aqueous 150 mM potassium chloride solutions at pH 6 and 9 (both of which 0.01 w/v %, excitation wavelength of 458 nm) (black triangle: pH 6, white circle: pH 7, white square: pH 9).

The test results are shown in FIG. 34. Generally, intracellular potassium concentration is estimated to be about 140 mM, and it is known that change in intracellular potassium concentration is small unless there is special environmental change. Change in temperature responsivity to change in the concentration of a potassium chloride solution within the range of 125-175 mM were slightly observed, while change in intracellular potassium concentration were far lower than these changes, suggesting no effects on intracellular temperature measurement.

Example B10: Evaluation of pH Responsivity

The pH dependency in the thermoresponsitivity of compound B1 was tested and examined by the following procedure. Using 150 mM KCl as a solvent, pH was adjusted to 6 with hydrochloric acid and pH was adjusted to 9 with potassium hydroxide. The experimental methods are same as in Example B8. The initial concentration of compound B1 in this experiment was 0.005 w/v %.

Figure 35:
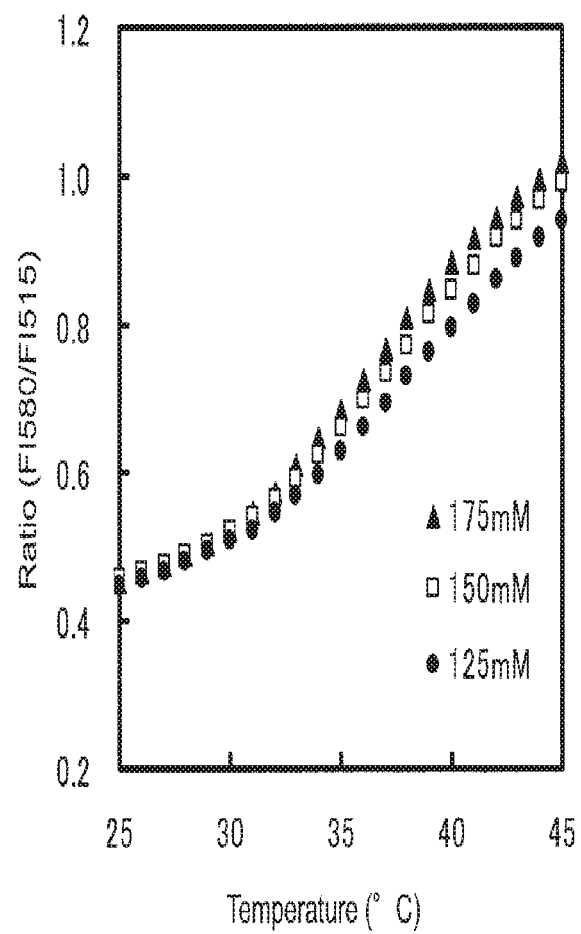
FIG. 35 is an example of thermoresponsivity test results of compound B1 in aqueous 125, 150, and 175 mM potassium chloride solutions (all of which 0.01 w/v %, excitation wavelength of 458 nm, ratio of fluorescence intensity (580 nm/515 nm)) (black triangle: in 175 mM KCl, white square: 150 mM KCl, black circle: 125 mM KCl).

The test results are shown in FIG. 35. In a usual cellular temperature range (25° C. to 45° C.), almost no change in fluorescence intensity due to change in pH were observed. In other words, it was revealed that change in pH have almost no effects on temperature responsivity, showing that fluorescence intensity reflects pH more sensitively.

Example B11: Introduction of Temperature-Sensitive Probe into Cultured Cells (Non-Adherent Cells)

MOLT-4 cell (human acute lymphoblastic leukemia (T cell)) was incubated in a RPMI 1640 medium (10% FBS) and a 100 mm dish (seeded $1 \times 10^4$ cells/ml). After two days, 3 ml of the culture solution was centrifuged (300 g, 2 minutes), and the medium was removed and the cell was washed with 5% glucose. Then, the cell was suspended in 1 ml of 5% glucose again, and each of compounds B1 to B9 was added so that the final concentration was 0.05%. At 25° C., after 10 minutes, the solution was centrifuged (300 g, 2 minutes), the supernatant was removed, and the cell was washed with PBS, and then the cell was suspended in PBS to confirm whether the probe is introduced by microscopy.

Microscopy was performed with a confocal laser scanning microscope (FV1000, Olympus) and a 40× objective lens (UplanSApo, Olympus). A laser (Multi Ar laser) of 473 nm was applied to the cell, and fluorescent images for fluorescence wavelengths ranging from 500 nm to 600 nm were observed.

Figure 36:
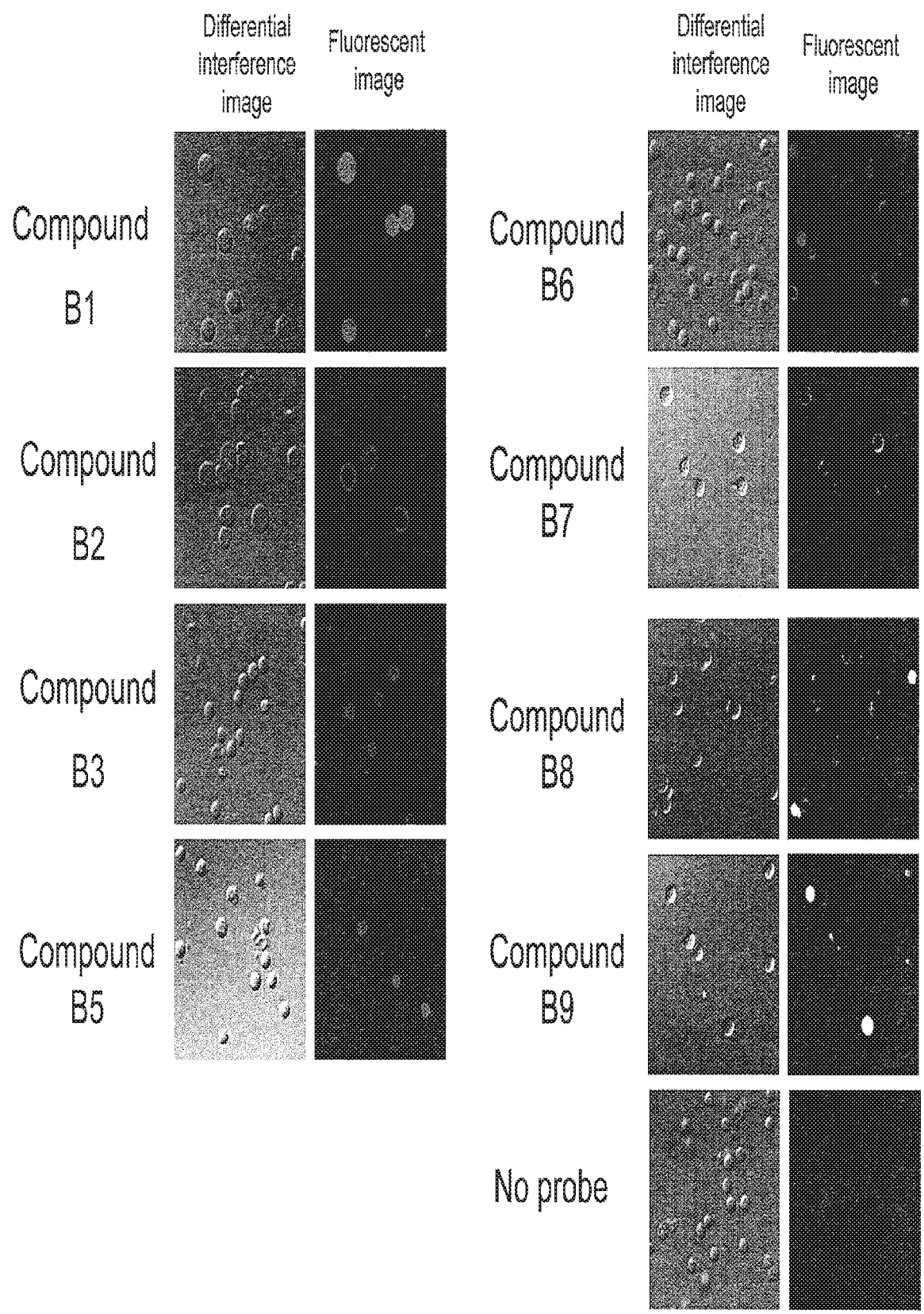
FIG. 36 is an example of photographs when each of compounds B1 to B9 was mixed with MOLT-4 cell (human acute lymphoblastic leukemia T cell) in a 5% glucose solution (25° C., 10 minutes) and observed by a microscope (excitation wavelength: 473 nm, fluorescence wavelength: 500 nm-600 nm).

The results are shown in FIG. 36. For each compound, probe introduction could be confirmed also in MOLT-4 cell, a non-adherent cell. For compound B1, the proportion of cells in which fluorescence derived from the probe could be confirmed in the cytoplasm for about 50 to 100 cells (except for the cellular intrinsic fluorescence) was 99.2±1.1(%).

Example B12: Fluorescence Intensity Response of Compound B1 for Cultured Cells (Non-Adherent Cells)

In the same manner as in Example B11, compound B1 was introduced into MOLT-4 cells. While suspended in PBS, the cell was put into a cuvette, and a spherical stirrer with a diameter of 2 mm was put into the cuvette. The cuvette was placed in a JASCO FP-6500 spectrofluorometer and rotated at a speed of about 800 rpm to prevent sinking of the cell, and fluorescence spectrum was measured. The excitation wavelength was 458 nm. A JASCO ETC-273T water-cooled Peltier thermostated cell holder was used for temperature control of the solution, and temperature was measured with its accompanying thermocouple. Solution temperature was raised in steps of 2° C., the solution was incubated for 2 minutes after temperature rise so that intracellular temperature and extracellular temperature were constant, and the fluorescence intensity at each temperature was measured.

Figure 37:
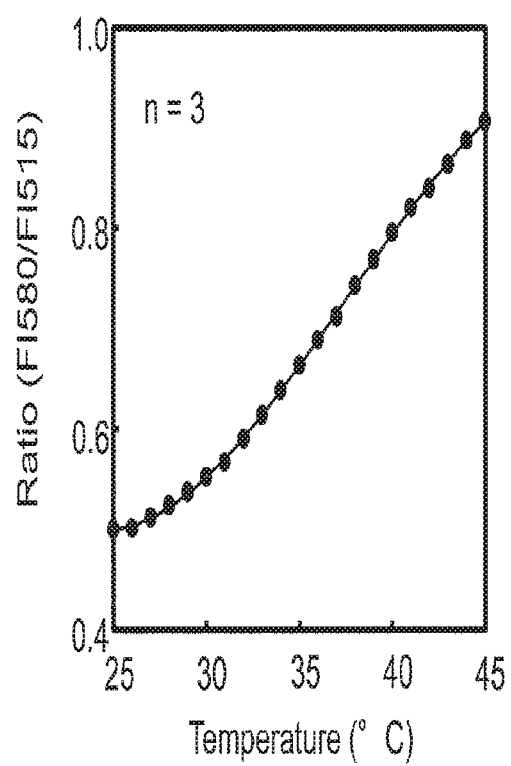
FIG. 37 is an example of thermoresponsivity test results of the ratio of fluorescence intensity (580 nm/515 nm) of compound B1 in a MOLT-4 cell (human acute lymphoblastic leukemia T cell).

The results are shown in FIG. 37. With compound B1, intracellular temperature could be calculated. It could be confirmed that intracellular temperature can be measured in a wide temperature range of 25 to 40° C., which is a growing temperature of usual mammalian cells.

Example B13: Evaluation of Temperature Resolution

As in the results of Example B8, the case in which temperature (T) was plotted on the horizontal axis and ratio of fluorescence intensity (R) was plotted on the longitudinal axis is postulated. When ∂ is defined as minute amount and δ is defined as error, the following relationship holds:

$$\frac{\delta R}{\delta T} = \frac{\partial R}{\partial T}$$

In other words, temperature resolution δT showing what temperature differences (° C.) can be detected is represented as:

$$\delta T = \left(\frac{\partial T}{\partial R}\right)\delta R$$

where ∂ represents minute amount, and thus $$\left(\frac{\partial R}{\partial T}\right)$$

represents the slope of a tangent line to a curve of a graph in which temperature (T) was plotted on the horizontal axis and ratio of fluorescence intensity (R) was plotted on the longitudinal axis. Since δ represents error, δR is error in ratio of fluorescence intensity. Here, standard deviation was used as an error value.

In other words, calculation is as follows: (temperature resolution)=(reciprocal of the slope of a tangent line to a curve of a graph in which temperature (T) was plotted on the horizontal axis and ratio of fluorescence intensity (R) was plotted on the longitudinal axis)×(error in ratio of fluorescence intensity).

Figure 38:
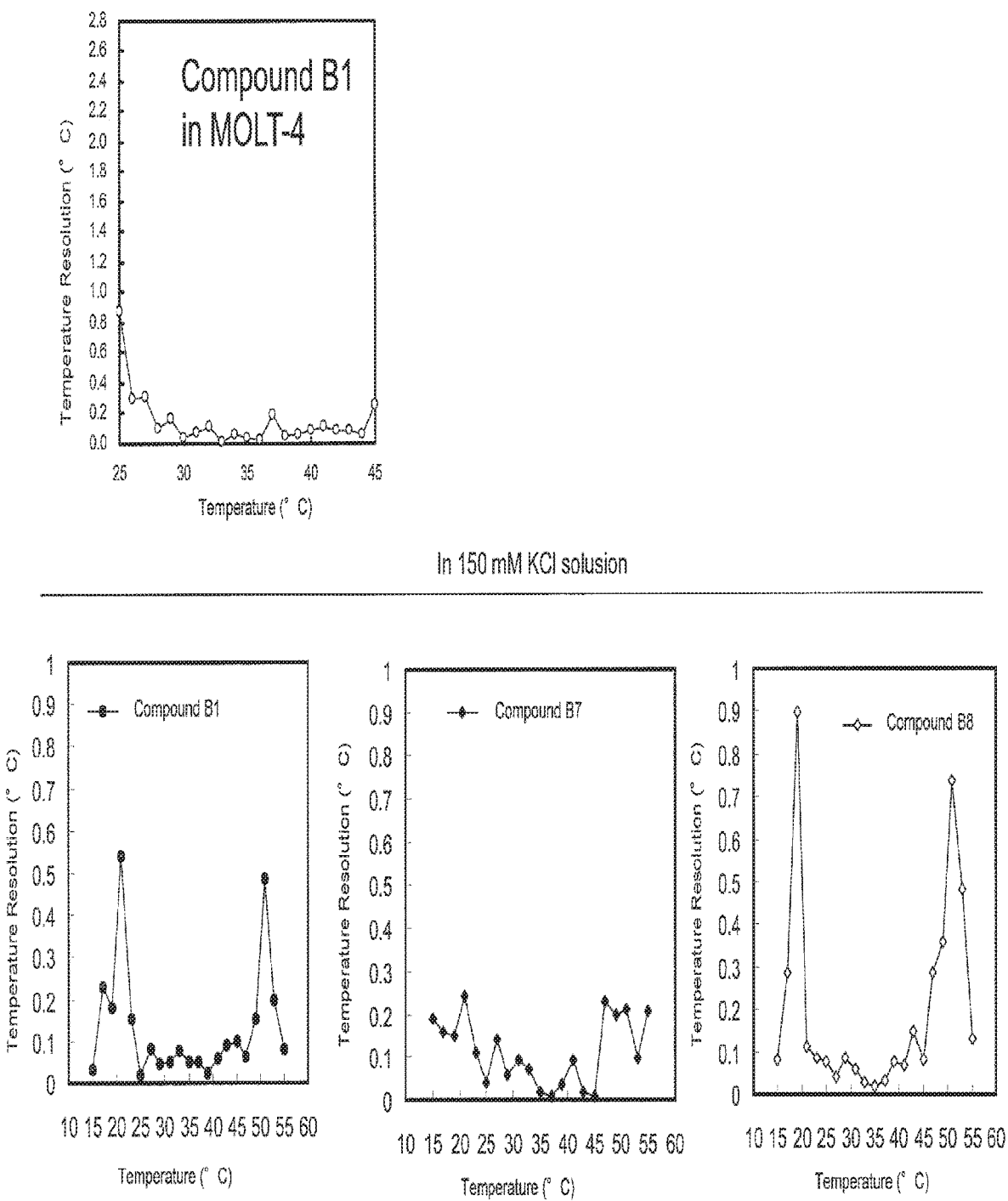
FIG. 38 is an example of temperature resolution results calculated from the thermoresponsivity test of the ratio of fluorescence intensity (580 nm/515 nm) of compound B1 in a MOLT-4 cell (human acute lymphoblastic leukemia T cell).

The results of evaluation of the temperature resolution in FIG. 37, which is the result of Example B12, are as shown in FIG. 38. For example, with regard to compound B1, it was found that there is a temperature resolution of about 0.2° C. at 30-44° C., which is a physiological temperature of usual mammalian cells, and that a very wide temperature range can be determined at high sensitivity. For FIG. 33, which shows the results of a temperature responsivity test of three compounds with different two fluorescent unit ratios (compound B1, compound B7, and compound B8) in a 150 mM KCl solution, the results of analysis of temperature resolution are also shown in FIG. 38. It was indicated that there is a high temperature resolution of about 0.1° C. in a wide temperature range of 25° C. to 45° C. in each probe.

Comparative Example B1: Intracellular Temperature Resolution of Fluorescent Temperature-Sensitive Probe Composed of Only Fluorescent Unit For compound 9, it is known that the temperature range in which the compound intracellularly and sensitively responds is within a range of ±5° C. from about 35° C. and that intracellular temperature can be sensitively measured. After washed with 5% glucose, cultured MOLT-4 cell was suspended in 1 ml of 5% glucose again, and compound 9 was added so that the final concentration was 0.05%. At 25° C., after 10 minutes, the solution was centrifuged (300 g, 2 minutes), the supernatant was removed, and the cell was washed with PBS, and then the cell was suspended in PBS to measure the fluorescence spectrum at each temperature (25 to 40° C., in steps of 1° C.) as in Example B12.

Figure 39:
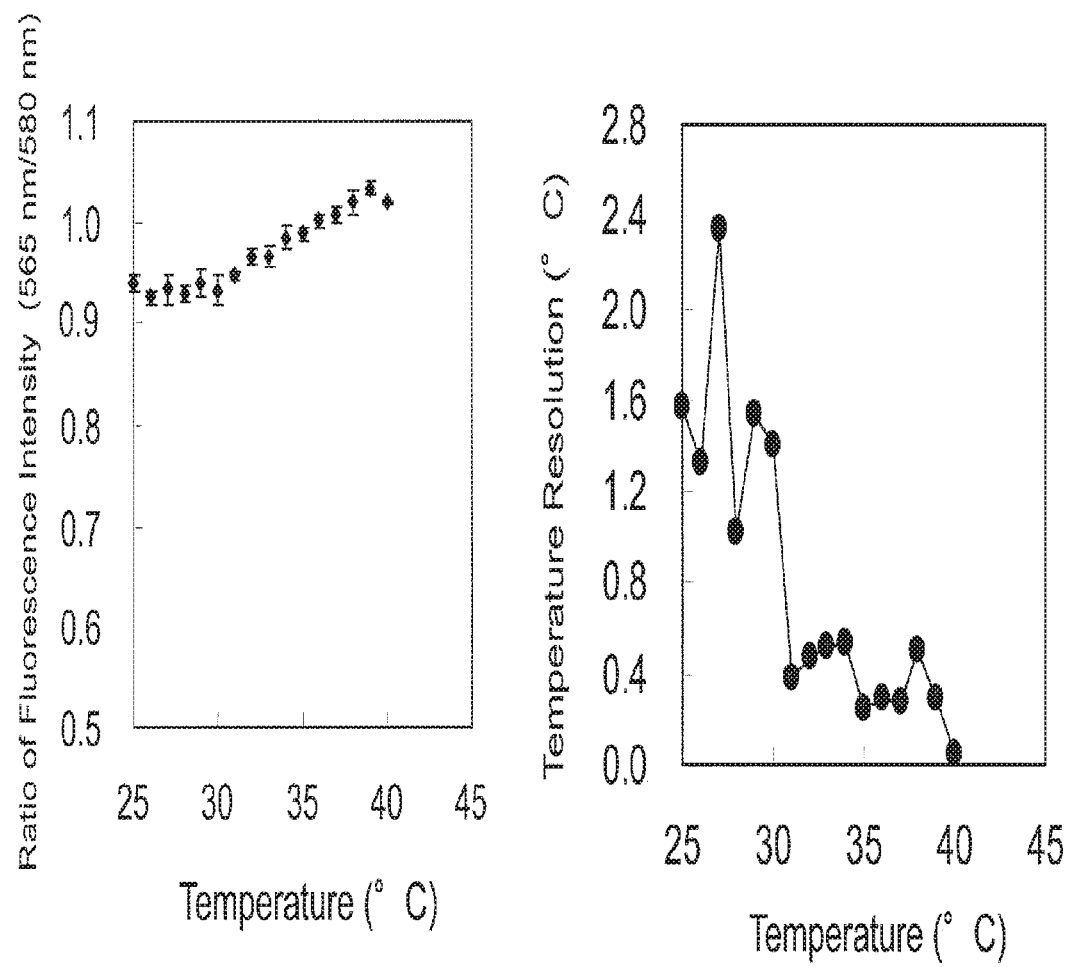
FIG. 39 is an example of the thermoresponsivity test results of the ratio of fluorescence intensity (560 nm/580 nm) of compound 9 in a MOLT-4 cell (human acute lymphoblastic leukemia T cell), and the temperature resolution results calculated from its graph.

A graph of change in ratio of fluorescence intensity and a temperature resolution when a ratio of fluorescence intensities at 565 nm (maximum fluorescence wavelength at high temperature) and 580 nm (maximum fluorescence wavelength at low temperature) is calculated are shown in FIG. 39. Even in compound 9, which seemed to have a high sensitivity, the maximum sensitivity shown is 0.05° C. at 40° C. among the range of 25–40° C., but there is only this temperature at which temperature differences smaller than 0.1° C. can be detected. In the temperature range that enables sensitive measurement at about 35° C., a temperature resolution with a value larger than 0.2° C. was shown, and mean temperature resolution from 30° C. to 40° C. was 0.45° C. On the other hand, in compound B1 in FIG. 38, mean temperature resolution in the same temperature range was 0.07° C., revealing that a novel probe synthesized this time enables highly sensitive temperature measurement.

Example B14: Application of this Probe to Adherent Cells

Human embryonic kidney cells HEK293T were incubated in a DMEM medium (5% FBS, 1% penicillin-streptomycin) and a 35 mm glass bottom dish (seeded $1\times10^3$ cells/cm$^2$). After one day, the medium was replaced with 5% glucose, and compound B1 was added so that the final concentration was 0.05% and allowed for stand at 25° C. for 10 minutes. The probe was removed, and the cell was washed with PBS, and then the medium was replaced with a phenol red-free DMEM medium, and microscopy was performed while temperature was kept at 37° C. The microscopy was performed with a confocal laser scanning microscope (FV1000, Olympus) and a 60× oil-immersion objective lens (UplanSApo N.A.1.40, Olympus). A laser (Multi Ar laser) of 473 nm was applied to the cell, and fluorescent images at 490-530 nm (P1) and fluorescent images at 560-610 nm (P2) were obtained. For P1 and P2, image processing that subtracted the fluorescence intensity in certain regions without cells as background was performed.

Figure 40:
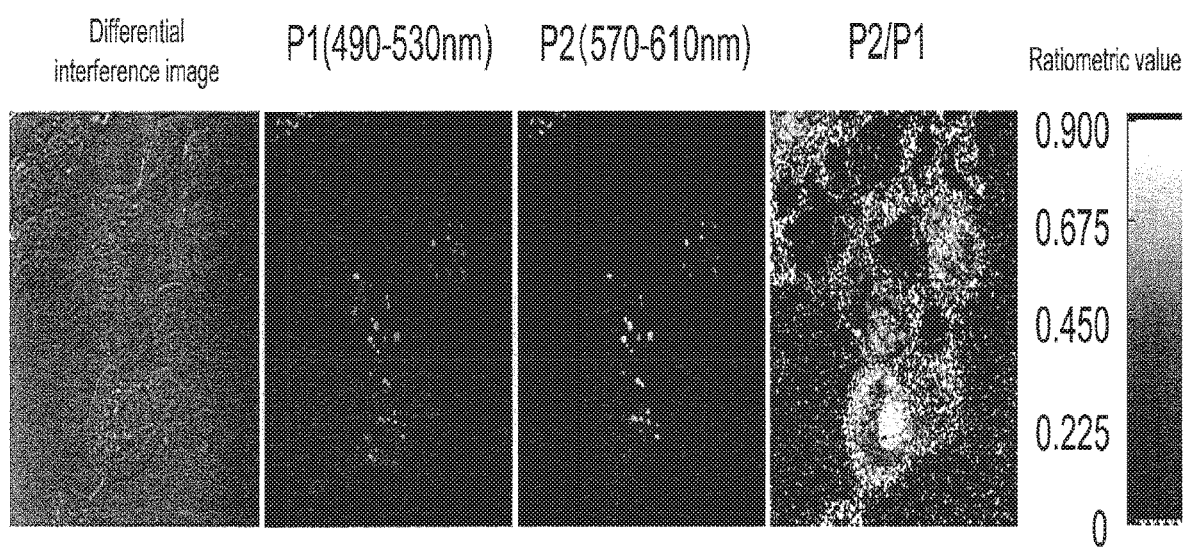
FIG. 40 is an example of fluorescent images (P2/P1) obtained by introducing compound B1 into an HEK293T cell (human embryonic kidney cell) to be observed by a confocal laser scanning microscope (excitation wavelength of 473 nm), and by calculating a ratio between fluorescent images at a fluorescence wavelength of 490-530 nm (P1) and fluorescent images at a fluorescence wavelength of 570-610 nm (P2).
Figure 41:
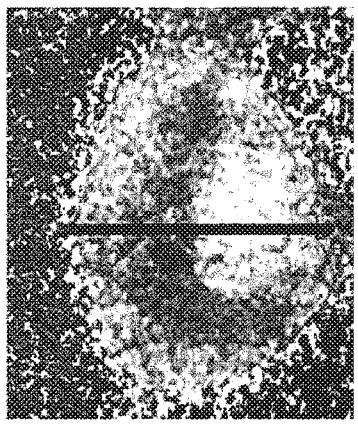
FIG. 41 is an example of a diagram in which the section view of some of the cells in FIG. 40 (black line in the left drawing) is represented as a distance from the extreme left of the black line on the horizontal axis and as a monochrome value (intensity) of the ratio image on the longitudinal axis.
Figure 41:
Figure 41:
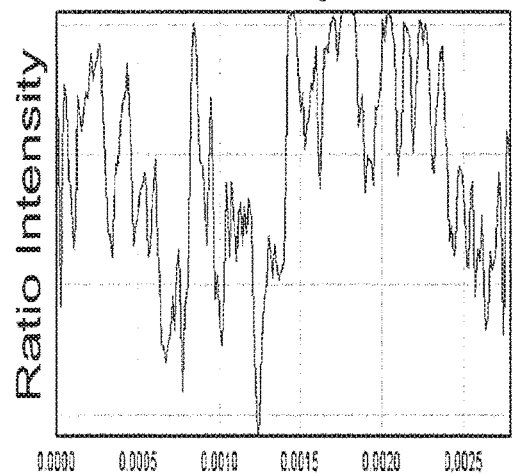

The results are shown in FIG. 40. As is clear from the results of P1 and P2, a probe can be easily introduced into adherent cells such as HEK293T. A drawing in which the fluorescence intensity value of each pixel of P2 was divided by the fluorescence intensity value of P1 is shown as P2/P1. As a result, it was revealed that intracellular temperature distribution can be visualized and determined. Furthermore, the ratio intensity (monochrome intensity value) for the section view of some of the cells is shown in FIG. 41. As a result, it was clear that there are clear differences in ratio value also in a cell. These results revealed that even a microscope that can calculate a ratio of fluorescence intensity can visualize an intracellular temperature distribution, and indicated that this probe is highly versatile technology, which could not been realized by conventional fluorescent temperature sensors.

Example B15: Evaluation of Temperature in Organelle by Microscopy

In the same manner as in Example B14, compound B1 was introduced into an HEK293T cell, the medium was replaced with a DMEM medium, and microscopy was performed at each temperature of 27° C., 32° C., and 37° C. The microscopy was performed with a confocal laser scanning microscope (FV1000, Olympus) and a 60× oil-immersion objective lens (UplanSApo N.A.1.40, Olympus). Excitation was performed with a laser (Multi Ar laser) of 473 nm, and fluorescent images at 510-520 nm (P1) and fluorescent images at 580-590 nm (P2) were obtained through an 80/20 reflector.

Figure 42:
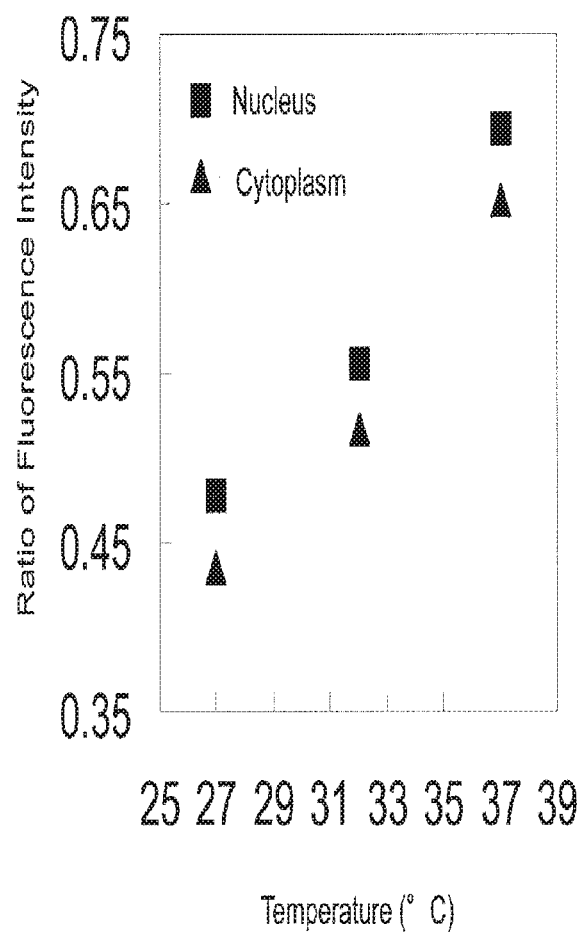
FIG. 42 is an example of differences in mean ratio of fluorescence intensity (mean of 9 cells) between cytoplasm and nucleus by temperature for the fluorescent images (P2/P1) obtained by introducing compound B1 into an HEK293T cell (human embryonic kidney cell) to be observed by a confocal laser scanning microscope (excitation wavelength of 473 nm), and by calculating a ratio between fluorescent images at a fluorescence wavelength of 510-520 nm (P1) and fluorescent images at a fluorescence wavelength of 580-590 nm (P2).

Based on the differential interference images of the cells obtained, the whole cells and the nucleus on fluorescent images were surrounded by a region of interest (ROI), and mean fluorescence intensity signal in each ROI was calculated with a FV10-ASW analysis software (Olympus). Mean fluorescence intensity signal of the cytoplasm was calculated by subtracting the signal of the nucleus from the signal of the whole cells. Furthermore, mean ratio signal of each of the cytoplasm and the nucleus was calculated by dividing the signal of P2 by the signal of P1. Mean values for 9 cells are shown in FIG. 42. The results indicated that intracellular temperature is different between cytoplasm and nucleus. Together with the results of Example B14, it was found that intracellular temperature distribution can be sensitively determined.

Example B16: Evaluation of Cytotoxicity of Probe

In the same manner as in Example B11, compound B1 was introduced into a MOLT-4 cell, and the cell was suspended in a RPMI medium. In the same manner as in Example B14, compound B1 was introduced into a HEK293T cell, and the medium was replaced with a DMEM medium. Then, for both cells, propidium iodide (PI), a non-membrane-permeable fluorescence reagent, was added into the medium so that the final concentration was 0.67 μg/ml. After the cells were processed at 37° C. for 30 minutes, observation was performed with a microscope. Compound B1 was excited with a laser of 473 nm and PI was excited with a laser of 559 nm, and observed by a fluorescence wavelength of 490-550 nm and 655-755 nm, respectively. The photomultiplier sensitivity of a camera and laser intensity at observation were adjusted using cells that were heat-treated at 95° C. for 1 minute as a control of dead cells.

About 100 cells in which the fluorescence of compound B1 was observed under a microscope were selected, and the number of cells in which the fluorescence of PI was observed was counted as the number of dead cells. The results showed that the viability of MOLT-4 cells was 97.9±1.7(%) and the viability of HEK293T cells was 100.0±0.0(%), revealing that toxicity of the temperature-sensitive probe is very low in both cells.

Example B17: Study on Probe Introduction into Myotubes and Evaluation of Temperature Responsivity After C2C12 (mouse myoblast-derived, ECACC) was incubated in a growth medium (DMEM, 10% FBS, 100 U/ml penicillin, 100 μg/ml streptomycin), the cell was seeded into a plastic bottom dish (ibidi LLC) so that the concentration was $3\times10^3$ cells/cm$^2$. After 3 days, the medium was replaced with a differentiation medium (DMEM, 2% horse serum, 100 U/ml penicillin, 100 μg/ml streptomycin), and the cell was further incubated for 7 days.

The cultured cells were washed with 5% glucose containing 0.45 mM CaCl$_2$, and 350 μl of the compound B1 suspension dissolved in 5% glucose containing 0.45 mM CaCl$_2$ (compound final concentration 0.03%) was added to a hole part (observation part) in the center of a dish, and the cells were processed at room temperature for 10 minutes. The cells were washed with PBS containing 0.45 mM CaCl$_2$, and then the medium was replaced with a medium for microscopy. Observation was performed with a confocal laser scanning microscope (FV1000, Olympus) and a 20× objective lens (UPLSAPO, NA 0.75, Olympus). A laser (Multi Ar laser) of 473 nm was irradiated to the cells, and fluorescent images for two fluorescence wavelengths of 485-545 nm (P1) and 570-670 nm (P2) were observed. Using the same methods as in Example B14, ratio images of P2/P1 were also prepared.

Figure 43:
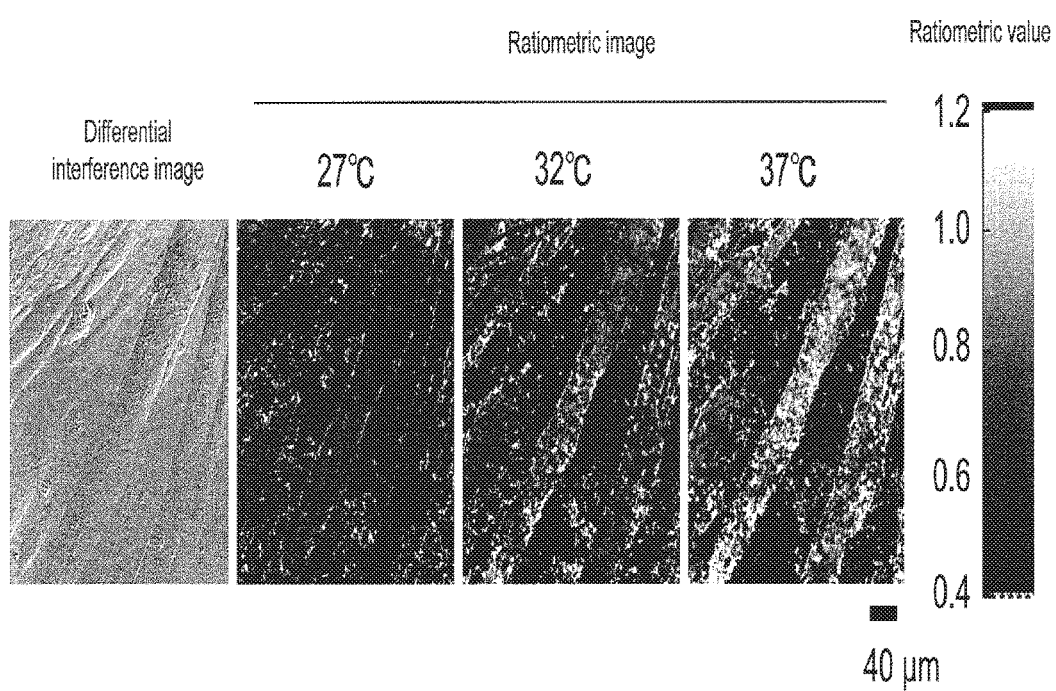
FIG. 43 is an example of change in ratio images (570-670 nm/485-545 nm) when temperature was changed after the following procedures. C2C12 differentiated into a myotube (mouse myoblast-derived, ECACC) was mixed with compound B1 (final concentration 0.03%) in a 5% glucose solution containing 0.45 mM $CaCl_2$, and compound B1 was introduced without damage to the cell, then, the cell was observed by a confocal laser scanning microscope (excitation wavelength of 473 nm).

The results are shown in FIG. 43. It was found that myotubes are damaged when Ca was removed from a medium and that a probe can be introduced without damage to cells by adding a small amount of Ca to a glucose solution at introduction. Furthermore, it could be confirmed that a ratio value is changed by changing external temperature. It was indicated that the probe can also be applied to such differentiated mature cells and intracellular temperature can be measured.

The invention claimed is:
1. A method for producing a living cell containing a temperature-sensitive probe therein, said method comprising the step of mixing the temperature-sensitive probe with the living cell in a solvent, said solvent being selected from the group consisting of water, sorbitol aqueous solution, and glucose aqueous solution, wherein the temperature-sensitive probe comprises a copolymer, the copolymer comprising a thermoresponsive unit, a cationic unit, and a fluorescent unit, wherein the copolymer comprises repeating units represented by formula (I), formula (II), and formula (III), wherein formula (I) has the structure

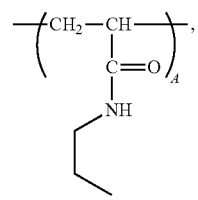

wherein formula (II) has the structure

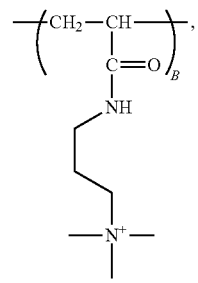

wherein formula (III) has a structure selected from the group consisting of

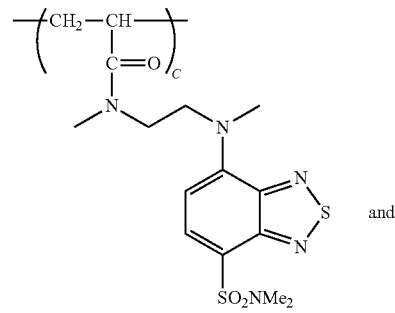

and

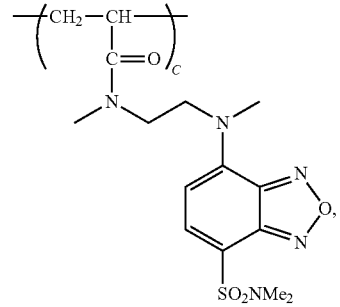

wherein A, B, and C are each numerals greater than 0 which represent the ratio of each repeating unit in said copolymer, wherein the sum of A and B is 100, B is 3 to 7.5, and C is 0.5 to 1.5, and wherein, in the step of mixing the temperature-sensitive probe with the living cell in the solvent, the concentration of the probe is 0.01 to 0.1% w/v.

* * * * *